US009241728B2

(12) United States Patent
Price et al.

(10) Patent No.: US 9,241,728 B2
(45) Date of Patent: Jan. 26, 2016

(54) SURGICAL INSTRUMENT WITH MULTIPLE CLAMPING MECHANISMS

(71) Applicant: Ethicon Endo-Surgery, Inc., Cincinnati, OH (US)

(72) Inventors: Daniel W. Price, Loveland, OH (US); Jeffrey D. Messerly, Cincinnati, OH (US); Prasanna Malaviya, Mason, OH (US); Robert J. Beetel, III, Sunnyvale, CA (US); Timothy G. Dietz, Wayne, PA (US); David A. Witt, Maineville, OH (US); Douglas J. Turner, Cincinnati, OH (US); David K. Norvell, Monroe, OH (US); John A. Weed, III, Monroe, OH (US); Kevin D. Felder, Cincinnati, OH (US); Kevin L. Houser, Springboro, OH (US); Paul T. Franer, Cincinnati, OH (US); Craig N. Faller, Batavia, OH (US); Craig T. Davis, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 233 days.

(21) Appl. No.: 13/833,706

(22) Filed: Mar. 15, 2013

(65) Prior Publication Data
US 2014/0276738 A1  Sep. 18, 2014

(51) Int. Cl.
*A61B 18/18* (2006.01)
*A61B 17/29* (2006.01)
(Continued)

(52) U.S. Cl.
CPC ..... *A61B 17/2909* (2013.01); *A61B 17/320092* (2013.01); *A61B 18/1445* (2013.01);
(Continued)

(58) Field of Classification Search
CPC .......... A61B 18/1442; A61B 18/1445; A61B 2018/145; A61B 17/2909; A61B 17/320092; A61B 19/30
USPC ................................................ 606/49, 51, 52
See application file for complete search history.

(56) References Cited

U.S. PATENT DOCUMENTS

| 969,528 A | 9/1910 | Disbrow |
| 1,570,025 A | 1/1926 | Young |

(Continued)

FOREIGN PATENT DOCUMENTS

| AU | 2003241752 A1 | 9/2003 |
| CN | 1634601 A | 7/2005 |

(Continued)

OTHER PUBLICATIONS
International Search Report for PCT/US2014/022449, dated Sep. 11, 2014 (6 pages).
(Continued)

*Primary Examiner* — Theodore Stigell
*Assistant Examiner* — Michael Carey

(57) ABSTRACT

A nested trigger assembly for a surgical instrument may generally comprise a first trigger and a second trigger, wherein the first trigger and the second trigger are movable together on a first stroke of the nested trigger assembly, wherein the second trigger is configured to be biased away from the first trigger after the first stroke and before a second stroke, and wherein the second trigger is configured to be moved toward to the first trigger during the second stroke. A surgical instrument may generally comprise a shaft comprising a proximal end and a distal end, a handle extending from the proximal end, wherein the handle comprises a gripping portion, and a nested trigger assembly extending from the handle. The nested trigger assemble may comprise one of a separable trigger assembly and a divisible trigger assembly.

40 Claims, 42 Drawing Sheets

(51) Int. Cl.
*A61B 17/32* (2006.01)
*A61B 18/14* (2006.01)
*A61B 19/00* (2006.01)
*A61B 18/00* (2006.01)

(52) U.S. Cl.
CPC ........ *A61B 19/30* (2013.01); *A61B 2017/2916* (2013.01); *A61B 2017/2919* (2013.01); *A61B 2017/2926* (2013.01); *A61B 2017/320064* (2013.01); *A61B 2018/00202* (2013.01); *A61B 2018/1455* (2013.01); *A61B 2019/307* (2013.01)

(56) References Cited

U.S. PATENT DOCUMENTS

| | | |
|---|---|---|
| 1,813,902 A | 7/1931 | Bovie |
| 2,442,966 A | 6/1948 | Wallace |
| 2,704,333 A | 3/1955 | Calosi et al. |
| 2,736,960 A | 3/1956 | Armstrong |
| 2,849,788 A | 9/1958 | Creek |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,053,124 A | 9/1962 | Balamuth et al. |
| 3,082,805 A | 3/1963 | Royce |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,526,219 A | 9/1970 | Balamuth |
| 3,554,198 A | 1/1971 | Tatoian et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,776,238 A | 12/1973 | Peyman et al. |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 4,012,647 A | 3/1977 | Balamuth et al. |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,444 A | 5/1980 | Bonnell et al. |
| 4,300,083 A | 11/1981 | Heiges |
| 4,302,728 A | 11/1981 | Nakamura |
| 4,306,570 A | 12/1981 | Matthews |
| 4,445,063 A | 4/1984 | Smith |
| 4,491,132 A | 1/1985 | Aikins |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,545,374 A | 10/1985 | Jacobson |
| 4,574,615 A | 3/1986 | Bower et al. |
| 4,617,927 A | 10/1986 | Manes |
| 4,633,119 A | 12/1986 | Thompson |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,708,127 A | 11/1987 | Abdelghani |
| 4,712,722 A | 12/1987 | Hood et al. |
| 4,808,154 A | 2/1989 | Freeman |
| 4,819,635 A | 4/1989 | Shapiro |
| 4,827,911 A | 5/1989 | Broadwin et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,850,354 A | 7/1989 | McGurk-Burleson et al. |
| 4,852,578 A | 8/1989 | Companion et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,881,550 A | 11/1989 | Kothe |
| 4,896,009 A | 1/1990 | Pawlowski |
| 4,903,696 A | 2/1990 | Stasz et al. |
| 4,915,643 A | 4/1990 | Samejima et al. |
| 4,922,902 A | 5/1990 | Wuchinich et al. |
| 4,965,532 A | 10/1990 | Sakurai |
| 4,979,952 A | 12/1990 | Kubota et al. |
| 4,981,756 A | 1/1991 | Rhandhawa |
| 5,013,956 A | 5/1991 | Kurozumi et al. |
| 5,015,227 A | 5/1991 | Broadwin et al. |
| 5,026,370 A | 6/1991 | Lottick |
| 5,026,387 A | 6/1991 | Thomas |
| 5,042,707 A | 8/1991 | Taheri |
| 5,084,052 A | 1/1992 | Jacobs |
| 5,105,117 A | 4/1992 | Yamaguchi |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,162,044 A | 11/1992 | Gahn et al. |
| 5,163,421 A | 11/1992 | Bernstein et al. |
| 5,163,537 A | 11/1992 | Radev |
| 5,167,725 A | 12/1992 | Clark et al. |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grezeszykowski |
| 5,188,102 A | 2/1993 | Idemoto et al. |
| D334,173 S | 3/1993 | Liu et al. |
| 5,209,719 A | 5/1993 | Baruch et al. |
| 5,213,569 A | 5/1993 | Davis |
| 5,214,339 A | 5/1993 | Naito |
| 5,218,529 A | 6/1993 | Meyer et al. |
| 5,221,282 A | 6/1993 | Wuchinich |
| 5,226,909 A | 7/1993 | Evans et al. |
| 5,226,910 A | 7/1993 | Kajiyama et al. |
| 5,241,236 A | 8/1993 | Sasaki et al. |
| 5,241,968 A | 9/1993 | Slater |
| 5,242,460 A | 9/1993 | Klein et al. |
| 5,254,129 A | 10/1993 | Alexander |
| 5,257,988 A | 11/1993 | L'Esperance, Jr. |
| 5,261,922 A | 11/1993 | Hood |
| 5,263,957 A | 11/1993 | Davison |
| 5,264,925 A | 11/1993 | Shipp et al. |
| 5,275,166 A | 1/1994 | Vaitekunas et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,312,023 A | 5/1994 | Green et al. |
| 5,312,425 A | 5/1994 | Evans et al. |
| 5,322,055 A | 6/1994 | Davison et al. |

(56) References Cited

U.S. PATENT DOCUMENTS

| | | |
|---|---|---|
| 5,324,299 A | 6/1994 | Davison et al. |
| 5,326,013 A | 7/1994 | Green et al. |
| 5,326,342 A | 7/1994 | Pflueger et al. |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,366,466 A | 11/1994 | Christian et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,387,215 A | 2/1995 | Fisher |
| 5,389,098 A | 2/1995 | Tsuruta et al. |
| 5,394,187 A | 2/1995 | Shipp |
| 5,396,266 A | 3/1995 | Brimhall |
| 5,403,312 A | 4/1995 | Yates et al. |
| 5,403,334 A | 4/1995 | Evans et al. |
| 5,408,268 A | 4/1995 | Shipp |
| D358,887 S | 5/1995 | Feinberg |
| 5,411,481 A | 5/1995 | Allen et al. |
| 5,419,761 A | 5/1995 | Narayanan et al. |
| 5,421,829 A | 6/1995 | Olichney et al. |
| 5,423,844 A | 6/1995 | Miller |
| 5,438,997 A | 8/1995 | Sieben et al. |
| 5,445,639 A | 8/1995 | Kuslich et al. |
| 5,449,370 A | 9/1995 | Vaitekunas |
| 5,451,220 A | 9/1995 | Ciervo |
| 5,456,684 A | 10/1995 | Schmidt et al. |
| 5,471,988 A | 12/1995 | Fujio et al. |
| 5,472,443 A | 12/1995 | Cordis et al. |
| 5,478,003 A | 12/1995 | Green et al. |
| 5,483,501 A | 1/1996 | Park et al. |
| 5,486,162 A | 1/1996 | Brumbach |
| 5,490,860 A | 2/1996 | Middle et al. |
| 5,500,216 A | 3/1996 | Julian et al. |
| 5,501,654 A | 3/1996 | Failla et al. |
| 5,505,693 A | 4/1996 | Mackool |
| 5,507,738 A | 4/1996 | Ciervo |
| 5,527,331 A | 6/1996 | Kresch et al. |
| 5,540,693 A | 7/1996 | Fisher |
| 5,558,671 A | 9/1996 | Yates |
| 5,562,609 A | 10/1996 | Brumbach |
| 5,562,610 A | 10/1996 | Brumbach |
| 5,573,424 A | 11/1996 | Poppe |
| 5,577,654 A | 11/1996 | Bishop |
| 5,591,187 A | 1/1997 | Dekel |
| 5,593,414 A | 1/1997 | Shipp et al. |
| 5,601,601 A | 2/1997 | Tal et al. |
| 5,603,773 A | 2/1997 | Campbell |
| 5,607,436 A | 3/1997 | Pratt et al. |
| 5,618,304 A | 4/1997 | Hart et al. |
| 5,618,492 A | 4/1997 | Auten et al. |
| 5,620,447 A | 4/1997 | Smith et al. |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| D381,077 S | 7/1997 | Hunt |
| 5,651,780 A | 7/1997 | Jackson et al. |
| 5,653,713 A | 8/1997 | Michelson |
| 5,669,922 A | 9/1997 | Hood |
| 5,674,235 A | 10/1997 | Parisi |
| 5,678,568 A | 10/1997 | Uchikubo et al. |
| 5,690,269 A | 11/1997 | Bolanos et al. |
| 5,694,936 A | 12/1997 | Fujimoto et al. |
| 5,704,534 A | 1/1998 | Huitema et al. |
| 5,709,680 A * | 1/1998 | Yates et al. .................. 606/50 |
| 5,711,472 A | 1/1998 | Bryan |
| 5,713,896 A | 2/1998 | Nardella |
| 5,715,817 A | 2/1998 | Stevens-Wright et al. |
| 5,717,306 A | 2/1998 | Shipp |
| 5,728,130 A | 3/1998 | Ishikawa et al. |
| 5,730,752 A | 3/1998 | Alden et al. |
| 5,733,074 A | 3/1998 | Stöck et al. |
| 5,741,226 A | 4/1998 | Strukel et al. |
| 5,766,164 A | 6/1998 | Mueller et al. |
| 5,772,659 A | 6/1998 | Becker et al. |
| 5,792,135 A | 8/1998 | Madhani et al. |
| 5,792,138 A | 8/1998 | Shipp |
| 5,792,165 A | 8/1998 | Klieman et al. |
| 5,805,140 A | 9/1998 | Rosenberg et al. |
| 5,808,396 A | 9/1998 | Boukhny |
| 5,810,859 A | 9/1998 | DiMatteo et al. |
| 5,817,084 A | 10/1998 | Jensen |
| 5,817,119 A | 10/1998 | Klieman et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,957 A | 11/1998 | Schulz et al. |
| 5,843,109 A | 12/1998 | Mehta et al. |
| 5,851,212 A | 12/1998 | Zirps et al. |
| 5,858,018 A | 1/1999 | Shipp et al. |
| 5,873,873 A | 2/1999 | Smith et al. |
| 5,873,882 A | 2/1999 | Straub et al. |
| 5,878,193 A | 3/1999 | Wang et al. |
| 5,879,364 A | 3/1999 | Bromfield et al. |
| 5,883,615 A | 3/1999 | Fago et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,627 A | 5/1999 | Spaulding |
| 5,906,628 A | 5/1999 | Miyawaki et al. |
| 5,911,699 A | 6/1999 | Anis et al. |
| 5,916,229 A | 6/1999 | Evans |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,024,741 A | 2/2000 | Williamson, IV et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,048,224 A | 4/2000 | Kay |
| 6,050,943 A | 4/2000 | Slayton et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,647 A | 5/2000 | Witt et al. |
| 6,077,285 A | 6/2000 | Boukhny |
| 6,083,191 A | 7/2000 | Rose |

(56) References Cited

U.S. PATENT DOCUMENTS

| | | |
|---|---|---|
| 6,086,584 A | 7/2000 | Miller |
| 6,090,120 A | 7/2000 | Wright et al. |
| 6,096,033 A | 8/2000 | Tu et al. |
| 6,099,542 A | 8/2000 | Cohn et al. |
| 6,109,500 A | 8/2000 | Alli et al. |
| 6,110,127 A | 8/2000 | Suzuki |
| 6,113,594 A | 9/2000 | Savage |
| 6,117,152 A | 9/2000 | Huitema |
| 6,126,629 A | 10/2000 | Perkins |
| 6,129,735 A | 10/2000 | Okada et al. |
| 6,129,740 A | 10/2000 | Michelson |
| 6,132,368 A | 10/2000 | Cooper |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,147,560 A | 11/2000 | Erhage et al. |
| 6,152,902 A | 11/2000 | Christian et al. |
| 6,154,198 A | 11/2000 | Rosenberg |
| 6,159,160 A | 12/2000 | Hsei et al. |
| 6,159,175 A | 12/2000 | Strukel et al. |
| 6,162,194 A | 12/2000 | Shipp |
| 6,165,150 A | 12/2000 | Banko |
| 6,174,310 B1 | 1/2001 | Kirwan, Jr. |
| 6,179,853 B1 | 1/2001 | Sachse et al. |
| 6,183,426 B1 | 2/2001 | Akisada et al. |
| 6,193,709 B1 | 2/2001 | Miyawaki et al. |
| 6,204,592 B1 | 3/2001 | Hur |
| 6,205,855 B1 | 3/2001 | Pfeiffer |
| 6,206,844 B1 | 3/2001 | Reichel et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,233,476 B1 | 5/2001 | Strommer et al. |
| 6,238,366 B1 | 5/2001 | Savage et al. |
| 6,245,065 B1 | 6/2001 | Panescu et al. |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,306,157 B1 | 10/2001 | Shchervinsky |
| 6,309,400 B2 | 10/2001 | Beaupre |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,350,269 B1 | 2/2002 | Shipp et al. |
| 6,352,532 B1 | 3/2002 | Kramer et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,109 B1 | 5/2002 | Davison et al. |
| 6,388,657 B1 | 5/2002 | Natoli |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,733 B1 | 6/2002 | Fogarty et al. |
| 6,416,486 B1 | 7/2002 | Wampler |
| 6,423,073 B2 | 7/2002 | Bowman |
| 6,423,082 B1 | 7/2002 | Houser et al. |
| 6,428,539 B1 | 8/2002 | Baxter et al. |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,500,312 B2 | 12/2002 | Wedekamp |
| 6,506,208 B2 | 1/2003 | Hunt et al. |
| 6,511,478 B1 | 1/2003 | Burnside et al. |
| 6,511,493 B1 | 1/2003 | Moutafis et al. |
| 6,514,267 B2 | 2/2003 | Jewett |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,558,376 B2 | 5/2003 | Bishop |
| 6,561,983 B2 | 5/2003 | Cronin et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| D477,408 S | 7/2003 | Bromley |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,607,540 B1 | 8/2003 | Shipp |
| 6,610,059 B1 | 8/2003 | West, Jr. |
| 6,616,450 B2 | 9/2003 | Mossle et al. |
| 6,619,529 B2 | 9/2003 | Green et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,644,532 B2 | 11/2003 | Green et al. |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,676,660 B2 | 1/2004 | Wampler et al. |
| 6,678,621 B2 | 1/2004 | Wiener et al. |

(56) References Cited

U.S. PATENT DOCUMENTS

| | | |
|---|---|---|
| 6,679,875 B2 | 1/2004 | Honda et al. |
| 6,679,899 B2 | 1/2004 | Wiener et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,716,215 B1 | 4/2004 | David et al. |
| 6,719,692 B2 | 4/2004 | Kleffner et al. |
| 6,719,776 B2 | 4/2004 | Baxter |
| 6,723,091 B2 | 4/2004 | Goble et al. |
| D490,059 S | 5/2004 | Conway et al. |
| 6,731,047 B2 | 5/2004 | Kauf et al. |
| 6,733,506 B1 | 5/2004 | McDevitt et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,770,072 B1 | 8/2004 | Truckai et al. |
| 6,773,409 B2 | 8/2004 | Truckai et al. |
| 6,773,443 B2 | 8/2004 | Truwit et al. |
| 6,773,444 B2 | 8/2004 | Messerly |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,790,173 B2 | 9/2004 | Saadat et al. |
| 6,790,216 B1 | 9/2004 | Ishikawa |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,827,712 B2 | 12/2004 | Tovey et al. |
| 6,828,712 B2 | 12/2004 | Battaglin et al. |
| 6,835,082 B2 | 12/2004 | Gonnering |
| 6,849,073 B2 | 2/2005 | Hoey et al. |
| 6,860,878 B2 | 3/2005 | Brock |
| 6,863,676 B2 | 3/2005 | Lee et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,899,685 B2 | 5/2005 | Kermode et al. |
| 6,905,497 B2 | 6/2005 | Truckai et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,929,602 B2 | 8/2005 | Hirakui et al. |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,994,708 B2 | 2/2006 | Manzo |
| 7,001,335 B2 | 2/2006 | Adachi et al. |
| 7,011,657 B2 | 3/2006 | Truckai et al. |
| 7,014,638 B2 | 3/2006 | Michelson |
| 7,033,357 B2 | 4/2006 | Baxter et al. |
| 7,037,306 B2 | 5/2006 | Podany |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,066,893 B2 | 6/2006 | Hibner et al. |
| 7,066,895 B2 | 6/2006 | Podany |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,101,371 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| D531,311 S | 10/2006 | Guerra et al. |
| 7,117,034 B2 | 10/2006 | Kronberg |
| 7,118,564 B2 | 10/2006 | Ritchie et al. |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,144,403 B2 | 12/2006 | Booth |
| 7,153,315 B2 | 12/2006 | Miller |
| D536,093 S | 1/2007 | Nakajima et al. |
| 7,156,189 B1 | 1/2007 | Bar-Cohen et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| D541,418 S | 4/2007 | Schechter et al. |
| 7,204,820 B2 | 4/2007 | Akahoshi |
| 7,207,997 B2 | 4/2007 | Shipp et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,229,455 B2 | 6/2007 | Sakurai et al. |
| 7,235,071 B2 | 6/2007 | Gonnering |
| 7,244,262 B2 | 7/2007 | Wiener et al. |
| 7,258,688 B1 | 8/2007 | Shah et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupré |
| 7,300,431 B2 | 11/2007 | Dubrovsky |
| 7,300,435 B2 | 11/2007 | Wham et al. |
| 7,300,446 B2 | 11/2007 | Beaupre |
| 7,303,531 B2 | 12/2007 | Lee et al. |
| 7,303,557 B2 | 12/2007 | Wham et al. |

(56) References Cited

U.S. PATENT DOCUMENTS

| | | | |
|---|---|---|---|
| 7,306,597 B2 | 12/2007 | Manzo |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,326,236 B2 | 2/2008 | Andreas et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckai et al. |
| 7,364,577 B2 | 4/2008 | Wham et al. |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,390,317 B2 | 6/2008 | Taylor et al. |
| 7,404,508 B2 | 7/2008 | Smith et al. |
| 7,408,288 B2 | 8/2008 | Hara |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,441,684 B2 | 10/2008 | Shelton, IV et al. |
| 7,455,208 B2 | 11/2008 | Wales et al. |
| 7,462,181 B2 | 12/2008 | Kraft et al. |
| 7,464,846 B2 | 12/2008 | Shelton, IV et al. |
| 7,472,815 B2 | 1/2009 | Shelton, IV et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,494,468 B2 | 2/2009 | Rabiner et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| D594,983 S | 6/2009 | Price et al. |
| 7,540,871 B2 | 6/2009 | Gonnering |
| 7,544,200 B2 | 6/2009 | Houser |
| 7,549,564 B2 | 6/2009 | Boudreaux |
| 7,559,450 B2 | 7/2009 | Wales et al. |
| 7,567,012 B2 | 7/2009 | Namikawa |
| 7,569,057 B2 | 8/2009 | Liu et al. |
| 7,572,266 B2 | 8/2009 | Young et al. |
| 7,578,820 B2 | 8/2009 | Moore et al. |
| 7,582,084 B2 | 9/2009 | Swanson et al. |
| 7,582,095 B2 | 9/2009 | Shipp et al. |
| 7,585,181 B2 | 9/2009 | Olsen |
| 7,588,176 B2 | 9/2009 | Timm et al. |
| 7,601,119 B2 | 10/2009 | Shahinian |
| 7,621,930 B2 | 11/2009 | Houser |
| 7,641,653 B2 | 1/2010 | Dalla Betta et al. |
| 7,654,431 B2 | 2/2010 | Hueil et al. |
| 7,659,833 B2 | 2/2010 | Warner et al. |
| 7,665,647 B2 | 2/2010 | Shelton, IV et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,098 B2 | 4/2010 | Wallace et al. |
| 7,699,846 B2 | 4/2010 | Ryan |
| 7,713,202 B2 | 5/2010 | Boukhny et al. |
| 7,714,481 B2 | 5/2010 | Sakai |
| 7,717,312 B2 | 5/2010 | Beetel |
| 7,717,915 B2 | 5/2010 | Miyazawa |
| D618,797 S | 6/2010 | Price et al. |
| 7,726,537 B2 | 6/2010 | Olson et al. |
| 7,727,177 B2 | 6/2010 | Bayat |
| 7,738,969 B2 | 6/2010 | Bleich |
| 7,740,594 B2 | 6/2010 | Hibner |
| 7,751,115 B2 | 7/2010 | Song |
| D621,503 S | 8/2010 | Otten et al. |
| 7,766,210 B2 | 8/2010 | Shelton, IV et al. |
| 7,766,693 B2 | 8/2010 | Sartor et al. |
| 7,770,774 B2 | 8/2010 | Mastri et al. |
| 7,770,775 B2 | 8/2010 | Shelton, IV et al. |
| 7,771,444 B2 | 8/2010 | Patel et al. |
| 7,775,972 B2 | 8/2010 | Brock et al. |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,784,662 B2 | 8/2010 | Wales et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,819,819 B2 | 10/2010 | Quick et al. |
| D627,066 S | 11/2010 | Romero |
| 7,824,401 B2 | 11/2010 | Manzo et al. |
| 7,832,611 B2 | 11/2010 | Boyden et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,876,030 B2 | 1/2011 | Taki et al. |
| D631,965 S | 2/2011 | Price et al. |
| 7,878,991 B2 | 2/2011 | Babaev |
| 7,879,033 B2 | 2/2011 | Sartor et al. |
| 7,892,606 B2 | 2/2011 | Thies et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,824 B2 | 3/2011 | Masuda et al. |
| 7,922,061 B2 | 4/2011 | Shelton, IV et al. |
| 7,922,651 B2 | 4/2011 | Yamada et al. |
| D637,288 S | 5/2011 | Houghton |
| D638,540 S | 5/2011 | Ijiri et al. |
| 7,936,203 B2 | 5/2011 | Zimlich |
| 7,951,095 B2 | 5/2011 | Makin et al. |
| 7,951,165 B2 | 5/2011 | Golden et al. |
| 7,959,050 B2 | 6/2011 | Smith et al. |
| 7,959,626 B2 | 6/2011 | Hong et al. |
| 7,972,329 B2 | 7/2011 | Refior et al. |
| 7,976,544 B2 | 7/2011 | McClurken et al. |
| 7,981,050 B2 | 7/2011 | Ritchart et al. |
| 7,998,157 B2 | 8/2011 | Culp et al. |
| 8,038,693 B2 | 10/2011 | Allen |
| 8,057,498 B2 | 11/2011 | Robertson |
| 8,058,771 B2 | 11/2011 | Giordano et al. |
| 8,061,014 B2 | 11/2011 | Smith et al. |
| 8,070,711 B2 | 12/2011 | Bassinger et al. |
| 8,070,762 B2 | 12/2011 | Escudero et al. |
| 8,075,558 B2 | 12/2011 | Truckai et al. |
| 8,089,197 B2 | 1/2012 | Rinner et al. |
| 8,097,012 B2 | 1/2012 | Kagarise |

(56) References Cited

U.S. PATENT DOCUMENTS

| | | |
|---|---|---|
| 8,105,323 B2 | 1/2012 | Buysse et al. |
| 8,142,461 B2 | 3/2012 | Houser et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,877 B2 | 5/2012 | Klimovitch et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,502 B2 | 6/2012 | Smith et al. |
| 8,210,411 B2 | 7/2012 | Yates et al. |
| 8,226,675 B2 | 7/2012 | Houser et al. |
| 8,235,917 B2 | 8/2012 | Joseph et al. |
| 8,236,019 B2 | 8/2012 | Houser |
| 8,236,020 B2 | 8/2012 | Smith et al. |
| 8,241,271 B2 | 8/2012 | Millman et al. |
| 8,246,575 B2 | 8/2012 | Viola |
| 8,246,615 B2 | 8/2012 | Behnke |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,273,087 B2 | 9/2012 | Kimura et al. |
| D669,992 S | 10/2012 | Schafer et al. |
| D669,993 S | 10/2012 | Merchant et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,298,223 B2 | 10/2012 | Wham et al. |
| 8,298,225 B2 | 10/2012 | Gilbert |
| 8,303,576 B2 | 11/2012 | Brock |
| 8,303,580 B2 | 11/2012 | Wham et al. |
| 8,319,400 B2 | 11/2012 | Houser et al. |
| 8,323,302 B2 | 12/2012 | Robertson et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,344,596 B2 | 1/2013 | Nield et al. |
| 8,348,967 B2 | 1/2013 | Stulen |
| 8,357,103 B2 | 1/2013 | Mark et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,059 B2 | 2/2013 | Deville et al. |
| 8,377,085 B2 | 2/2013 | Smith et al. |
| 8,382,775 B1 | 2/2013 | Bender et al. |
| 8,382,782 B2 | 2/2013 | Robertson et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,425,545 B2 | 4/2013 | Smith et al. |
| 8,430,898 B2 | 4/2013 | Wiener et al. |
| 8,435,257 B2 | 5/2013 | Smith et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,664 B2 | 5/2013 | Balanev et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,359 B2 | 8/2013 | Whitman et al. |
| 8,512,365 B2 | 8/2013 | Wiener et al. |
| 8,523,889 B2 | 9/2013 | Stulen et al. |
| 8,531,064 B2 | 9/2013 | Robertson et al. |
| 8,535,340 B2 | 9/2013 | Allen |
| 8,535,341 B2 | 9/2013 | Allen |
| 8,546,996 B2 | 10/2013 | Messerly et al. |
| 8,546,999 B2 | 10/2013 | Houser et al. |
| 8,568,400 B2 | 10/2013 | Gilbert |
| 8,573,461 B2 | 11/2013 | Shelton, IV et al. |
| 8,573,465 B2 | 11/2013 | Shelton, IV |
| 8,579,928 B2 | 11/2013 | Robertson et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,602,031 B2 | 12/2013 | Reis et al. |
| 8,602,288 B2 | 12/2013 | Shelton, Iv et al. |
| 8,608,745 B2 | 12/2013 | Guzman et al. |
| 8,616,431 B2 | 12/2013 | Timm et al. |
| 8,623,027 B2 | 1/2014 | Price et al. |
| 8,650,728 B2 | 2/2014 | Wan et al. |
| 8,652,155 B2 | 2/2014 | Houser et al. |
| 8,659,208 B1 | 2/2014 | Rose et al. |
| 8,663,220 B2 | 3/2014 | Wiener et al. |
| 8,690,582 B2 | 4/2014 | Rohrbach et al. |
| 8,696,366 B2 | 4/2014 | Chen et al. |
| 8,704,425 B2 | 4/2014 | Giordano et al. |
| 8,709,031 B2 | 4/2014 | Stulen |
| 8,749,116 B2 | 6/2014 | Messerly et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,764,735 B2 | 7/2014 | Coe et al. |
| 8,773,001 B2 | 7/2014 | Wiener et al. |
| 8,779,648 B2 | 7/2014 | Giordano et al. |
| 8,808,319 B2 | 8/2014 | Houser et al. |
| 8,827,992 B2 | 9/2014 | Koss et al. |
| 8,845,537 B2 | 9/2014 | Tanaka et al. |
| 8,882,791 B2 | 11/2014 | Stulen |
| 8,888,776 B2 | 11/2014 | Dietz et al. |
| 8,888,809 B2 | 11/2014 | Davison et al. |
| 8,900,259 B2 | 12/2014 | Houser et al. |
| 8,911,460 B2 | 12/2014 | Neurohr et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,547 B2 | 2/2015 | Dietz et al. |
| 8,968,355 B2 | 3/2015 | Malkowski et al. |
| 8,974,477 B2 | 3/2015 | Yamada |
| 8,979,890 B2 | 3/2015 | Boudreaux |
| 8,986,287 B2 | 3/2015 | Park et al. |
| 8,986,302 B2 | 3/2015 | Aldridge et al. |
| 8,989,903 B2 | 3/2015 | Weir et al. |
| 9,017,326 B2 | 4/2015 | DiNardo et al. |
| 9,039,695 B2 | 5/2015 | Giordano et al. |
| 9,044,261 B2 | 6/2015 | Houser |
| 9,050,093 B2 | 6/2015 | Aldridge et al. |
| 9,050,124 B2 | 6/2015 | Houser |
| 9,060,775 B2 | 6/2015 | Wiener et al. |
| 9,060,776 B2 | 6/2015 | Yates et al. |
| 9,066,747 B2 | 6/2015 | Robertson |
| 9,072,539 B2 | 7/2015 | Messerly et al. |
| 2001/0025173 A1 | 9/2001 | Ritchie et al. |
| 2001/0025183 A1 | 9/2001 | Shahidi et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |

(56) References Cited

U.S. PATENT DOCUMENTS

| | | |
|---|---|---|
| 2002/0019649 A1 | 2/2002 | Sikora et al. |
| 2002/0022836 A1 | 2/2002 | Goble et al. |
| 2002/0029055 A1 | 3/2002 | Bonutti |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0156466 A1 | 10/2002 | Sakurai et al. |
| 2002/0156493 A1 | 10/2002 | Houser et al. |
| 2003/0014087 A1 | 1/2003 | Fang et al. |
| 2003/0036705 A1 | 2/2003 | Hare et al. |
| 2003/0050572 A1 | 3/2003 | Brautigam et al. |
| 2003/0055443 A1 | 3/2003 | Spotnitz |
| 2003/0114851 A1 | 6/2003 | Truckai et al. |
| 2003/0144680 A1 | 7/2003 | Kellogg et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0092921 A1 | 5/2004 | Kadziauskas et al. |
| 2004/0092992 A1 | 5/2004 | Adams et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0132383 A1 | 7/2004 | Langford et al. |
| 2004/0147934 A1 | 7/2004 | Kiester |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0199193 A1 | 10/2004 | Hayashi et al. |
| 2004/0204728 A1 | 10/2004 | Haefner |
| 2004/0243147 A1 | 12/2004 | Lipow |
| 2004/0260300 A1 | 12/2004 | Gorensek et al. |
| 2005/0021018 A1 | 1/2005 | Anderson et al. |
| 2005/0021065 A1 | 1/2005 | Yamada et al. |
| 2005/0033337 A1 | 2/2005 | Muir et al. |
| 2005/0049546 A1 | 3/2005 | Messerly et al. |
| 2005/0070800 A1 | 3/2005 | Takahashi |
| 2005/0096683 A1 | 5/2005 | Ellins et al. |
| 2005/0099824 A1 | 5/2005 | Dowling et al. |
| 2005/0103819 A1 | 5/2005 | Racenet et al. |
| 2005/0143769 A1 | 6/2005 | White et al. |
| 2005/0149108 A1 | 7/2005 | Cox |
| 2005/0165345 A1 | 7/2005 | Laufer et al. |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0209620 A1 | 9/2005 | Du et al. |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261581 A1 | 11/2005 | Hughes et al. |
| 2005/0261588 A1 | 11/2005 | Makin et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0066181 A1 | 3/2006 | Bromfield et al. |
| 2006/0074442 A1 | 4/2006 | Noriega et al. |
| 2006/0079879 A1 | 4/2006 | Faller et al. |
| 2006/0084963 A1 | 4/2006 | Messerly |
| 2006/0095046 A1 | 5/2006 | Trieu et al. |
| 2006/0129146 A1* | 6/2006 | Dycus et al. .............. 606/51 |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0235306 A1 | 10/2006 | Cotter et al. |
| 2006/0247558 A1 | 11/2006 | Yamada |
| 2006/0253050 A1 | 11/2006 | Yoshimine et al. |
| 2006/0264809 A1 | 11/2006 | Hansmann et al. |
| 2006/0271030 A1 | 11/2006 | Francis et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0056596 A1 | 3/2007 | Fanney et al. |
| 2007/0060915 A1 | 3/2007 | Kucklick |
| 2007/0060935 A1 | 3/2007 | Schwardt et al. |
| 2007/0063618 A1 | 3/2007 | Bromfield |
| 2007/0074584 A1 | 4/2007 | Talarico et al. |
| 2007/0106317 A1 | 5/2007 | Shelton, IV et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0162050 A1 | 7/2007 | Sartor |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175949 A1 | 8/2007 | Shelton, IV et al. |
| 2007/0185380 A1 | 8/2007 | Kucklick |
| 2007/0191712 A1 | 8/2007 | Messerly et al. |
| 2007/0219481 A1 | 9/2007 | Babaev |
| 2007/0239028 A1 | 10/2007 | Houser et al. |
| 2007/0239101 A1 | 10/2007 | Kellogg |
| 2007/0249941 A1 | 10/2007 | Salehi et al. |
| 2007/0260234 A1 | 11/2007 | McCullagh et al. |
| 2007/0265560 A1 | 11/2007 | Soltani et al. |
| 2007/0275348 A1 | 11/2007 | Lemon |
| 2007/0282335 A1 | 12/2007 | Young et al. |
| 2007/0287933 A1 | 12/2007 | Phan et al. |
| 2008/0009848 A1 | 1/2008 | Paraschiv et al. |
| 2008/0013809 A1 | 1/2008 | Zhu et al. |
| 2008/0051812 A1 | 2/2008 | Schmitz et al. |
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0114364 A1 | 5/2008 | Goldin et al. |
| 2008/0125768 A1 | 5/2008 | Tahara et al. |
| 2008/0140158 A1 | 6/2008 | Hamel et al. |
| 2008/0147092 A1 | 6/2008 | Rogge et al. |
| 2008/0171938 A1 | 7/2008 | Masuda et al. |
| 2008/0172051 A1 | 7/2008 | Masuda et al. |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243106 A1 | 10/2008 | Coe et al. |
| 2008/0243162 A1 | 10/2008 | Shibata et al. |
| 2008/0245371 A1 | 10/2008 | Gruber |
| 2008/0249553 A1 | 10/2008 | Gruber et al. |
| 2008/0255423 A1 | 10/2008 | Kondo et al. |
| 2008/0262490 A1 | 10/2008 | Williams |
| 2008/0281200 A1 | 11/2008 | Voic et al. |
| 2008/0281315 A1 | 11/2008 | Gines |
| 2008/0281322 A1 | 11/2008 | Sherman et al. |
| 2008/0287948 A1 | 11/2008 | Newton et al. |
| 2009/0023985 A1 | 1/2009 | Ewers |
| 2009/0048537 A1 | 2/2009 | Lydon et al. |
| 2009/0054886 A1 | 2/2009 | Yachi et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0112229 A1 | 4/2009 | Omori et al. |
| 2009/0118751 A1 | 5/2009 | Wiener et al. |

(56) References Cited

U.S. PATENT DOCUMENTS

| | | |
|---|---|---|
| 2009/0118802 A1 | 5/2009 | Mioduski et al. |
| 2009/0138006 A1 | 5/2009 | Bales et al. |
| 2009/0143799 A1 | 6/2009 | Smith et al. |
| 2009/0143800 A1 | 6/2009 | Deville et al. |
| 2009/0143806 A1 | 6/2009 | Witt et al. |
| 2009/0149801 A1 | 6/2009 | Crandall et al. |
| 2009/0207923 A1 | 8/2009 | Dress |
| 2009/0216157 A1 | 8/2009 | Yamada |
| 2009/0223033 A1 | 9/2009 | Houser |
| 2009/0254077 A1 | 10/2009 | Craig |
| 2009/0254080 A1 | 10/2009 | Honda |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270899 A1 | 10/2009 | Carusillo et al. |
| 2009/0275940 A1 | 11/2009 | Malackowski et al. |
| 2009/0318945 A1 | 12/2009 | Yoshimine et al. |
| 2009/0327715 A1 | 12/2009 | Smith et al. |
| 2010/0004508 A1 | 1/2010 | Naito et al. |
| 2010/0016785 A1 | 1/2010 | Takuma |
| 2010/0016852 A1 | 1/2010 | Manzo et al. |
| 2010/0022825 A1 | 1/2010 | Yoshie |
| 2010/0030233 A1 | 2/2010 | Whitman et al. |
| 2010/0030248 A1 | 2/2010 | Palmer et al. |
| 2010/0036370 A1 | 2/2010 | Mirel et al. |
| 2010/0042077 A1 | 2/2010 | Okada |
| 2010/0049180 A1 | 2/2010 | Wells et al. |
| 2010/0063525 A1 | 3/2010 | Beaupre et al. |
| 2010/0063528 A1 | 3/2010 | Beaupré |
| 2010/0069940 A1 | 3/2010 | Miller et al. |
| 2010/0158307 A1 | 6/2010 | Kubota et al. |
| 2010/0187283 A1 | 7/2010 | Crainich et al. |
| 2010/0222714 A1 | 9/2010 | Muir et al. |
| 2010/0228264 A1 | 9/2010 | Robinson et al. |
| 2010/0234906 A1 | 9/2010 | Koh |
| 2010/0262134 A1 | 10/2010 | Jensen et al. |
| 2010/0274160 A1 | 10/2010 | Yachi et al. |
| 2010/0280407 A1 | 11/2010 | Polster |
| 2010/0292691 A1 | 11/2010 | Brogna |
| 2010/0298743 A1 | 11/2010 | Nield et al. |
| 2010/0298851 A1 | 11/2010 | Nield |
| 2010/0331742 A1 | 12/2010 | Masuda |
| 2011/0004233 A1 | 1/2011 | Muir et al. |
| 2011/0009850 A1 | 1/2011 | Main et al. |
| 2011/0077648 A1 | 3/2011 | Lee et al. |
| 2011/0082486 A1 | 4/2011 | Messerly et al. |
| 2011/0087218 A1 | 4/2011 | Boudreaux et al. |
| 2011/0112526 A1 | 5/2011 | Fritz et al. |
| 2011/0125151 A1 | 5/2011 | Strauss et al. |
| 2011/0125174 A1 | 5/2011 | Babaev |
| 2011/0144806 A1 | 6/2011 | Sandhu et al. |
| 2011/0196399 A1 | 8/2011 | Robertson et al. |
| 2011/0224689 A1 | 9/2011 | Larkin et al. |
| 2011/0238065 A1 | 9/2011 | Hunt et al. |
| 2011/0257650 A1 | 10/2011 | Deville et al. |
| 2011/0270126 A1 | 11/2011 | Gunday et al. |
| 2011/0290853 A1 | 12/2011 | Shelton, IV et al. |
| 2011/0290856 A1 | 12/2011 | Shelton, IV et al. |
| 2012/0004655 A1 | 1/2012 | Kim et al. |
| 2012/0022525 A1 | 1/2012 | Dietz et al. |
| 2012/0022530 A1 | 1/2012 | Woodruff et al. |
| 2012/0022583 A1 | 1/2012 | Sugalski et al. |
| 2012/0059289 A1 | 3/2012 | Nield et al. |
| 2012/0065628 A1 | 3/2012 | Naito |
| 2012/0071863 A1 | 3/2012 | Lee et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078278 A1 | 3/2012 | Bales, Jr. et al. |
| 2012/0080332 A1 | 4/2012 | Shelton, IV et al. |
| 2012/0101495 A1 | 4/2012 | Young et al. |
| 2012/0109159 A1 | 5/2012 | Jordan et al. |
| 2012/0116379 A1 | 5/2012 | Yates et al. |
| 2012/0116391 A1 | 5/2012 | Houser et al. |
| 2012/0116394 A1 | 5/2012 | Timm et al. |
| 2012/0116395 A1 | 5/2012 | Madan et al. |
| 2012/0130256 A1 | 5/2012 | Buysse et al. |
| 2012/0130365 A1 | 5/2012 | McLawhorn |
| 2012/0136354 A1 | 5/2012 | Rupp |
| 2012/0138660 A1 | 6/2012 | Shelton, IV |
| 2012/0143211 A1 | 6/2012 | Kishi |
| 2012/0150170 A1 | 6/2012 | Buysse et al. |
| 2012/0165816 A1 | 6/2012 | Kersten et al. |
| 2012/0172873 A1 | 7/2012 | Artale et al. |
| 2012/0172904 A1 | 7/2012 | Muir et al. |
| 2012/0177005 A1 | 7/2012 | Liang et al. |
| 2012/0184946 A1 | 7/2012 | Price et al. |
| 2012/0199630 A1 | 8/2012 | Shelton, IV |
| 2012/0199632 A1 | 8/2012 | Spivey et al. |
| 2012/0203143 A1 | 8/2012 | Sanai et al. |
| 2012/0203247 A1 | 8/2012 | Shelton, IV et al. |
| 2012/0209289 A1 | 8/2012 | Duque et al. |
| 2012/0209303 A1 | 8/2012 | Frankhouser et al. |
| 2012/0210223 A1 | 8/2012 | Eppolito |
| 2012/0215220 A1 | 8/2012 | Manzo et al. |
| 2012/0245582 A1 | 9/2012 | Kimball et al. |
| 2012/0253370 A1 | 10/2012 | Ross et al. |
| 2012/0265196 A1 | 10/2012 | Turner et al. |
| 2012/0269676 A1 | 10/2012 | Houser et al. |
| 2012/0330307 A1 | 12/2012 | Ladtkow et al. |
| 2013/0012957 A1 | 1/2013 | Shelton, IV et al. |
| 2013/0030433 A1 | 1/2013 | Heard |
| 2013/0035680 A1 | 2/2013 | Ben-Haim et al. |
| 2013/0053840 A1 | 2/2013 | Krapohl et al. |
| 2013/0072856 A1 | 3/2013 | Frankhouser et al. |
| 2013/0072857 A1 | 3/2013 | Frankhouser et al. |
| 2013/0079762 A1 | 3/2013 | Twomey et al. |
| 2013/0103023 A1 | 4/2013 | Monson et al. |
| 2013/0103024 A1 | 4/2013 | Monson et al. |
| 2013/0110145 A1 | 5/2013 | Weitzman |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0123822 A1 | 5/2013 | Wellman et al. |
| 2013/0131660 A1 | 5/2013 | Monson et al. |
| 2013/0165929 A1 | 6/2013 | Muir et al. |
| 2013/0211397 A1 | 8/2013 | Parihar et al. |
| 2013/0217967 A1 | 8/2013 | Mohr et al. |
| 2013/0226207 A1 | 8/2013 | Stulen et al. |
| 2013/0226208 A1 | 8/2013 | Wiener et al. |
| 2013/0245659 A1 | 9/2013 | Robertson et al. |
| 2013/0267975 A1 | 10/2013 | Timm et al. |
| 2013/0274734 A1 | 10/2013 | Maass et al. |
| 2013/0282003 A1 | 10/2013 | Messerly et al. |
| 2013/0282038 A1 | 10/2013 | Dannaher et al. |
| 2013/0282039 A1 | 10/2013 | Wiener et al. |
| 2013/0285758 A1 | 10/2013 | Aldridge et al. |
| 2013/0289591 A1 | 10/2013 | Boudreaux et al. |
| 2013/0296908 A1 | 11/2013 | Schulte et al. |
| 2013/0338661 A1 | 12/2013 | Behnke, II |
| 2013/0345689 A1 | 12/2013 | Ruddenklau et al. |
| 2013/0345733 A1 | 12/2013 | Robertson et al. |
| 2014/0005640 A1 | 1/2014 | Shelton, IV et al. |
| 2014/0005653 A1 | 1/2014 | Shelton, IV et al. |
| 2014/0005654 A1 | 1/2014 | Batross et al. |
| 2014/0005656 A1 | 1/2014 | Mucilli et al. |
| 2014/0005661 A1 | 1/2014 | Shelton, IV et al. |
| 2014/0005662 A1 | 1/2014 | Shelton, IV et al. |
| 2014/0005667 A1 | 1/2014 | Stulen et al. |
| 2014/0005668 A1 | 1/2014 | Rhee et al. |
| 2014/0005676 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005682 A1 | 1/2014 | Worrell et al. |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005704 A1 | 1/2014 | Vakharia et al. |
| 2014/0005705 A1 | 1/2014 | Weir et al. |
| 2014/0005708 A1 | 1/2014 | Shelton, IV et al. |
| 2014/0005718 A1 | 1/2014 | Shelton, IV et al. |
| 2014/0012299 A1 | 1/2014 | Stoddard et al. |
| 2014/0066962 A1 | 3/2014 | Robertson et al. |

(56) References Cited

U.S. PATENT DOCUMENTS

| | | | |
|---|---|---|---|
| 2014/0087569 A1 | 3/2014 | Lee |
| 2014/0107538 A1 | 4/2014 | Wiener et al. |
| 2014/0114327 A1 | 4/2014 | Boudreaux et al. |
| 2014/0135804 A1 | 5/2014 | Weisenburgh, II et al. |
| 2014/0155921 A1 | 6/2014 | Price et al. |
| 2014/0180280 A1 | 6/2014 | Sigmon, Jr. |
| 2014/0243864 A1 | 8/2014 | Voegele et al. |
| 2014/0276970 A1 | 9/2014 | Messerly et al. |
| 2014/0336686 A1 | 11/2014 | Houser et al. |
| 2015/0045819 A1 | 2/2015 | Houser et al. |
| 2015/0066067 A1 | 3/2015 | Stulen |
| 2015/0073460 A1 | 3/2015 | Stulen |
| 2015/0112335 A1 | 4/2015 | Boudreaux et al. |
| 2015/0119914 A1 | 4/2015 | Neurohr et al. |
| 2015/0119915 A1 | 4/2015 | Neurohr et al. |
| 2015/0119916 A1 | 4/2015 | Dietz et al. |
| 2015/0123348 A1 | 5/2015 | Robertson et al. |
| 2015/0157355 A1 | 6/2015 | Price et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0182251 A1 | 7/2015 | Messerly et al. |
| 2015/0182276 A1 | 7/2015 | Wiener et al. |
| 2015/0182277 A1 | 7/2015 | Wiener et al. |

FOREIGN PATENT DOCUMENTS

| | | |
|---|---|---|
| CN | 1640365 A | 7/2005 |
| CN | 1694649 A | 11/2005 |
| CN | 1922563 A | 2/2007 |
| CN | 1951333 A | 4/2007 |
| CN | 101040799 A | 9/2007 |
| CN | 101467917 A | 1/2009 |
| DE | 3904558 A1 | 8/1990 |
| DE | 9210327 U1 | 11/1992 |
| DE | 4323585 A1 | 1/1995 |
| DE | 19608716 C1 | 4/1997 |
| DE | 20021619 U1 | 3/2001 |
| DE | 10042606 A1 | 8/2001 |
| EP | 0136855 B1 | 9/1984 |
| EP | 0171967 A2 | 2/1986 |
| EP | 1839599 A1 | 10/1987 |
| EP | 0336742 A2 | 4/1989 |
| EP | 0424685 B1 | 5/1991 |
| EP | 0443256 A1 | 8/1991 |
| EP | 0456470 A1 | 11/1991 |
| EP | 0598976 A2 | 1/1994 |
| EP | 0677275 A2 | 3/1995 |
| EP | 0482195 B1 | 1/1996 |
| EP | 0695535 A1 | 2/1996 |
| EP | 0741996 A2 | 11/1996 |
| EP | 0612570 B1 | 6/1997 |
| EP | 1108394 A2 | 6/2001 |
| EP | 0908148 B1 | 1/2002 |
| EP | 1229515 A2 | 8/2002 |
| EP | 1285634 A1 | 2/2003 |
| EP | 0908155 B1 | 6/2003 |
| EP | 0705570 B1 | 4/2004 |
| EP | 0765637 B1 | 7/2004 |
| EP | 0870473 B1 | 9/2005 |
| EP | 0624346 B1 | 11/2005 |
| EP | 1594209 A1 | 11/2005 |
| EP | 1199044 B1 | 12/2005 |
| EP | 1609428 A1 | 12/2005 |
| EP | 1199043 B1 | 3/2006 |
| EP | 1433425 B1 | 6/2006 |
| EP | 1256323 B1 | 9/2006 |
| EP | 1704824 A1 | 9/2006 |
| EP | 1749479 A1 | 2/2007 |
| EP | 1815950 A1 | 8/2007 |
| EP | 1844720 A1 | 10/2007 |
| EP | 1862133 A1 | 12/2007 |
| EP | 1875875 A1 | 1/2008 |
| EP | 1199045 B1 | 6/2008 |
| EP | 1964530 A1 | 9/2008 |
| EP | 1972264 A1 | 9/2008 |
| EP | 1974771 A1 | 10/2008 |
| EP | 1435852 B1 | 12/2008 |
| EP | 1498082 B1 | 12/2008 |
| EP | 1707131 B1 | 12/2008 |
| EP | 1997438 A2 | 12/2008 |
| EP | 1477104 B1 | 1/2009 |
| EP | 2014218 A2 | 1/2009 |
| EP | 2042112 A2 | 4/2009 |
| EP | 1832259 B1 | 6/2009 |
| EP | 2074959 A1 | 7/2009 |
| EP | 2106758 A1 | 10/2009 |
| EP | 2111813 A1 | 10/2009 |
| EP | 2200145 A1 | 6/2010 |
| EP | 1214913 B1 | 7/2010 |
| EP | 2238938 A1 | 10/2010 |
| EP | 2298154 A2 | 3/2011 |
| EP | 1510178 B1 | 6/2011 |
| EP | 2305144 A1 | 6/2011 |
| EP | 2335630 A1 | 6/2011 |
| EP | 1502551 B1 | 7/2011 |
| EP | 2361562 A1 | 8/2011 |
| EP | 2365608 A2 | 9/2011 |
| EP | 2422721 A2 | 2/2012 |
| EP | 1927321 B1 | 4/2012 |
| EP | 2510891 A1 | 10/2012 |
| EP | 2316359 B1 | 3/2013 |
| EP | 1586275 B1 | 5/2013 |
| EP | 1616529 B1 | 9/2013 |
| EP | 2583633 B1 | 10/2014 |
| GB | 2032221 A | 4/1980 |
| GB | 2379878 B | 11/2004 |
| GB | 2447767 B | 8/2011 |
| JP | S 50-100891 | 12/1973 |
| JP | S 59-68513 | 10/1982 |
| JP | 62-221343 A | 9/1987 |
| JP | S 62-227343 | 10/1987 |
| JP | 62-292153 A | 12/1987 |
| JP | 63-109386 A | 5/1988 |
| JP | 63-315049 A | 12/1988 |
| JP | H 01-151452 A | 6/1989 |
| JP | H 01-198540 A | 8/1989 |
| JP | 02-71510 U | 5/1990 |
| JP | 2-286149 A | 11/1990 |
| JP | H 02-292193 A | 12/1990 |
| JP | 04-25707 U | 2/1992 |
| JP | 4-30508 U | 3/1992 |
| JP | H 04-150847 A | 5/1992 |
| JP | H 04-152942 A | 5/1992 |
| JP | 05-095955 A | 4/1993 |
| JP | H 06-070938 A | 3/1994 |
| JP | 6-104503 A | 4/1994 |
| JP | 6-507081 A | 8/1994 |
| JP | H 7-508910 A | 10/1995 |
| JP | 7-308323 A | 11/1995 |
| JP | 8-24266 A | 1/1996 |
| JP | 8-275951 A | 10/1996 |
| JP | H 08-299351 A | 11/1996 |
| JP | H 08-336545 A | 12/1996 |
| JP | H 09-503146 A | 3/1997 |
| JP | H 09-135553 A | 5/1997 |
| JP | H 10-005237 A | 1/1998 |
| JP | 10-295700 A | 11/1998 |
| JP | H 11-501543 A | 2/1999 |
| JP | H 11-128238 | 5/1999 |
| JP | H 11-192235 A | 7/1999 |
| JP | 11-253451 A | 9/1999 |
| JP | H 11-318918 A | 11/1999 |
| JP | 2000-041991 A | 2/2000 |
| JP | 2000-070279 A | 3/2000 |
| JP | 2000-210299 A | 8/2000 |
| JP | 2000-287987 A | 10/2000 |
| JP | 2001-029353 A | 2/2001 |
| JP | 2001-502216 A | 2/2001 |

(56) References Cited

FOREIGN PATENT DOCUMENTS

| | | |
|---|---|---|
| JP | 2003612 A | 6/2001 |
| JP | 2001-309925 A | 11/2001 |
| JP | 2002-186901 A | 7/2002 |
| JP | 2002-204808 A | 7/2002 |
| JP | 2002-263579 A | 9/2002 |
| JP | 2002-301086 A | 10/2002 |
| JP | 2002-330977 A | 11/2002 |
| JP | 2002-542690 A | 12/2002 |
| JP | 2003-000612 A | 1/2003 |
| JP | 2003-010201 | 1/2003 |
| JP | 2003-510158 A | 3/2003 |
| JP | 2003-116870 A | 4/2003 |
| JP | 2003-126110 A | 5/2003 |
| JP | 2003-310627 A | 5/2003 |
| JP | 2003-530921 A | 10/2003 |
| JP | 2003-339730 A | 12/2003 |
| JP | 2004-147701 A | 5/2004 |
| JP | 2005027026 A | 1/2005 |
| JP | 2005-040222 A | 2/2005 |
| JP | 2005-066316 A | 3/2005 |
| JP | 2005-074088 A | 3/2005 |
| JP | 2005-534451 A | 11/2005 |
| JP | 2006-6410 A | 1/2006 |
| JP | 2006-512149 A | 4/2006 |
| JP | 2006-116194 A | 5/2006 |
| JP | 2006-158525 A | 6/2006 |
| JP | 2006-217716 A | 8/2006 |
| JP | 2006-218296 A | 8/2006 |
| JP | 2006-288431 A | 10/2006 |
| JP | 2007-050181 A | 3/2007 |
| JP | 2003-126104 A | 5/2007 |
| JP | 2007-229454 A | 9/2007 |
| JP | 2007-527747 A | 10/2007 |
| JP | 2008-508065 A | 3/2008 |
| JP | 2008-119250 A | 5/2008 |
| JP | 2008-521503 A | 6/2008 |
| JP | 2008-212679 A | 9/2008 |
| JP | 2008-284374 A | 11/2008 |
| JP | 2009-511206 A | 3/2009 |
| JP | 2009-517181 A | 4/2009 |
| JP | 4262923 B2 | 5/2009 |
| JP | 2009-523567 A | 6/2009 |
| JP | 2009-236177 | 10/2009 |
| JP | 2010-000336 A | 1/2010 |
| JP | 2010-514923 A | 5/2010 |
| JP | 2010-540186 A | 12/2010 |
| JP | 2012-235658 A | 11/2012 |
| JP | 5208761 B2 | 6/2013 |
| WO | WO 92/22259 A2 | 12/1992 |
| WO | WO 93/08757 A1 | 5/1993 |
| WO | WO 93/14708 A1 | 8/1993 |
| WO | WO 93/16646 A1 | 9/1993 |
| WO | WO 93/20877 A1 | 10/1993 |
| WO | WO 94/21183 A1 | 9/1994 |
| WO | WO 94/24949 A1 | 11/1994 |
| WO | WO 95/09572 A1 | 4/1995 |
| WO | WO 96/30885 A1 | 10/1996 |
| WO | WO 96/39086 A1 | 12/1996 |
| WO | WO 98/16156 A1 | 4/1998 |
| WO | WO 98/26739 A1 | 6/1998 |
| WO | WO 98/35621 A1 | 8/1998 |
| WO | WO 98/37815 A1 | 9/1998 |
| WO | WO 99/20213 A1 | 4/1999 |
| WO | WO 99/52489 A1 | 10/1999 |
| WO | WO 00/64358 A2 | 11/2000 |
| WO | WO 00/74585 A2 | 12/2000 |
| WO | WO 01/54590 A1 | 8/2001 |
| WO | WO 01/67970 A1 | 9/2001 |
| WO | WO 01/95810 A2 | 12/2001 |
| WO | WO 02/24080 A2 | 3/2002 |
| WO | WO 02/38057 A1 | 5/2002 |
| WO | WO 02/062241 A1 | 8/2002 |
| WO | WO 03/082133 A1 | 10/2003 |
| WO | WO 2004/012615 A1 | 2/2004 |
| WO | WO 2004/026104 A2 | 4/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/037095 A2 | 5/2004 |
| WO | WO 2004/098426 A1 | 11/2004 |
| WO | WO 2004/112618 A2 | 12/2004 |
| WO | WO 2005/122917 A1 | 12/2005 |
| WO | WO 2006/012797 A1 | 2/2006 |
| WO | WO 2006/042210 A2 | 4/2006 |
| WO | WO 2006/058223 A2 | 6/2006 |
| WO | WO 2006/063199 A2 | 6/2006 |
| WO | WO 2006/083988 A1 | 8/2006 |
| WO | WO 2006/119139 A2 | 11/2006 |
| WO | WO 2006/119376 A2 | 11/2006 |
| WO | WO 2006/129465 A1 | 12/2006 |
| WO | WO 2007/008703 A2 | 1/2007 |
| WO | WO 2007/008710 A2 | 1/2007 |
| WO | WO 2007/040818 A1 | 4/2007 |
| WO | WO 2007/047380 A2 | 4/2007 |
| WO | WO 2007/047531 A2 | 4/2007 |
| WO | WO 2007/056590 A1 | 5/2007 |
| WO | WO 2007/087272 A2 | 8/2007 |
| WO | WO 2007/143665 A2 | 12/2007 |
| WO | WO 2008/016886 A2 | 2/2008 |
| WO | WO 2008/042021 A1 | 4/2008 |
| WO | WO 2008/049084 A2 | 4/2008 |
| WO | WO 2008/051764 A2 | 5/2008 |
| WO | WO 2008/089174 A2 | 7/2008 |
| WO | WO 2008/118709 A1 | 10/2008 |
| WO | WO 2008/130793 A1 | 10/2008 |
| WO | WO 2009/018406 A2 | 2/2009 |
| WO | WO 2009/027065 A1 | 3/2009 |
| WO | WO 2009/046234 A2 | 4/2009 |
| WO | WO 2009/120992 A2 | 10/2009 |
| WO | WO 2010/068783 A1 | 6/2010 |
| WO | WO 2011/008672 A2 | 1/2011 |
| WO | WO 2011/052939 A2 | 5/2011 |
| WO | WO 2011/100321 A2 | 8/2011 |
| WO | WO 2011/144911 A1 | 11/2011 |
| WO | WO 2012/061722 A2 | 5/2012 |
| WO | WO 2012/128362 A1 | 9/2012 |
| WO | WO 2012/135705 A1 | 10/2012 |
| WO | WO 2012/135721 A1 | 10/2012 |
| WO | WO 2013/018934 A1 | 2/2013 |
| WO | WO 2013/062978 A2 | 5/2013 |

OTHER PUBLICATIONS

*Technology Overview*, Printed from www.harmonicscalpel.com, Internet site, website accessed on Jun. 13, 2007, (3 pages).

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

AST Products, Inc., "Principles of Video Contact Angle Analysis," 20 pages, (2006).

Lim et al., "A Review of Mechanism Used in Laparoscopic Surgical Instruments," Mechanism and Machine Theory, vol. 38, pp. 1133-1147, (2003).

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

Incropera et al., "Fundamentals of Heat and Mass Transfer", Wiley, New York (1990). (Book—not attached).

F. A. Duck, "Optical Properties of Tissue Including Ultraviolet and Infrared Radiation," pp. 43-71 in *Physical Properties of Tissue* (1990).

Orr et al., "Overview of Bioheat Transfer," pp. 367-384 in Optical-Thermal Response of Laser-Irradiated Tissue, A. J. Welch and M. J. C. van Gemert, eds., Plenum, New York (1995).

Campbell et al, "Thermal Imaging in Surgery," p. 19-3, in *Medical Infrared Imaging*, N. A. Diakides and J. D. Bronzino, Eds. (2008).

(56) References Cited

OTHER PUBLICATIONS

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

Sullivan, "Optimal Choice for Number of Strands in a Litz-Wire Transformer Winding," IEEE Transactions on Power Electronics, vol. 14, No. 2, Mar. 1999, pp. 283-291.

Graff, K.F., "Elastic Wave Propagation in a Curved Sonic Transmission Line," IEEE Transactions on Sonics and Ultrasonics, SU-17(1), 1-6 (1970).

Makarov, S. N., Ochmann, M., Desiner, K., "The longitudinal vibration response of a curved fiber used for laser ultrasound surgical therapy," Journal of the Acoustical Society of America 102, 1191-1199 (1997).

Morley, L. S. D., "Elastic Waves in a Naturally Curved Rod," Quarterly Journal of Mechanics and Applied Mathematics, 14: 155-172 (1961).

Walsh, S. J., White, R. G., "Vibrational Power Transmission in Curved Beams," Journal of Sound and Vibration, 233(3), 455-488 (2000).

Covidien 501(k) Summary Sonicision, dated Feb. 24, 2011 (7 pages).

Gerhard, Glen C., "Surgical Electrotechnology: Quo Vadis?," Biomedical Engineering, IEEE Transactions on , vol. BME-31, No. 12, pp. 787, 792, Dec. 1984.

Fowler, K.R., "A programmable, arbitrary waveform electrosurgical device," Engineering in Medicine and Biology Society, 1988. Proceedings of the Annual International Conference of the IEEE, vol., No., pp. 1324, 1325 vol. 3, Nov. 4-7, 1988.

LaCourse, J.R.; Vogt, M.C.; Miller, W.T., III; Selikowitz, S.M., "Spectral analysis interpretation of electro-surgical generator nerve and muscle stimulation," Biomedical Engineering, IEEE Transactions on , vol. 35, No. 7, pp. 505, 509, Jul. 1988.

U.S. Appl. No. 13/751,680, filed Jan. 28, 2013.

\* cited by examiner

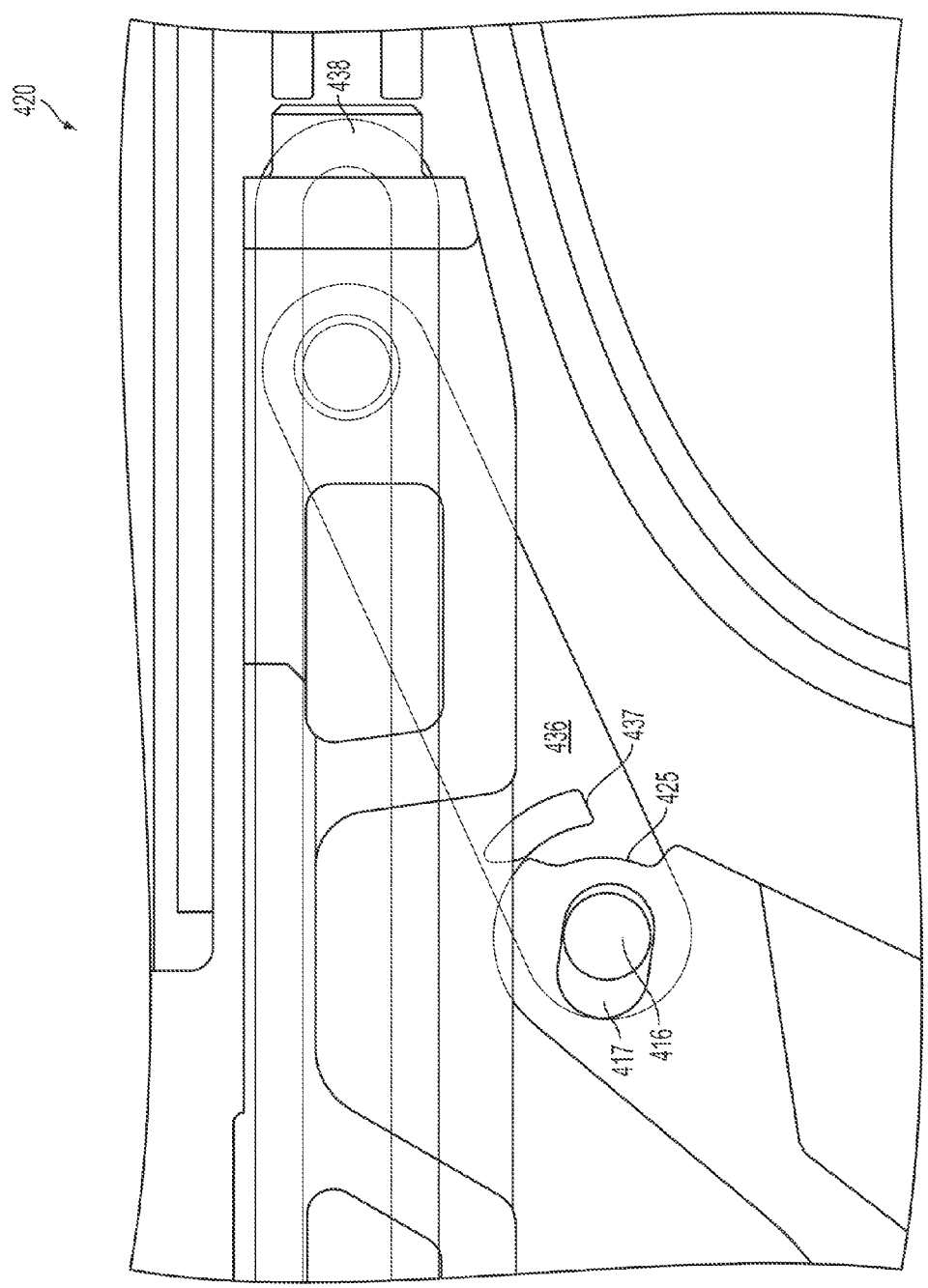

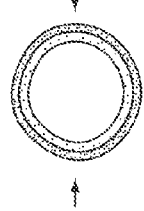
FIG. 17A                FIG. 17E
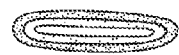
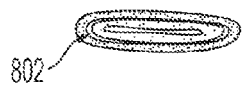
FIG. 17B                FIG. 17F
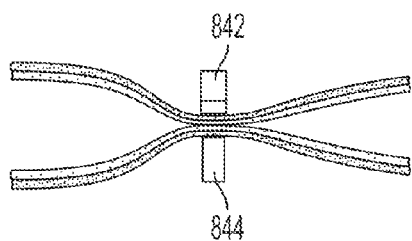
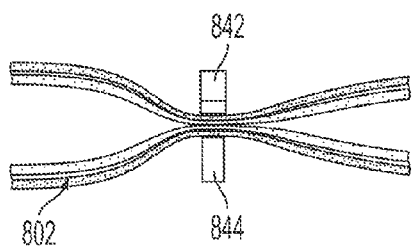
FIG. 17C                FIG. 17G
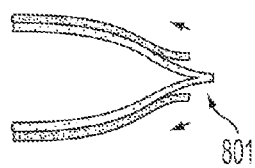
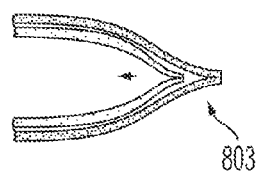
FIG. 17D                FIG. 17H

SURGICAL INSTRUMENT WITH MULTIPLE CLAMPING MECHANISMS

BACKGROUND

1. Field of the Invention

The present application generally relates to medical devices and methods, and in particular, surgical instruments configured to weld and/or incise tissue.

2. Description of the Related Art

In various circumstances, a surgical instrument can be configured to apply energy to tissue in order to treat and/or destroy the tissue. In certain circumstances, a surgical instrument can comprise one or more electrodes which can be positioned against and/or positioned relative to the tissue such that electrical current can flow through the electrodes and into the tissue. The surgical instrument can further comprise an electrical input, a supply conductor electrically coupled with the electrodes, and/or a return conductor which can be configured to allow current to flow from the electrical input, through the supply conductor, through the electrodes and tissue, and then through the return conductor to an electrical output, for example. In various circumstances, the energy can generate heat within the captured tissue to create one or more hemostatic seals within the tissue. Such embodiments may be particularly useful for sealing blood vessels, for example. The surgical instrument can comprise an ultrasonic blade, connected to an ultrasonic transducer, to couple mechanical vibration to tissue and create one or more hemostatic seals and divide the tissue simultaneously. Such embodiments may be particularly useful for sealing and dividing blood vessels, for example. Furthermore, other energy modalities may be contemplated, but not limited to, microwave, laser, thermal, and high intensity focused ultrasound. The surgical instrument can further comprise a cutting member which can be moved relative to the tissue and electrodes in order to transect the tissue.

The foregoing discussion is intended only to illustrate various aspects of the related art in the field of the invention at the time, and should not be taken as a disavowal of claim scope.

SUMMARY

In various embodiments, a surgical instrument may generally comprise a shaft comprising a proximal end and a distal end; an end effector extending from the distal end of the shaft, wherein the end effector is operable to grasp tissue; a handle extending from the proximal end, wherein the handle comprises a gripping portion; and a trigger assembly extending from the handle, wherein the trigger assembly comprises a trigger movable relative to the gripping portion between an unactuated position and a first actuated position and a second actuated position, wherein the trigger is operable to control the end effector to selectively grasp tissue at a first compressive force when the trigger is in the first actuated position and a second compressive force when the trigger is in the second actuated position.

In various embodiments, a surgical instrument may generally comprise a shaft comprising a proximal end and a distal end; an end effector extending from the distal end of the shaft, wherein the end effector comprises a first jaw, a second jaw, and an electrode, wherein the first jaw is movable relative to the second jaw between an open position and a closed position to compress tissue intermediate the first jaw and second jaw when in the closed position; a handle extending from the proximal end, wherein the handle comprises a gripping portion; and a trigger assembly extending from the handle, wherein the trigger assembly comprises a trigger movable relative to the gripping portion through a first range of motion from an unactuated position to a first actuated position, wherein the trigger is movable through a second range of motion from first actuated position to a second actuated position, and wherein the trigger is movable thorough a third range of motion from the second actuated position to the unactuated position, wherein the trigger is operable to control the end effector to selectively compress tissue at a first compressive force when the trigger is in the first actuated position and a second compressive force when the trigger is in the second actuated position, wherein the first compressive force is greater than the second compressive force.

In various embodiments, a surgical instrument may generally comprise a shaft comprising a proximal end and a distal end; an ultrasonic waveguide at least partially positioned within the shaft, the waveguide having a proximal end and a distal end; an ultrasonically actuated blade positioned at the distal end of the waveguide; a clamp arm assembly pivotally connected to the distal end of the shaft, wherein the clamp arm assembly comprises at least two camming members rotationally attached to a clamp arm, wherein the clamp arm is movable between an open position and a closed position relative to the blade to compress tissue intermediate the clamp arm and blade when in the closed position, and wherein the at least two camming members rotate relative to the clamp arm to separate tissue layers when the clamp arm moves between the open position and a closed position.

BRIEF DESCRIPTION OF THE FIGURES

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

FIGS. 10A-D include a surgical instrument comprising a trigger assembly in various positions according to various embodiments.

FIGS. 17A-H include cross-sectional views of a portion of a vessel subjected to a compressive force according to various embodiments.

DETAILED DESCRIPTION

Figure 1:
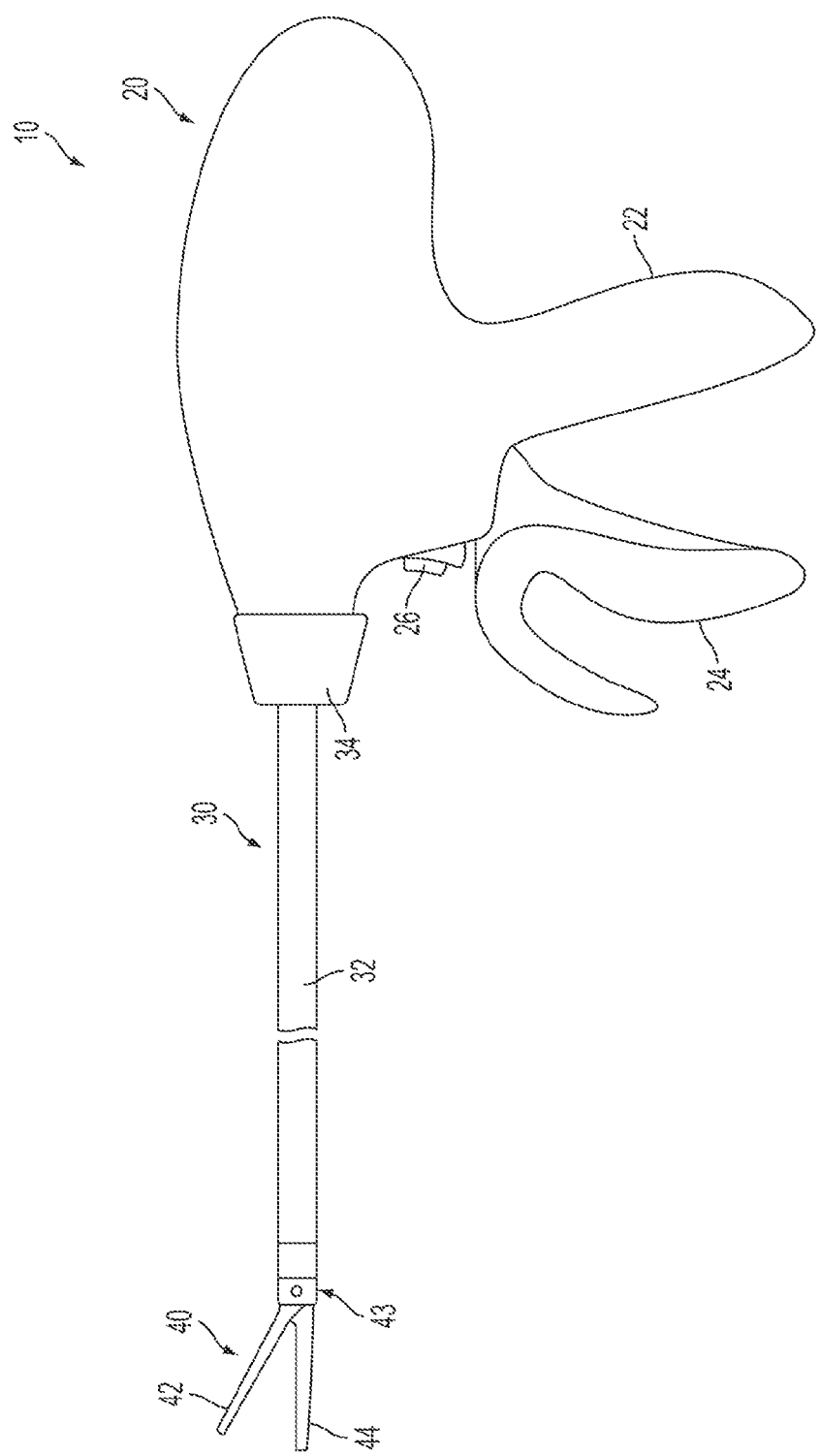
FIG. 1 includes a side elevational view of a surgical instrument according to various embodiments.

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Various embodiments of systems and methods relate to creating thermal "welds" or "fusion" within native tissue volumes. The alternative terms of tissue "welding" and tissue "fusion" may be used interchangeably herein to describe thermal treatments of a targeted tissue volume that result in a substantially uniform fused-together tissue mass, for example, in welding blood vessels that exhibit substantial burst strength immediately post-treatment. The strength of such welds is particularly useful for (i) permanently sealing blood vessels in vessel transection procedures; (ii) welding organ margins in resection procedures; (iii) welding other anatomic ducts wherein permanent closure is required; and also (iv) for performing vessel anastomosis, vessel closure or other procedures that join together anatomic structures or portions thereof. The welding or fusion of tissue as disclosed herein is to be distinguished from "coagulation", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the treated tissue.

At the molecular level, the phenomena of truly "welding" tissue as disclosed herein may result from the thermally-induced denaturation of collagen and other protein molecules in a targeted tissue volume to create a transient liquid or gel-like proteinaceous amalgam. A selected energy density is provided in the targeted tissue to cause hydrothermal breakdown of intra- and intermolecular hydrogen crosslinks in collagen and other proteins. The denatured amalgam is maintained at a selected level of hydration—without desiccation—for a selected time interval which can be very brief. The targeted tissue volume is maintained under a selected very high level of mechanical compression to insure that the unwound strands of the denatured proteins are in close proximity to allow their intertwining and entanglement. Upon thermal relaxation, the intermixed amalgam results in protein entanglement as re-crosslinking or renaturation occurs to thereby cause a uniform fused-together mass.

Ultrasonic surgical instruments are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and hemostasis by coagulation, desirably minimizing patient trauma. The cutting action is typically effected by an end effector or blade tip at the distal end of the instrument, which transmits ultrasonic energy to tissue brought into contact with the end effector. Ultrasonic instruments of this nature can be configured for open surgical use, laparoscopic or endoscopic surgical procedures including robotic-assisted procedures.

Ultrasonic surgical instruments have been developed that include a clamp mechanism to press tissue against the blade of the end effector in order to couple ultrasonic energy to the tissue of a patient. Such an arrangement (sometimes referred to as a clamp coagulator shears or an ultrasonic transector) is disclosed in U.S. Pat. Nos. 5,322,055, 5,873,873, and 6,325,811, all of which are incorporated herein by reference in their entireties. The surgeon activates the clamp arm to press the clamp pad against the blade by squeezing on the handgrip or handle.

Some current ultrasonic shears devices utilize tissue engaging pads or clamp pads that close in parallel with the surface of the blade. By this construction, tissue is grasped between the clamp pad and the blade. The clamp pad may comprise a low coefficient of friction polymer material, or any other suitable low-friction material. Although these designs have been adequate, they tend to suffer from longevity issues since the clamp pads tend to deteriorate over long surgical procedures. Additionally, newer designs of clamp coagulator shears increase blade amplitude and/or the loading of the clamp pad against the tissue and blade and overwhelm the clamp pad material, resulting in less than required clamp pad life. The clamp pad material limits the amount of force that may be applied against the tissue and blade, which in turn limits the tissue thickness or vessel size that some current clamp coagulator shears may effectively cut and coagulate.

It would be desirable to provide electrosurgical instruments that overcome some of the deficiencies of current ultrasonic surgical instruments. Various embodiments of the electrosurgical instruments described herein may overcome some of those deficiencies.

Enhancing the ability to seal vessels may be accomplished by placing the adventitial layers of the opposing sides of a coapted vessel in direct contact with each other. Preventing this direct contact is commonly the muscular (entima) layer of the vessel. The muscular layers may be "split" within a vessel without compromising the adventitia by applying a sufficient compressive force. The muscular layers may retract enough to allow direct adventitial contact. The direct adventitial seals demonstrate higher burst pressures. In various embodiments, an electrosurgical device may provide variable force control to allow the user to create a large compressive force for muscle separation and a smaller compressive force for application of ultrasonic energy and sealing and cutting.

In various embodiments, electrosurgical instruments may be configured to provide multiple trigger positions to deliver multiple levels of compressive force to the tissue. The compressive force may be generally established by a handle using one of two user-selectable clamping modes to provide variable force control: one for cutting and coagulating small blood vessels; and one for cutting and coagulating large blood vessels. The large vessel coagulating mode generally corresponds to a sequence where the end effector delivers a short-term high compressive force and then progresses to a position of lesser compressive force. For example, in various embodiments, the lesser compressive force may be about 50% to about 70% of the high compressive force. The high compressive force may compress a large vessel such that the inner layers of the vessel, i.e., the tunica intima and tunica media, are extruded and separated and only the outer layer of the vessel, i.e., the tunica adventitia, resides within the end effector.

Without wishing to be bound to any particular theory, it is believed that the adventitia contributes most significantly to the seal strength of an ultrasonically transected vessel, and the inner layers of the vessel contribute very little to the seal strength and, in fact, tend to flatten and structurally counteract the adventitia seal. Accordingly, electrosurgical instruments may be configured to provide a high compressive force to mechanically extrude the inner layers of the vessel and a low compressive force to allow direct adventitial contact and an adventitia-to-adventitia seal. Various embodiments of electrosurgical instruments described herein may provide certain advantages over current ultrasonic shears devices, including one or more of the following: obtaining a seal at a more manageable, lower clamping force; obtaining a seal at a lower generator drive power; lower generator power requirements; utilizing less durable clamp pad materials; improved large vessel sealing; improved clamp pad life; improved ergonomics by only using the high clamp force, which corresponds to high input force, when required; improved efficiency; and improved cost savings.

An electrosurgical instruments can be configured to supply energy, such as electrical energy, ultrasonic energy, and/or heat energy, for example, to the tissue of a patient. For example, various embodiments disclosed herein provide electrosurgical jaw structures adapted for transecting captured tissue between the jaws and for contemporaneously welding or sealing the captured tissue margins with controlled application of RF energy. In various embodiments, the electrosurgical jaw structures may be adapted to coagulate the captured tissues rather than weld the captured tissue. Electrosurgical instruments may also be configured to, for example, grasp, sever, and staple tissue. Electrosurgical instruments may be configured to supply other energy modalities and/or combinations thereof, such as, for example, microwave, laser, thermal, ultrasonic and high intensity focused ultrasound. All such arrangements and implementations are intended to be within the scope of this disclosure.

In various embodiments, referring to FIG. 1, an electrosurgical instrument 10 may comprise a hand piece 20, a shaft 30 extending distally from hand piece 20, and an end effector 40 disposed at a distal end of shaft 30. Hand piece 20 may comprise a pistol grip 22, a pivoting trigger 24, and an activation button 26. Trigger 24 may be pivotable toward and away from pistol grip 22 to selectively actuate end effector 40 as will be described in greater detail below. Activation button 26 may be operable to selectively activate RF circuitry that is in communication with end effector 40, as will also be described in greater detail below. In some versions, activation button 26 may also serve as a mechanical lockout against trigger 24, such that trigger 24 cannot be fully actuated unless button 26 is being pressed simultaneously. Examples of how such a lockout may be provided are disclosed in one or more of the references cited herein. It should be understood that pistol grip 22, trigger 24, and button 26 may be modified, substituted, supplemented, etc. in any suitable way, and that the descriptions of such components herein are merely illustrative.

Shaft 30 may comprise any suitable cross-section, such as, for example, a cylindrical cross-section and/or rectangular cross-section. Shaft 30 may comprise an outer sheath 32 that extends from the hand piece 20. A proximal end of shaft 30 may be attached to the hand piece 20. In various embodiments, shaft 30 may be rotatable about the longitudinal axis defined by sheath 32, relative to hand piece 20 via a knob 34.

Such rotation may provide rotation of end effector 40 and shaft 30 unitarily. In various embodiments, knob 34 may be operable to rotate end effector 40 without rotating any portion of shaft 30.

In various embodiments, end effector 40 may comprise a first jaw 42 and a second jaw 44. Second jaw 44 may be substantially fixed relative to shaft 30; while first jaw 42 may pivot relative to shaft 30, toward and away from second jaw 42. In various embodiments, actuators, such as, for example, rods and cables, may extend through sheath 32 and be joined with first jaw 42 at a pivotal coupling 43 such that longitudinal movement of the actuator through shaft 30 provides pivoting of first jaw 42 relative to shaft 30 and relative to second jaw 44. In various embodiments, jaws 42, 44 may comprise any other suitable kind of movement and may be actuated in any other suitable fashion. For example, as will be described in greater detail below, jaws 42, 44 may be actuated and thus closed by longitudinal translation of a firing beam 60 such that actuators may simply be eliminated in certain embodiments.

Figure 2:
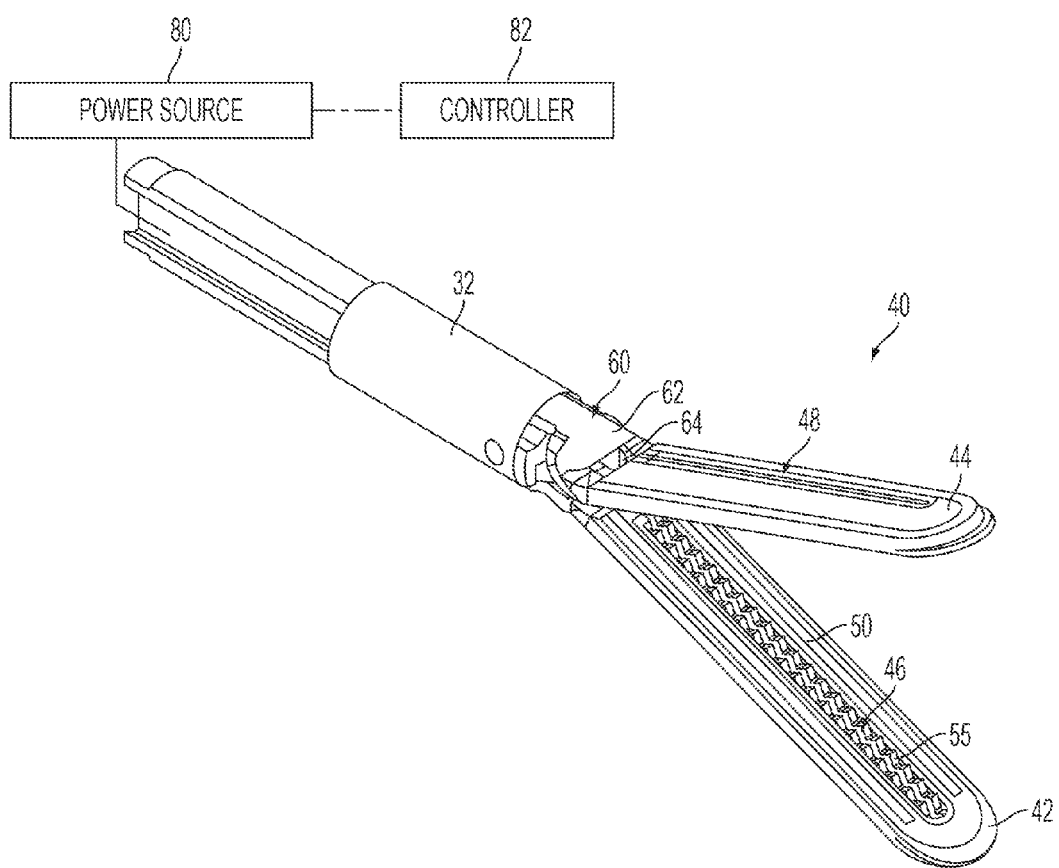
FIG. 2 includes a perspective view of the end effector of the device of FIG. 1, in an open configuration according to various embodiments.
Figure 3:
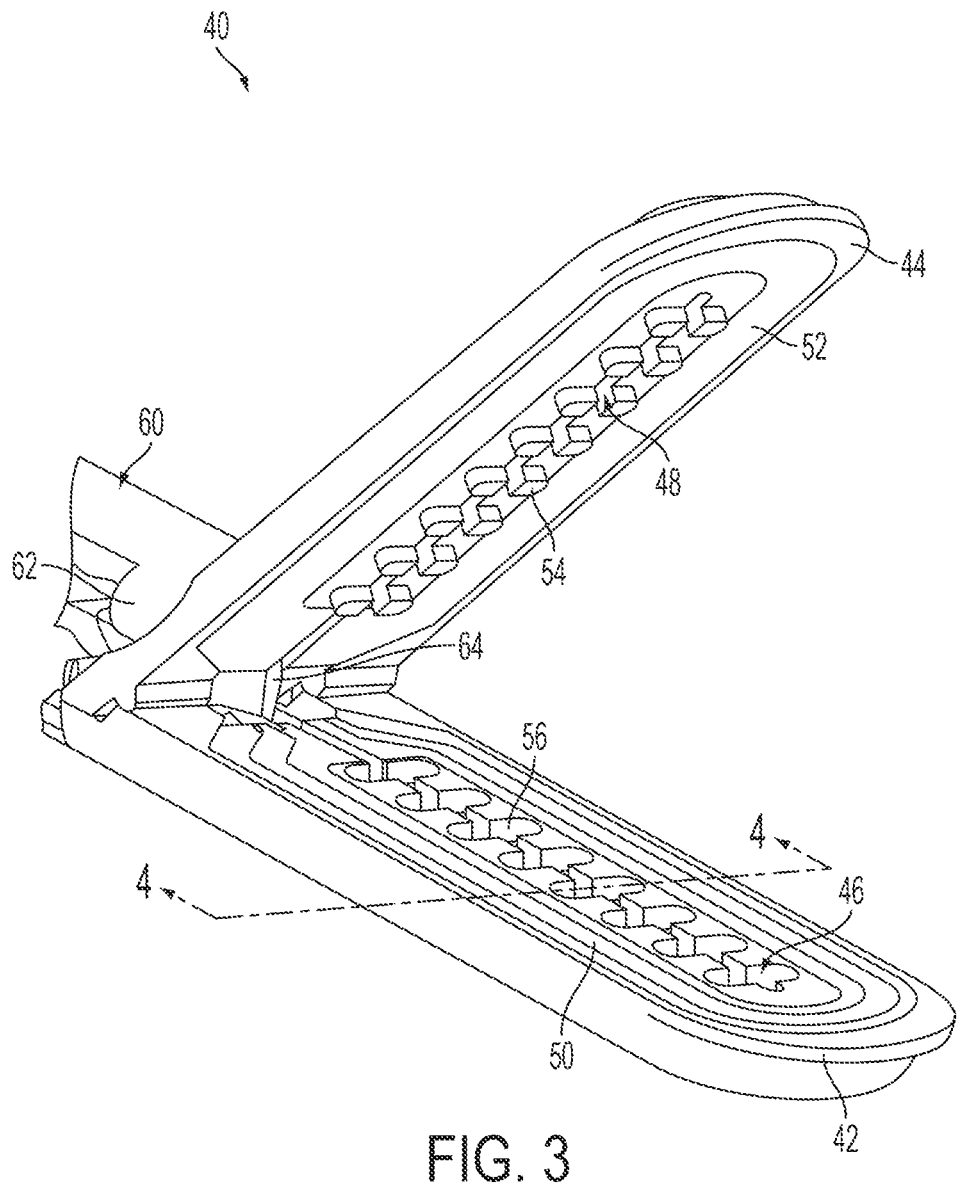
FIG. 3 includes another perspective view of the end effector of the device of FIG. 1, in an open configuration according to various embodiments.
Figure 4:
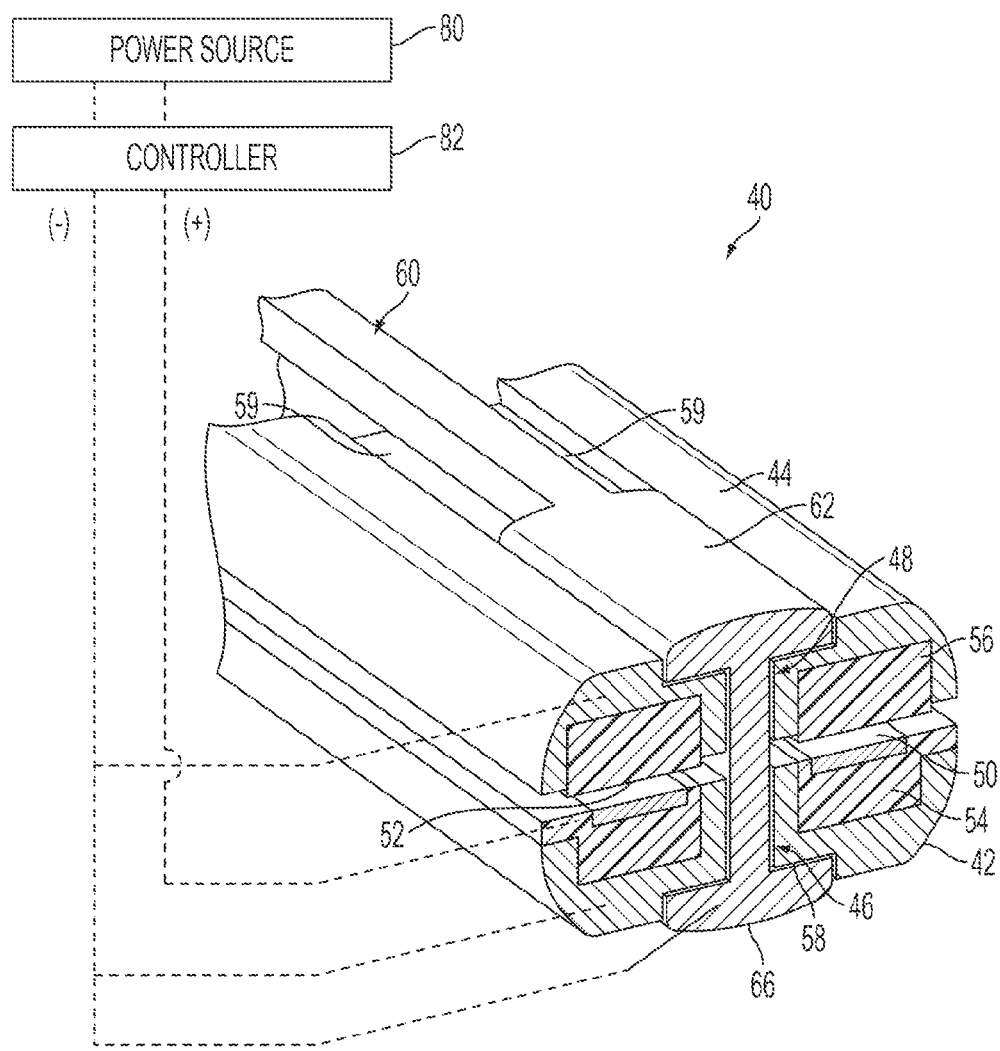
FIG. 4 includes a cross-sectional end view of the end effector of FIG. 2, in a closed configuration and with the blade in a distal position according to various embodiments.

In various embodiments, referring to FIGS. 2-4, first jaw 42 defines a longitudinally extending elongate slot 46 and second jaw 44 defines a longitudinally extending elongate slot 48. The top side of first jaw 42 may comprise a first electrode surface 50 and the underside of second jaw 44 may comprise a second electrode surface 52. Electrode surfaces 50, 52 may be in communication with an electrical source 80 via one or more conductors (not shown) that extend along the length of shaft 30. Electrical source 80 may be operable to deliver RF energy to first electrode surface 50 at a first polarity and to second electrode surface 52 at a second (opposite) polarity, such that RF current flows between electrode surfaces 50, 52 and thereby through tissue captured between jaws 42, 44. In various embodiments, firing beam 60 may serve as an electrical conductor that cooperates with electrode surfaces 50, 52, e.g., as a ground return for delivery of bipolar RF energy captured between jaws 42, 44. Electrical source 80 may be external to electrosurgical instrument 10 or may be integral with electrosurgical instrument 10, e.g., in hand piece 20. A controller 82 may regulate delivery of power from electrical source 80 to electrode surfaces 50, 52. Controller 82 may be external to electrosurgical instrument 10 or may be integral with electrosurgical instrument 10, e.g., in hand piece 20. It should also be understood that electrode surfaces 50, 52 may be provided in a variety of alternative locations, configurations, and relationships.

Referring to FIG. 4, the lower side of first jaw 42 may comprise a longitudinally extending recess 58 adjacent to slot 46 and the upper side of second jaw 44 may comprise a longitudinally extending recess 58 adjacent to slot 48. FIG. 2 shows the upper side of first jaw 42 including a plurality of teeth serrations 46. It should be understood that the lower side of second jaw 44 may include complementary serrations that nest with serrations 46 to enhance gripping of tissue captured between jaws 42, 44 without necessarily tearing the tissue. FIG. 3 shows an example of serrations 46 in first jaw 42 as mainly recesses; with serrations 48 in second jaw 44 as mainly protrusions. Of course, serrations 46, 48 may take any other suitable form or may be simply omitted altogether. It should also be understood that serrations 46, 48 may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws 42, 44.

When jaws 42, 44 are in a closed position, shaft 30 and end effector 40 may be sized and configured to fit through trocars having various inner diameters, such that electrosurgical instrument 10 may be usable in minimally invasive surgery, though of course electrosurgical instrument 10 could also be used in open and endoscopic procedures if desired. By way of example only, shaft 30 and end effector 40 may present an outer diameter of approximately 5 mm when jaws 42, 44 are in a closed position. Alternatively, shaft 30 and end effector 40 may present any other suitable outer diameter, such as, for example, from about 2 mm to about 20 mm.

In various embodiments, either jaw 42, 44 or both of jaws 42, 44 may include at least one port, passageway, conduit, and/or other feature that is operable to draw steam, smoke, and/or other gases from the surgical site. Such a feature may be in communication with a source of suction, such as, for example, an external source or a source within hand piece 20. In addition, end effector 40 may comprise one or more tissue cooling features (not shown) that reduce the degree or extent of thermal spread caused by end effector 40 on adjacent tissue when electrode surfaces 50, 52 are activated. Various suitable forms that such cooling features may take will be apparent to those of ordinary skill in the art in view of the teachings herein.

In various embodiments, end effector 40 may comprise one or more sensors (not shown) that are configured to sense a variety of parameters at end effector 40, including but not limited to, jaw position, temperature of adjacent tissue, electrical resistance or impedance of adjacent tissue, voltage across adjacent tissue, forces exerted on jaws 42, 44 by adjacent tissue. In various embodiments, end effector 40 may include one or more positive temperature coefficient (PTC) thermistor bodies 54, 56, e.g., a PTC polymer, located adjacent to electrodes 50, 52 and/or elsewhere. Data from sensors may be communicated to controller 82. Controller 82 may process such data in a variety of ways. In various embodiments, controller 82 may modulate or otherwise change the RF energy being delivered to electrode surfaces 50, 52, based at least in part on data acquired from one or more sensors at end effector 40. In various embodiments, controller 82 may alert the user to one or more conditions via an audio and/or visual feedback device, e.g., speaker, lights, display screen, etc., based at least in part on data acquired from one or more sensors at end effector 40. It should also be understood that some kinds of sensors need not necessarily be in communication with controller 82, and may simply provide a purely localized effect at end effector 40. In various embodiments, PTC thermistor bodies 54, 56 at end effector 40 may automatically reduce the energy delivery at electrode surfaces 50, 52 as the temperature of the tissue and/or end effector 40 increases, thereby reducing the likelihood of overheating. In various embodiments, a PTC thermistor element may be in series with power source 80 and electrode surface 50, 52; and the PTC thermistor may provide an increased impedance to reduce flow of current in response to temperatures exceeding a threshold. Furthermore, it should be understood that electrode surfaces 50, 52 may be used as sensors, e.g., to sense tissue impedance. Various kinds of sensors that may be incorporated into electrosurgical instrument 10 will be apparent to those of ordinary skill in the art in view of the teachings herein. Similarly various things that can be done with data from sensors, by controller 82 or otherwise, will be apparent to those of ordinary skill in the art in view of the teachings herein. Other suitable variations for end effector 40 will also be apparent to those of ordinary skill in the art in view of the teachings herein.

Figure 4A:
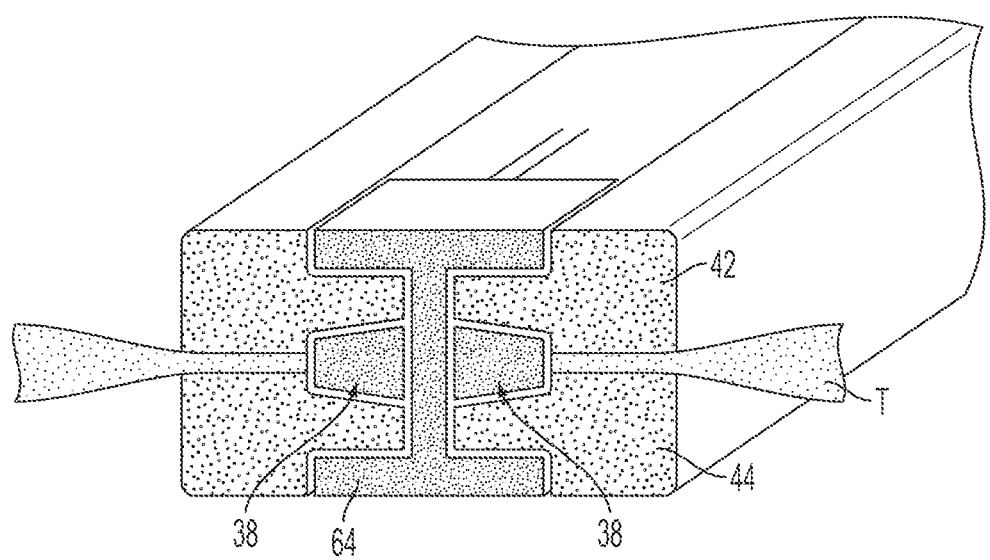
FIG. 4A includes a surgical instrument comprising an end effector comprising roller bearings according to various embodiments.

In various embodiments, referring to FIGS. 2-4, electrosurgical instrument may comprise a firing beam 60 that is longitudinally movable along part of the length of end effector 40. Firing beam 60 may be coaxially positioned within shaft 30, extends along the length of shaft 30, and translates longitudinally within shaft 30, though it should be understood that firing beam 60 and shaft 30 may have any other suitable relationship. Firing beam 60 may comprise a sharp distal blade 64, an upper flange 62, and a lower flange 66. As illustrated in FIG. 4, distal blade 64 extends through slots 46, 48 of jaws 42, 44, with upper flange 62 being located above jaw 44 in recess 59 and lower flange 66 being located below jaw 42 in recess 58. The configuration of distal blade 64 and flanges 62, 66 provides an "I-beam" type of cross section at the distal end of firing beam 60. In various embodiments, flanges 62, 66 may extend longitudinally along any suitable length of firing beam 60. In various embodiments, flanges 62, 66 may be positioned along the exterior of jaws 42, 44, or disposed in corresponding slots formed within jaws 42, 44. For example, each jaw 42, 44 may define a "T"-shaped slot, with portions of distal blade 64 being disposed in one vertical portion of each "T"-shaped slot and with flanges 62, 66 being disposed in the horizontal portions of the "T"-shaped slots. Referring to FIG. 4A, in various embodiments, distal blade 64 may comprise at least one roller bearing 38 to compress tissue T and/or fracture calcium formed within or externally to the vessel. Roller bearing 38 may comprise a conical cylinder have a decreasing diameter laterally away from distal blade 64, as shown in FIG. 4A. In various embodiments, roller bearing 38 may comprise a conical cylinder have a increasing diameter laterally away from distal blade 64. In various embodiments, roller bearing 38 may comprise a straight cylinder. In various embodiments, roller bearing 38 may comprise a curved cross-sectional shape, such as, for example, a circle and an ellipse. As shown in FIG. 4A, roller bearings 38 may be positioned on opposing sides of distal blade 64 intermediate jaws 42, 44. In various embodiments, distal blade 64 may comprise a pin (not shown) to rotate roller bearing 38 relative to distal blade 64. In various embodiments, distal blade may comprise a vertical slot including a pin slideably disposed in the vertical slot to rotate roller bearing 38 and/or move roller bearing 38 perpendicularly relative to distal blade 64 Various other suitable configurations and relationships will be apparent to those of ordinary skill in the art in view of the teachings herein.

Distal blade 64 may be substantially sharp, such that distal blade 64 may readily sever tissue that is captured between jaws 42, 44. Distal blade 64 may be electrically grounded to provide a return path for RF energy as described elsewhere herein. In various embodiments, distal blade 64 may serve as an active electrode. In various embodiments, distal blade 64 may be selectively energized with ultrasonic energy, such as, for example, harmonic vibrations at about 55.5 kHz.

In various embodiments, the "I-beam" type of configuration of firing beam 60 may provide closure of jaws 42, 44 as firing beam 60 is advanced distally. In particular, flange 62 urges jaw 44 pivotally toward jaw 42 as firing beam 60 is advanced from a proximal position, as shown in FIGS. 1-3, to a distal position, as shown in FIG. 4, by bearing against recess 59 formed in jaw 44. This closing effect on jaws 42, 44 by firing beam 60 may occur before distal blade 64 reaches tissue captured between jaws 42, 44. Such staging of encounters by firing beam 60 may reduce the force required to squeeze grip 24 to actuate firing beam 60 through a full firing stroke. In other words, in various embodiments, firing beam 60 may have already overcome an initial resistance required to substantially close jaws 42, 44 on tissue before encountering resistance from severing the tissue captured between jaws 42, 44. Of course, any other suitable staging may be provided.

In various embodiments, flange 62 may be configured to cam against a ramp feature at the proximal end of jaw 44 to open jaw 42 when firing beam 60 is retracted to a proximal position and to hold jaw 42 open when firing beam 60 remains at the proximal position. This camming capability may facilitate use of end effector 40 to separate layers of tissue, to perform blunt dissections, etc., by forcing jaws 42, 44 apart from a closed position. In various embodiments, jaws 42, 44 may be resiliently biased to an open position by a spring or other type of resilient feature. While jaws 42, 44 close or open as firing beam 60 is translated, it should be understood that other embodiments may provide independent movement of jaws 42, 44 and firing beam 60. In various embodiments, one or more cables, rods, beams, or other features may extend through shaft 30 to selectively actuate jaws 42, 44 independently of firing beam 60. Such jaw 42, 44 actuation features may be separately controlled by a dedicated feature of hand piece 20. In various embodiments, such jaw actuation features may be controlled by trigger 24 in addition to having trigger 24 control firing beam 60. It should also be understood that firing beam 60 may be resiliently biased to a proximal position, such that firing beam 60 retracts proximally when a user relaxes their grip on trigger 24.

In various embodiments, in use, end effector 40 may be inserted into a patient via a trocar to a desired position and orientation relative to an anatomical structure within the patient. Two layers of tissue of the anatomical structure are then captured between jaws 42, 44 by squeezing trigger 24 toward pistol grip 22. Such layers of tissue may be part of the same natural lumen defining anatomical structure, such as, for example, blood vessel, portion of gastrointestinal tract, portion of reproductive system, etc., in a patient. In various embodiments, one tissue layer may comprise the top portion of a blood vessel and the other tissue layer may comprise the bottom portion of the blood vessel, along the same region of length of the blood vessel. In various embodiments, the fluid path through the blood vessel before use of electrosurgical instrument 10 may be perpendicular to the longitudinal axis defined by end effector 40. The lengths of jaws 42, 44 may be oriented perpendicular to or at least generally transverse to the length of the blood vessel. As described above, flanges 62, 66 cammingly act to pivot jaw 44 toward jaw 42 when firing beam 60 is actuated distally by squeezing trigger 24 toward pistol grip 22.

In various embodiments, with tissue layers captured between jaws 42, 44, firing beam 60 may continue to advance distally by the user squeezing trigger 24 toward pistol grip 22. As firing beam 60 advances distally, distal blade 64 simultaneously severs the clamped tissue layers, resulting in separated upper layer portions being apposed with respective separated lower layer portions. This results in a blood vessel being cut in a direction that is generally transverse to the length of the blood vessel. It should be understood that the presence of flanges 62, 66 immediately above and below jaws 42, 44, respectively, may help keep jaws 42, 44 in a closed and tightly clamping position. In particular, flanges 62, 66 may help maintain a significantly compressive force between jaws 42, 44. With severed tissue layer portions being compressed between jaws 42, 44, electrode surfaces 50, 52 may be activated with bipolar RF energy by the user depressing activation button 26. In various embodiments, electrodes 50, 52 may be selectively coupled with power source 80, for example by the user depressing button 26, such that electrode surfaces 50, 52 of jaws 42, 44 are activated with a common first polarity while firing beam 60 is activated at a second polarity that is opposite to the first polarity. Thus, a bipolar RF current flows between firing beam 60 and electrode surfaces 50, 52 of jaws 42, 44 through the compressed regions of severed tissue layer portions. In various embodiments, electrode surface 50 has one polarity while electrode surface 52 and firing beam 60 both have the other polarity. Bipolar RF energy may be delivered by power source 80 to thermally weld the tissue layer portions on one side of firing beam 60 together and the tissue layer portions on the other side of firing beam 60 together.

In certain circumstances, the heat generated by activated electrode surfaces 50, 52 can denature the collagen within the tissue layer portions and, in cooperation with compressive force provided by jaws 42, 44, the denatured collagen can form a seal within the tissue layer portions. Thus, the severed ends of the natural lumen defining anatomical structure are hemostatically sealed shut, such that the severed ends will not leak bodily fluids. In various embodiments, electrode surfaces 50, 52 may be activated with bipolar RF energy before firing beam 60 begins to translate distally and thus before the tissue is even severed. For example, such timing may be provided in versions where button 26 serves as a mechanical lockout relative to trigger 24 in addition to serving as a switch between power source 80 and electrode surfaces 50, 52.

While several of the teachings below are described as variations to electrosurgical instrument 10, it should be understood that various teachings below may also be incorporated into various other types of devices. By way of example only, in addition to being readily incorporated into electrosurgical instrument 10, various teachings below may be readily incorporated into the devices taught in any of the references cited herein, other types of electrosurgical devices, alternative energy modality devices, surgical staplers, surgical clip appliers, and tissue graspers, among various other devices. Other suitable devices into which the following teachings may be incorporated will be apparent to those of ordinary skill in the art in view of the teachings herein.

In various embodiments, the surgical instrument may comprise a two stage clamping mechanism configured to provide a higher clamp force to part the muscular layer of a blood vessel and a lower clamp force to seal across the adventitia. Without wishing to be bound to any particular theory, it is believe that the lower clamp force facilitates the proper heating rate to generate a higher strength seal across the adventitia layers relative to the higher clamp force.

Figure 5:
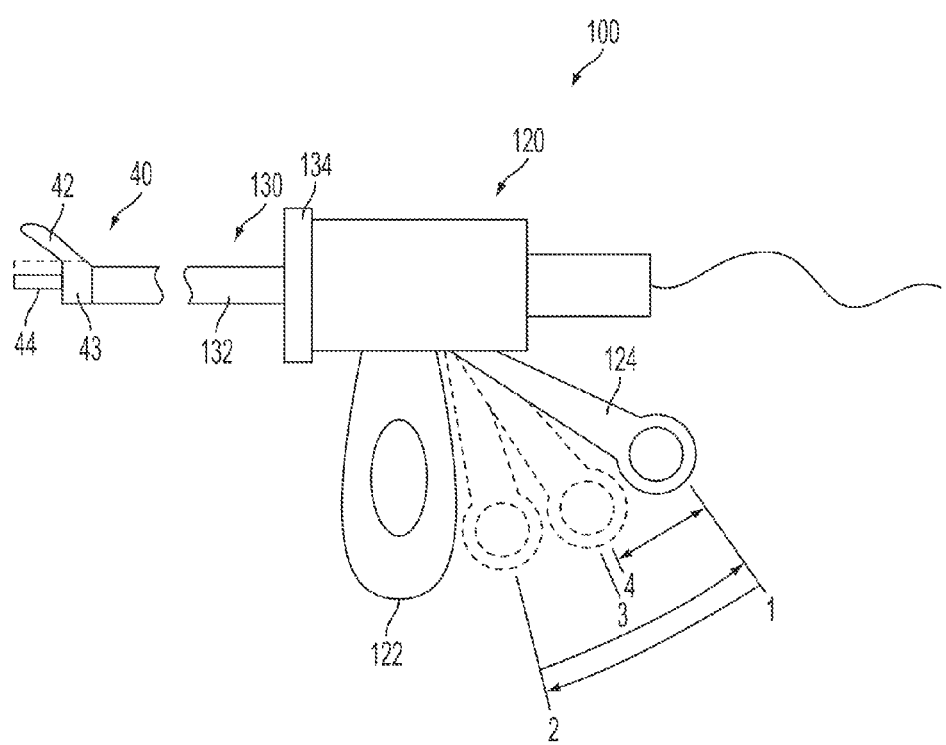
FIG. 5 includes a surgical instrument comprising a trigger assembly in various positions according to various embodiments.

In various embodiments, as shown in FIG. 5, trigger 24 may be movable relative to hand piece 20 between an unactuated position and one or more actuated positions. In various embodiments, trigger 24 is movable through a first range of motion from an unactuated position 1 to a first actuated position 2. In various embodiments, the first range of motion may be from an unactuated position 1 to position 3 and/or position 4, and from position 3 and/or position 4 to first actuated position 2. In various embodiments, trigger 24 is movable through a second range of motion from the first actuated position 2 to a second actuated position 3. In various embodiments, trigger 24 is movable through a third range of motion from the second actuated position 3 to the unactuated position 1. In various embodiments, trigger 24 is movable through a fourth range of motion from the unactuated position 1 to the third actuated position 4. In various embodiments, trigger 24 is movable through a fifth range of motion from the third actuated position 4 to the unactuated position 1. In various embodiments, the second actuated position 3 and third actuated position 4 may be the same or different.

In various embodiments, as described above, jaws 42, 44 may apply compressive force, or coaptation force, to tissue captured therebetween. In various embodiments, jaws 42, 44 may apply a first compressive force when trigger 24 is in the first actuated position 2, a second compressive force when trigger 24 is in the second actuated position 3, and a third compressive force when trigger 24 is in the third actuated position 4. In various embodiments, referring to FIG. 5, jaws 42, 44 may be in a closed position characterized by a first compressive force when trigger 24 is in the first actuated position. In various embodiments, jaws 42, 44 may be in a closed position characterized by a second compressive force when trigger 24 is in the second actuated position. In various embodiments, jaws 42, 44 may be in a closed position characterized by a third compressive force when trigger 24 is in the third actuated position. In various embodiments, jaws 42, 44 may be in an open position when trigger 24 is in the unactuated position.

In various embodiments, the first compressive force, second compressive force, and third compressive force may be different. In various embodiments, the first compressive force may be greater than the second compressive force. In various embodiments, the second compressive force may be greater than or equal to the third compressive force. In various embodiments, the first compressive force, second compressive force, and third compressive force may be individually selected from up to about 10 pounds per square inch ("psi"), such as, for example, about 1 psi to about 10 psi, about 2 psi to about 8 psi, about 3 psi to about 5 psi, and about 4 psi to about 6 psi. In various embodiments, the first compressive force may be about 4 psi to about 6 psi and the second compressive force may be about 2 psi to about 4 psi. In various embodiments, the first compressive force may be about 6 psi and the second compressive force may be about 4 psi. In various embodiments, the first compressive force may be about 4 psi and the second compressive force may be about 2 psi. In various embodiments, the first compressive force may be about 3 psi to about 5 psi and the second compressive force may be about 1 psi to about 3 psi. In various embodiments, the first compressive force may be about 5 psi and the second compressive force may be about 3 psi. In various embodiments, the first compressive force may be about 3 psi and the second compressive force may be about 1 psi. In various embodiments, jaws 42, 44 may not apply compressive force to the tissue when trigger 24 is in the unactuated position.

In various embodiments, electrosurgical instrument 10 may comprise a trigger assembly configured to actuate end effector 40 to provide variable compressive force to tissue captured between jaws 42, 44 when trigger 24 is in the first actuated position, second actuated position, and/or third actuated position, as described in greater detail below. In various embodiments, the trigger assembly may be configured to limit the compressive force to a first compressive force when trigger 24 is in the first actuated position and limit the compressive force to a second compressive force when trigger 24 is in the second actuated position. In various embodiments, the trigger assembly may be configured to limit the compressive force to a third compressive force when trigger 24 is in the third actuated position.

In various embodiments, electrosurgical instrument 10 may comprise a trigger assembly configured to actuate end effector 40 to provide variable compressive force to tissue captured between jaws 42, 44 through the first range of motion, second range of motion, and/or third range of motion, as described in greater detail below. In various embodiments, the trigger assembly may be configured to limit the compressive force to a first compressive force through the first range of motion and limit the compressive force to a second compressive force through the second range of motion. In various embodiments, the trigger assembly may be configured to limit the compressive force to a third compressive force through the fourth range of motion.

Figure 16:
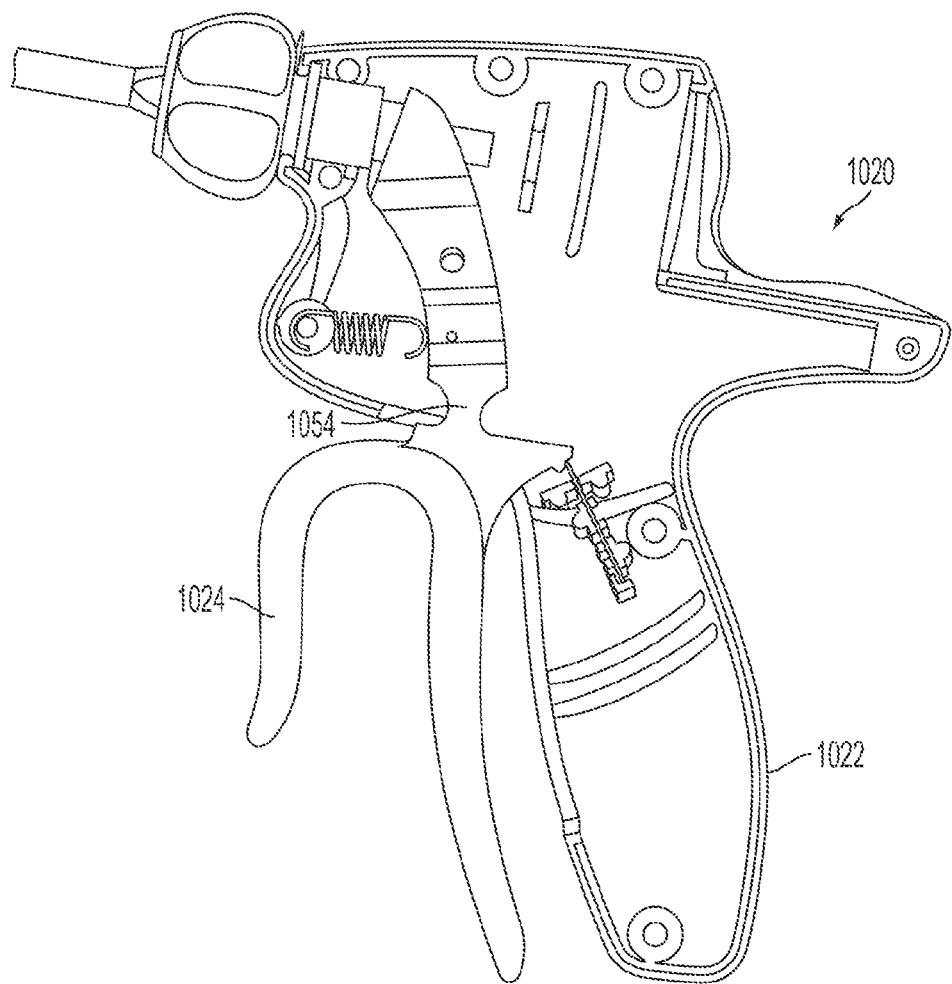
FIG. 16 includes a surgical instrument comprising a trigger assembly according to various embodiments.

In various embodiments, the trigger assembly may comprise one or more detent features and/or other kind of feature(s) to provide an audible and/or tactile indication of the angular position of end effector about the longitudinal axis defined by sheath. Referring to FIG. 16, in various embodiments, trigger 1024 may be pivotally attached to hand piece 1020. Trigger 1024 may comprise a living hinge 1054. In various embodiments, the living hinge may provide an audible and/or tactile indication to the user. For example, a trigger 1024 may be squeezed toward a pistol grip 1022 to actuate an end effector (not shown). The living hinge may provide the audible and/or tactile indication when trigger 1024 is in an actuated position. Various examples of devices comprising audible and/or tactile indicators are described in U.S. patent application Ser. No. 12/842,565, filed Jul. 23, 2010, entitled "ELECTROSURGICAL CUTTING AND SEALING INSTRUMENT", the disclosure of which is incorporated by reference herein.

In various embodiments, in use, end effector 40 may be inserted into a patient via a trocar to a desired position and orientation relative to an anatomical structure within the patient. In various embodiments, the user may operate trigger 24 through the first range of motion to capture two layers of tissue of the anatomical structure 42, 44 when the anatomical structure has a diameter greater than about 3 mm. As described above, flanges 62, 66 cammingly act to pivot jaw 44 toward jaw 42 when firing beam 60 is actuated distally by squeezing trigger 24 from the unactuated position to the first actuated position. Jaws 42, 44 may apply the first compressive force to the layers of tissue captured therebetween when trigger 24 is in the first actuated position. In various embodiments, the first compressive force may compress the anatomical structure such that the inner layers of the anatomical structure are extruded and separated and only the outer layer of the anatomical structure is between jaws 42, 44. In various embodiments, activation button 26 may serve as a mechanical lockout against trigger 24 such that a bipolar RF current may not flow to electrode surfaces 50, 52 when trigger 24 is in the first actuated position.

In various embodiments, the user may operate trigger 24 through the second range of motion to sever the clamped tissue layers between jaws 42, 44 and thermally weld the severed tissue layers. As described above, distal blade 64 severs the clamped tissue layers as firing beam 60 continues to advance distally by the user squeezing trigger 24 from the first actuated position to the second actuated position. Jaws 42, 44 may apply the second compressive force to the layers of tissue captured therebetween when trigger 24 is in the second actuated position. In various embodiments, the second compressive force may allow the inner severed tissue layer portions directly contact each other. With jaws 42, 44 applying the second compressive force to the severed tissue layer portions, electrode surfaces 50, 52 are activated with bipolar RF energy by the user depressing activation button 26. As described above, a bipolar RF current flows between firing beam 60 and electrode surfaces 50, 52 through the compressed regions of severed tissue layer portions to thermally welds the tissue layer portions on one side of firing beam 60 together and the tissue layer portions on the other side of firing beam 60 together. In various embodiments, the inner severed tissue layer portions of the anatomical structure may be thermally welded to each other. In various embodiments, activation button 26 may serve as a mechanical lockout against trigger 24 such that a bipolar RF current may not flow to electrode surfaces 50, 52 unless trigger 24 is in the second actuated position and button 26 is being pressed simultaneously.

In various embodiments, in use, end effector 40 may be inserted into a patient via a trocar to a desired position and orientation relative to an anatomical structure within the patient. In various embodiments, the user may operate trigger 24 through the third range of motion to capture two layers of tissue of the anatomical structure 42, 44 when the anatomical structure has a diameter up about 3 mm. As described above, flanges 62, 66 cammingly act to pivot jaw 44 toward jaw 42 when firing beam 60 is actuated distally by squeezing trigger 24 from the unactuated position to the third actuated position. The user may continue to operate trigger 24 through the third range of motion to sever the clamped tissue layers between jaws 42, 44 and thermally weld the severed tissue layers. As described above, distal blade 64 severs the clamped tissue layers as firing beam 60 continues to advance distally by the user squeezing trigger 24 from the first actuated position to the third actuated position. Jaws 42, 44 may apply the third compressive force to the layers of tissue captured therebetween when trigger 24 is in the third actuated position.

With jaws 42, 44 applying the third compressive force to the severed tissue layer portions, electrode surfaces 50, 52 are activated with bipolar RF energy by the user depressing activation button 26. As described above, a bipolar RF current flows between firing beam 60 and electrode surfaces 50, 52 through the compressed regions of severed tissue layer portions to thermally welds the tissue layer portions on one side of firing beam 60 together and the tissue layer portions on the other side of firing beam 60 together. In various embodiments, activation button 26 may serve as a mechanical lockout against trigger 24 such that a bipolar RF current may not flow to electrode surfaces 50, 52 unless button trigger is in the third actuated position and button 26 is being pressed simultaneously.

As described above, in various embodiments, electrosurgical instrument 10 may comprise a trigger assembly operable to control jaws 44, 42 to thereby selectively compress tissue between jaws 42, 44 at various compressive forces. Various embodiments, of the trigger assembly and other components of hand piece 20 are described in greater detail below, while further examples will be apparent to those of ordinary skill in the art in view of the teachings herein.

As described above, in various embodiments, firing beam 60 may be advanced distally by squeezing trigger 24 toward pistol grip 22 to the actuated position; while firing beam 60 may be retracted proximally by releasing trigger 24 and/or by actively moving trigger 24 away from pistol grip 22 to the unactuated position. In various embodiments, the trigger assembly may comprise a yoke to couple trigger 24 to firing beam 60. In various embodiments, the trigger assembly may further comprise a link arm to couple trigger 24 to firing beam 60. Of course, firing beam 60 may be moved in any other suitable fashion.

In various embodiments, an electrosurgical instrument may generally comprise a shaft comprising a proximal end and a distal end, an end effector extending from the distal end of the shaft, wherein the end effector is operable to grasp tissue, a hand piece extending from the proximal end, wherein the hand piece comprises a pistol grip and a trigger assembly extending from the hand piece, wherein the trigger assembly comprises a trigger movable relative to the pistol grip between an unactuated position and a first actuated position and a second actuated position, wherein the trigger is operable to control the end effector to selectively grasp tissue at a first compressive force when the trigger is in the first actuated position and a second compressive force when the trigger is in the second actuated position.

Figure 6:
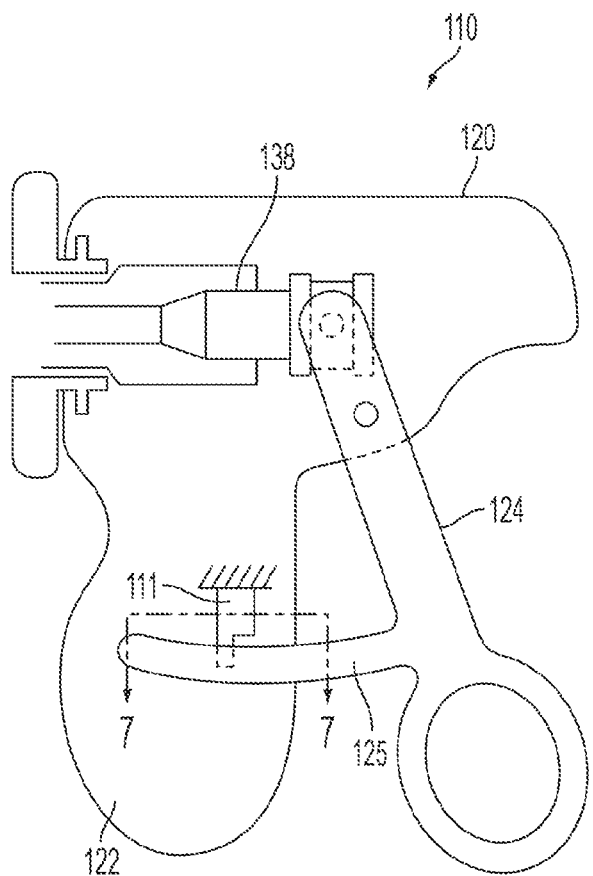
FIG. 6 includes a surgical instrument comprising a trigger bypass mechanism according to various embodiments.
Figure 7:
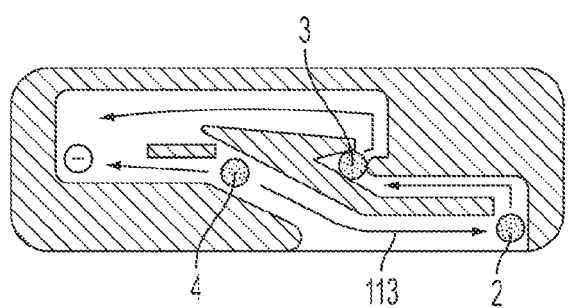
FIG. 7 includes the trigger bypass mechanism illustrated in FIG. 6.

In various embodiments, referring to FIGS. 6 and 7, electrosurgical instrument 110 may generally comprise a bypass latch or over-center mechanism configured to define a bypass pathway 113 for trigger 124. In various embodiments, hand piece 120 comprises pistol grip 122, bypass latch leaf spring 111, and a trigger assembly comprising trigger 124 pivotally attached to yoke 138. Trigger 124 may comprise extension arm 125 comprising slot 113 defining a bypass pathway. One end of bypass latch leaf spring 111 may be fixedly attached to hand piece 120 and the free end of bypass latch leaf spring 111 may be disposed in slot 113. As shown in FIG. 7, the free end of bypass latch leaf spring 111 engages a first portion of slot 113 when trigger 124 is in the unactuated position 1, a second portion of slot 113 when trigger 124 is in the first actuated position 2, and a third portion of slot 113 when trigger 124 is in the second actuated position 3.

In use for tissues having large diameters or thicknesses, bypass latch leaf spring 111 may be configured to pass through the first actuated position 2 and release to or near the second actuated position 3 when electrosurgical instrument 110 is activated to seal the tissue between jaws (not shown). In this way, the user crushes the tissue at the first actuated position 2 such that the inner tissue layers may be extruded laterally before end effector (not shown) is activated to cut and coagulate the outer tissue layers at the second actuated position 3. In use for tissues have small diameters, bypass latch leaf spring 111 may be configured to pass directly to the third actuated position 4 when electrosurgical instrument 110 is activated to capture, cut, and/or seal the tissue between jaws (not shown). Without wishing to be bound to any particular theory, it is believed that electrosurgical instruments according to the present disclosure may utilize substantially similar power and clamp force to coagulate larger blood vessels as current ultrasonic shear devices use to coagulate smaller blood vessels.

Figure 8A:
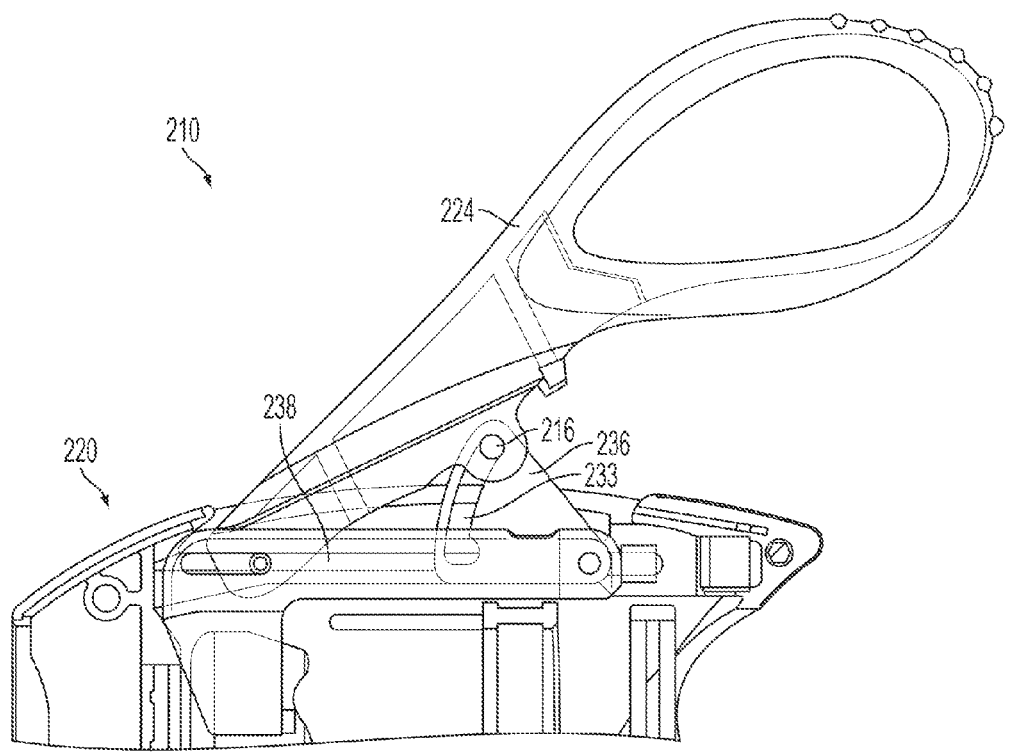
FIGS. 8A-G include a surgical instrument comprising a trigger assembly in various positions according to various embodiments.
Figure 8B:
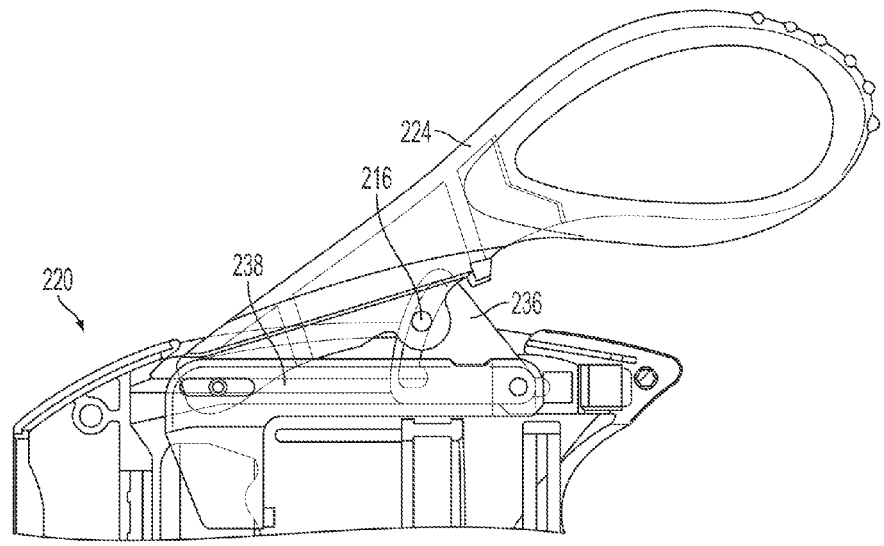
Figure 8C:
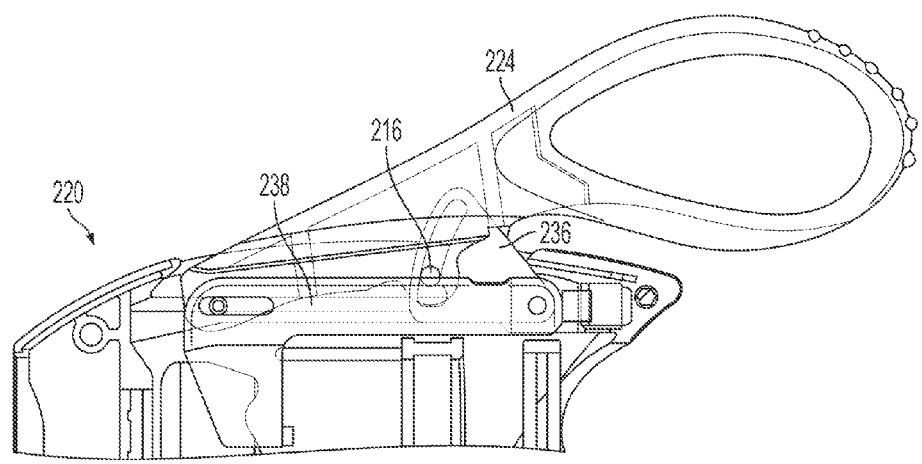
Figure 8D:
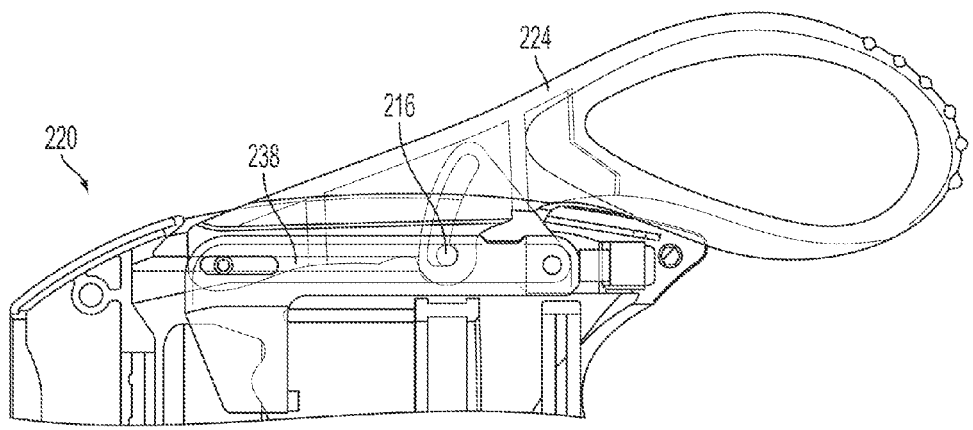
Figure 8E:
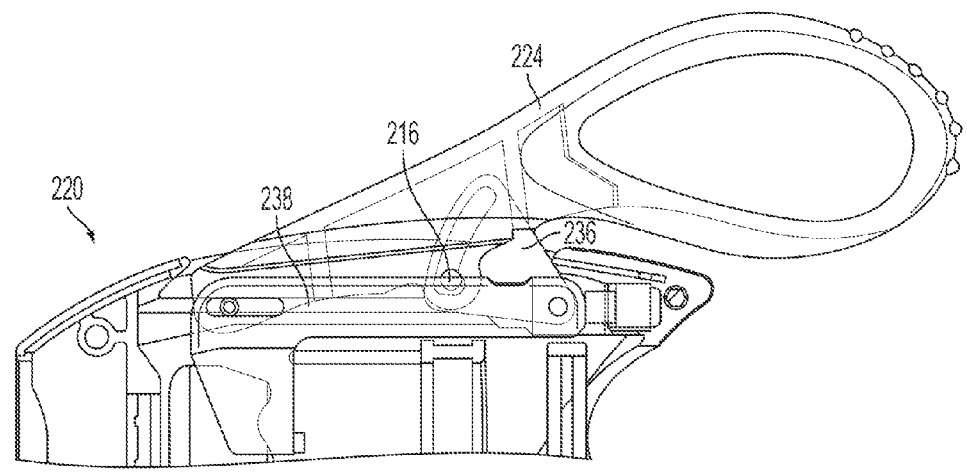

In various embodiments, referring to FIGS. 8A-G, hand piece 220 may generally comprise yoke 238 longitudinally slideable relative to hand piece 220, trigger 224 slideably attached to yoke 238 and rotationally attached to hand piece 220, and link arm 236 fixedly attached to yoke 238 and rotationally attached to hand piece 220. Link arm 236 may comprise slot 233. Trigger 224 may be coupled to link arm 236 by trigger pin 216. One end of trigger pin 216 may be disposed in slot 233. In various embodiments, slot 233 may comprise a radial feature configured to act as a cam and trigger pin 216 may be configured to act as a cam follower. In various embodiments, slot 233 may comprise a first portion and a second portion. In various embodiments, the first portion of slot 233 may comprise a radial feature and the second portion of slot 233 may comprise a longitudinal feature. For example, as shown in FIG. 8A, slot 233 may comprise an L-shape wherein the first portion of slot 233 a extends proximally and radially from a plane including the longitudinal axis of hand piece 220, and the first portion of slot 233 extends parallel to the plane including the longitudinal axis of hand piece 220.

In use, referring to FIGS. 8A-G, when trigger 224 moves from an unactuated position (FIG. 8A) through the first range of motion (FIGS. 8B, 8C) to the first actuated position (FIG. 8C), trigger pin 216 slides along the first portion of slot 233 to convert the movement of trigger 224 into proximal linear movement of yoke 238. Trigger 224 may continue to move from the first actuated position through a second range of motion (FIG. 8D) to the second actuated position (FIG. 8D) when trigger pin 216 slides along a second portion of slot 233 to convert the movement of trigger 224 into distal linear movement of yoke 238. In various embodiments, yoke 238 may travel a first distance through the first range of motion and a second distance through a second range of motion. In various embodiments, the first distance may be greater than or equal to the second distance. In various embodiments, the difference between the first distance and second distance may decrease the compressive force applied to captured tissue from the first compressive force to the second compressive force.

Figure 8F:
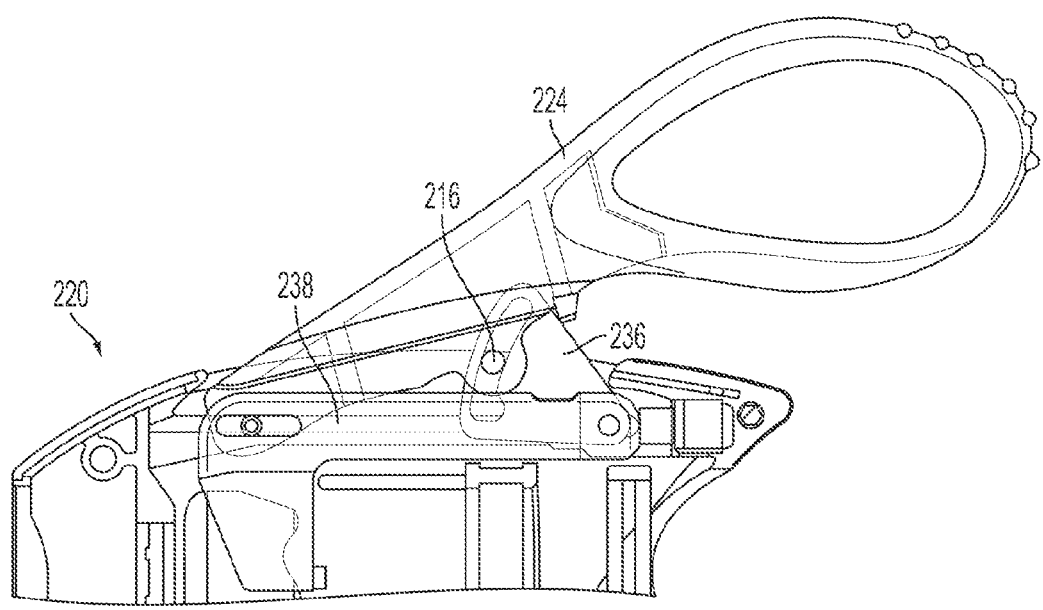
Figure 8G:
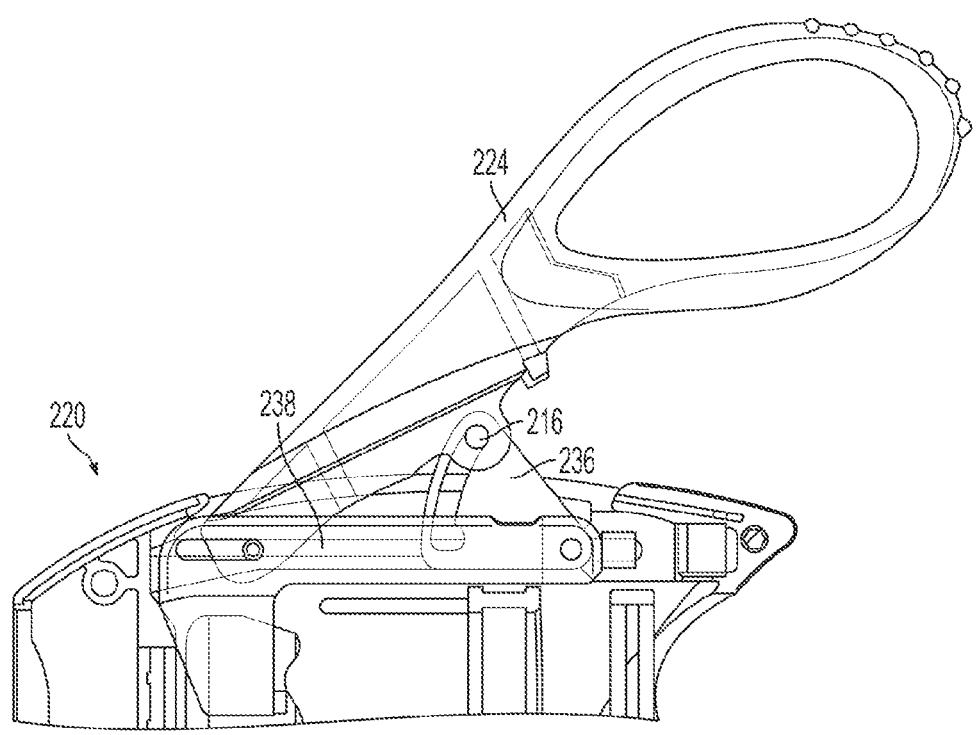

Referring to FIGS. 8D-8G, when trigger 224 moves from the second actuated position (FIG. 8D) through the third range of motion (FIGS. 8E-G) to the unactuated position, a spring (not shown) may return trigger 224 to an unactuated position where it is pivoted away from the longitudinal axis. In various embodiments, referring to FIG. 8E, trigger 224 is pivotable about a pivot point that is fixed relative to hand piece 220. When trigger 224 rotates away from the longitudinal axis, trigger pin 216 slides along the second portion of slot 233 to the first portion of slot 233. As shown in FIG. 8F, as trigger 224 continues to rotate away from the longitudinal axis, trigger pin 216 slides along the first portion of slot 233 to convert the movement of trigger 224 into proximal linear movement of yoke 238. The unactuated position is illustrated in FIG. 8G.

In various embodiments, the trigger assembly may comprise mechanical assistance to trigger 24 as it approaches the end of its return stroke. In various embodiments, it may also be desirable to provide a substantially constant amount of resistance to the user squeezing trigger during the entire range of motion such that the resistance forces encountered by the user are not substantially greater during certain stages of the firing stroke and return stroke.

Figure 9A:
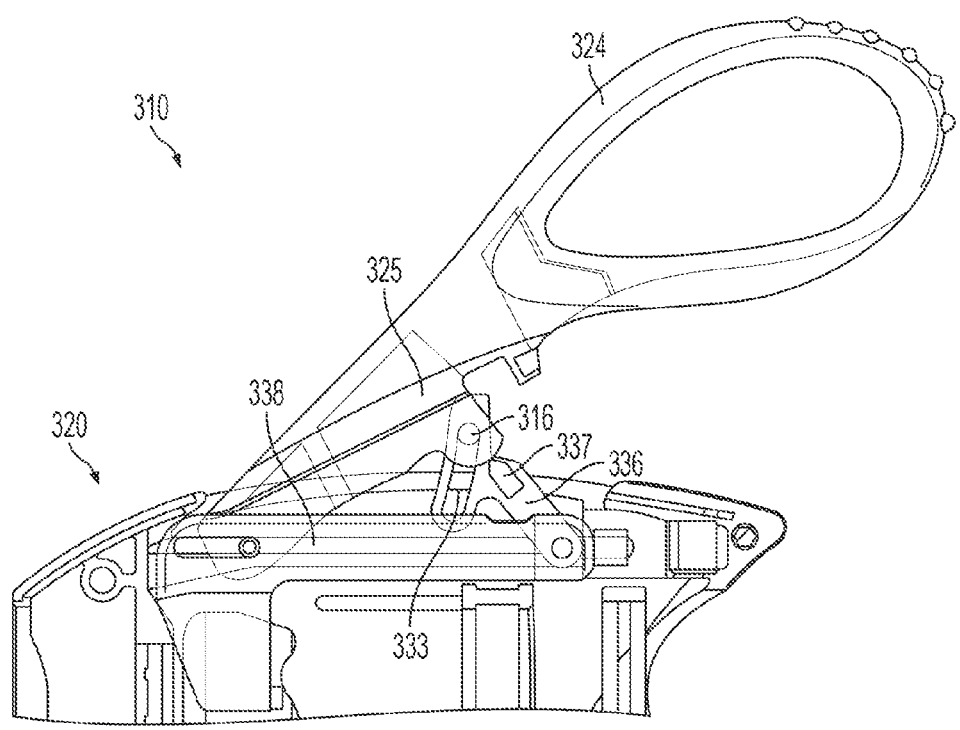
FIGS. 9A-G include a surgical instrument comprising a trigger assembly in various positions according to various embodiments.
Figure 9B:
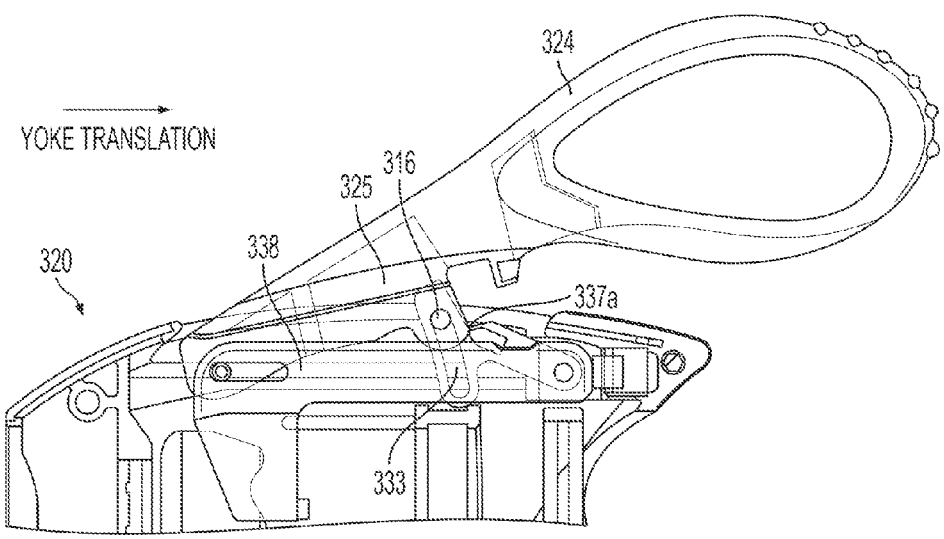

In various embodiments, referring to FIGS. 9A-G, hand piece 320 may generally comprise yoke 338 longitudinally slideable relative to hand piece 320, trigger 324 slidingly attached to yoke 338 and rotationally attached to hand piece 320, and link arm 336 pivotally attached to yoke 338 and rotationally attached to trigger 324. Trigger 324 may be coupled to link arm 336 by trigger pin 316 as described above. In various embodiments, trigger 324 may be configured to act as a cam and slot 333 and link 336 may comprise a projection configured to act as a cam follower 337. In various embodiments, link 336 may comprise projection 337 to engage portion 325 of trigger 324 comprising trigger pin 316. In various embodiments, projection 337 may engage a first portion of trigger 324 when trigger 324 is in the first actuated position and a second portion of trigger 324 when trigger 324 is in the second actuated position. In various embodiments, projection 337 may comprise an angled surface. For example, as shown in FIG. 9A, projection 337 may comprise a pentagon-shape including an angled surface 337a. In various embodiments, angled surface 337a of projection 337 may engage a first portion 325 of trigger 324 when trigger 324 is in the first actuated position and a second portion 326 of trigger 324 when trigger 324 is in the second actuated position.

Figure 9C:
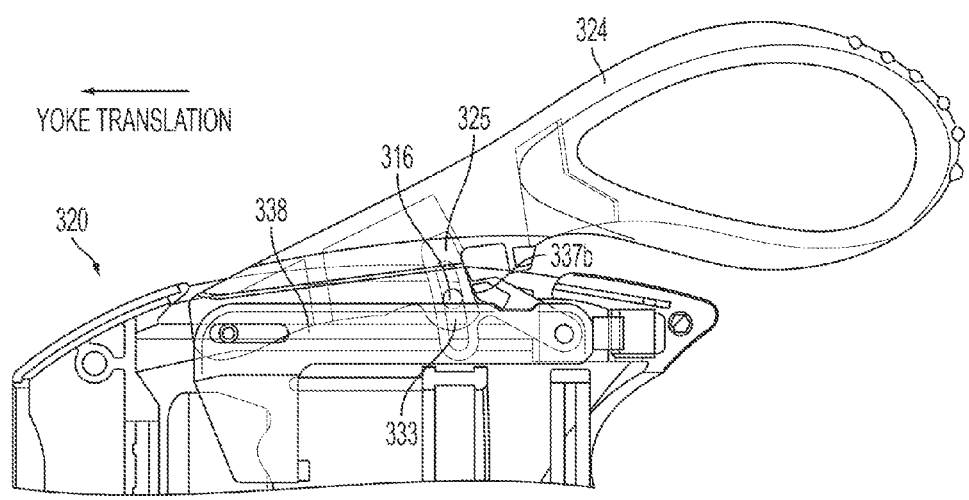
Figure 9D:
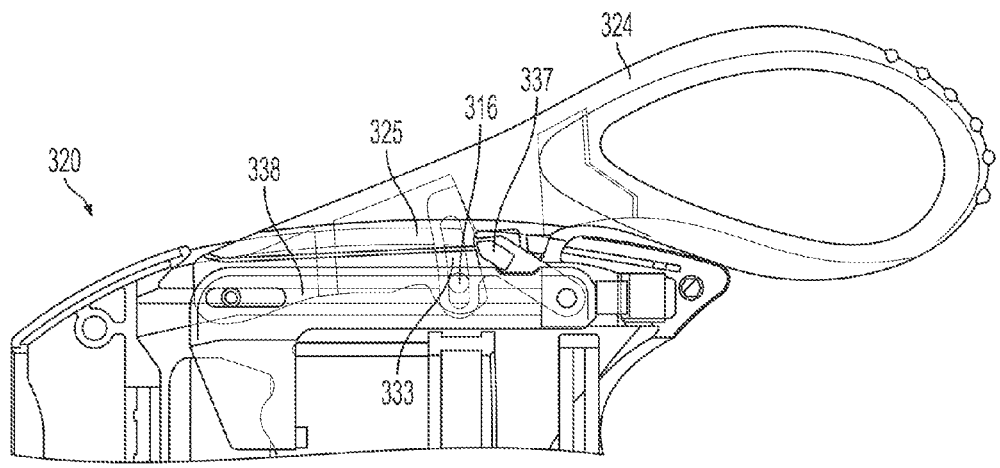
Figure 9E:
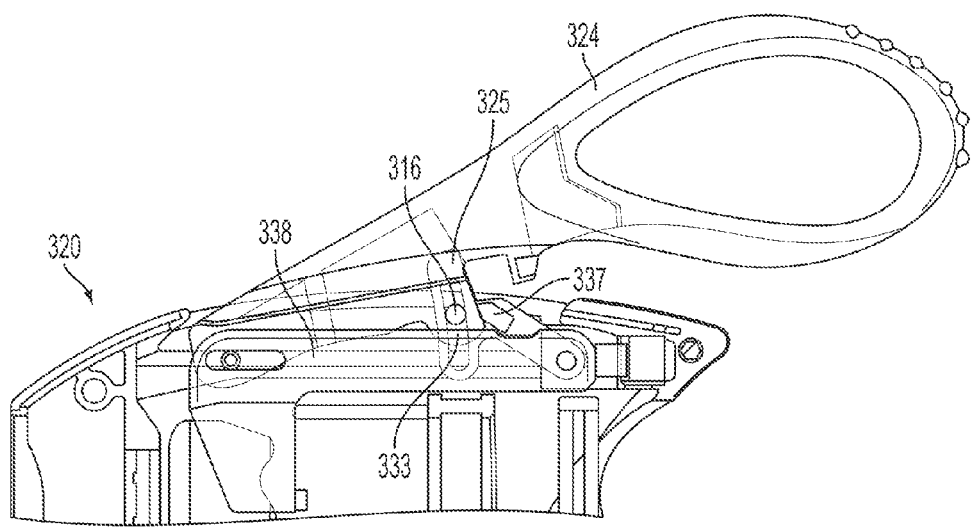
Figure 9F:
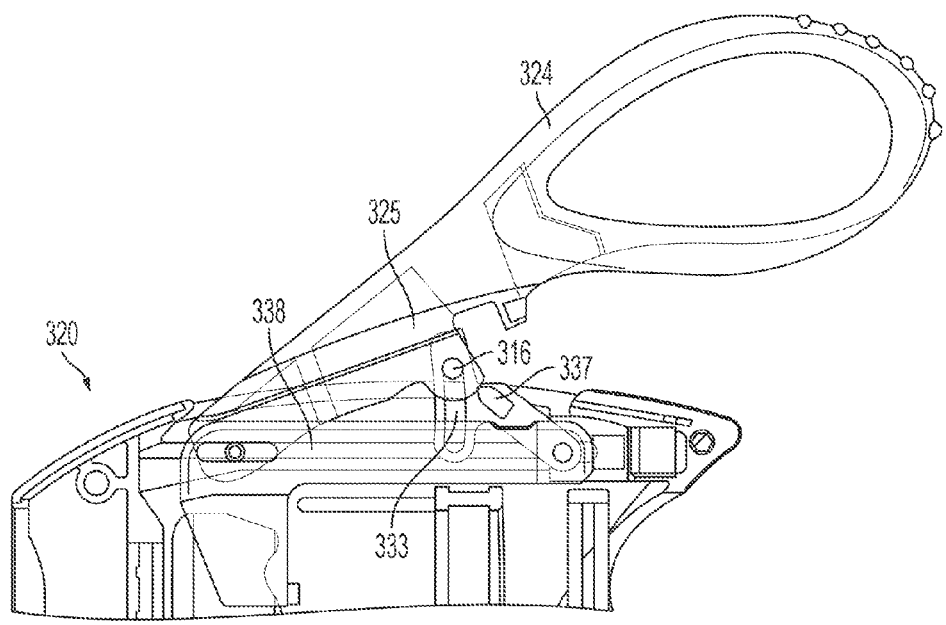
Figure 9G:
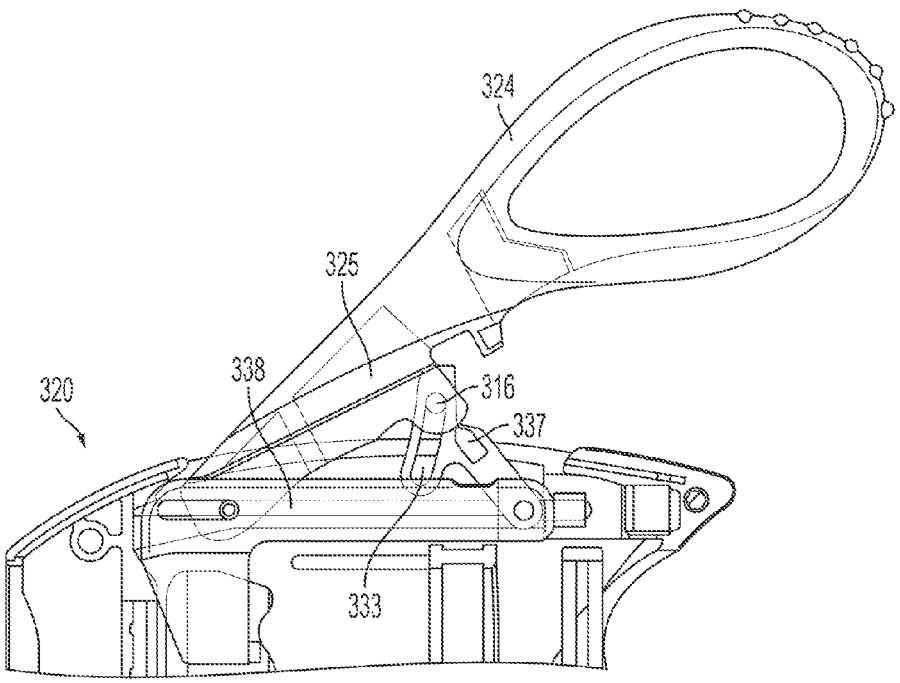

In use, referring to FIGS. 9A-G, when trigger 324 moves from an unactuated position (FIG. 9A) through the first range of motion to the first actuated position (FIG. 9B), a first portion of angled surface 337a of projection 337 engages a first portion of trigger 324 to convert the movement of trigger 324 into proximal linear movement of yoke 338. Trigger 324 may continue to move from the first actuated position through a second range of motion (FIG. 9C) to the second actuated position (FIG. 9D) when a second portion of angled surface 337a of projection 337 engages a second portion of trigger 324 to convert the movement of trigger 324 into distal linear movement of yoke 338. As shown in FIG. 9C, in various embodiments, the second portion of angled surface 337*a* may comprise a complementary angle to the second portion of trigger 324. The complementary surface of trigger 324 may contact the complementary surface of projection 337*a* when trigger 324 moves from the first actuated position through the second range of motion to the second actuated position. As described above, in various embodiments, yoke 338 may travel a first distance through the first range of motion and a second distance through a second range of motion such that the difference between the first distance and second distance may decrease the compressive force applied to captured tissue from the first compressive force to the second compressive force. As described above, the user may release trigger 324, and the spring (not shown) may return trigger 324 to an unactuated position. When trigger 324 moves from the second actuated position (FIG. 9E) through the third range of motion (FIG. 9F) to the unactuated position (FIG. 9G), in various embodiments, trigger 324 may be coupled to link arm 336 by trigger pin 316 disposed in slot 333 to prevent trigger 324 from over travel and locking.

Figure 10A:
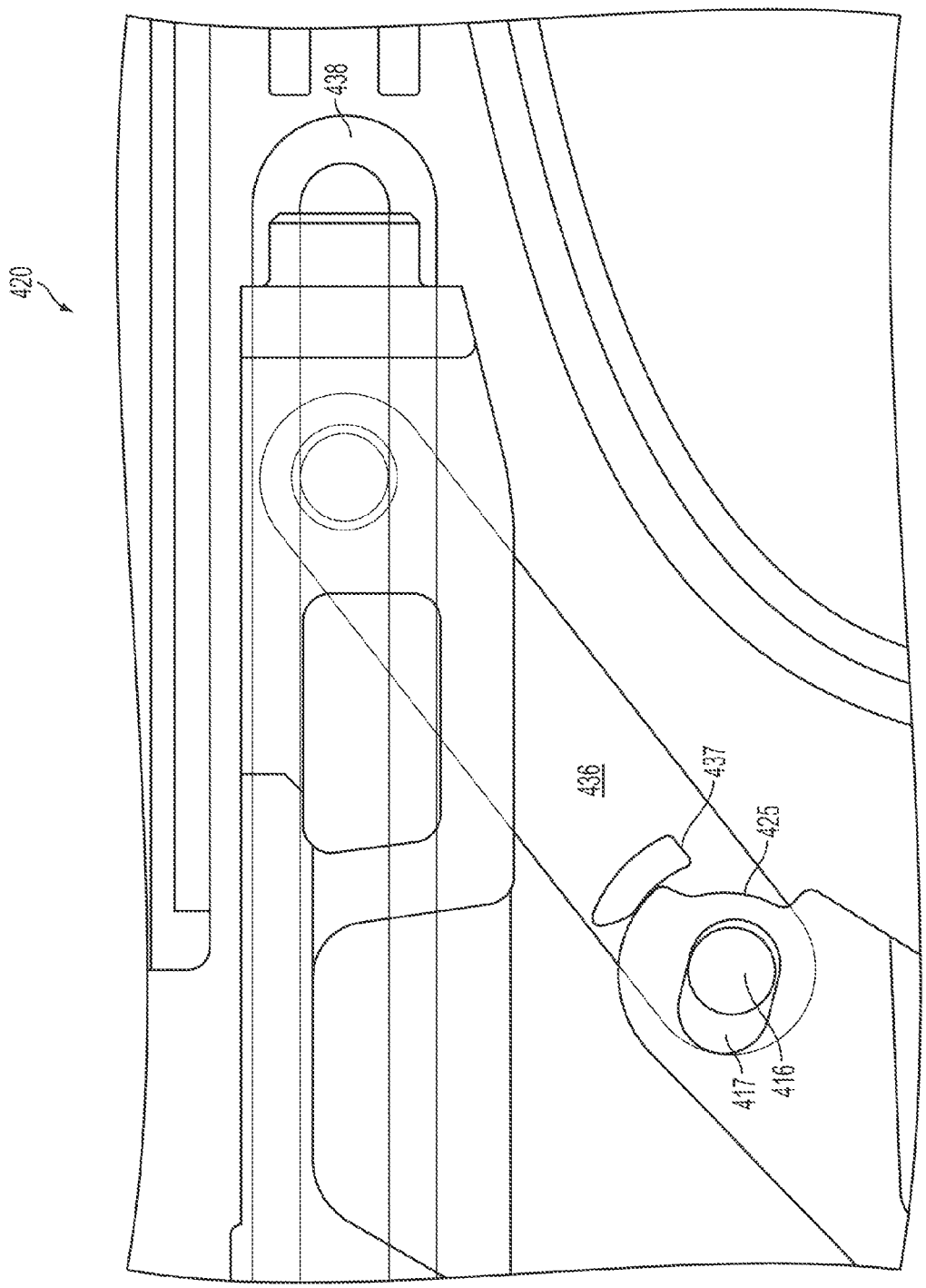
Figure 10B:
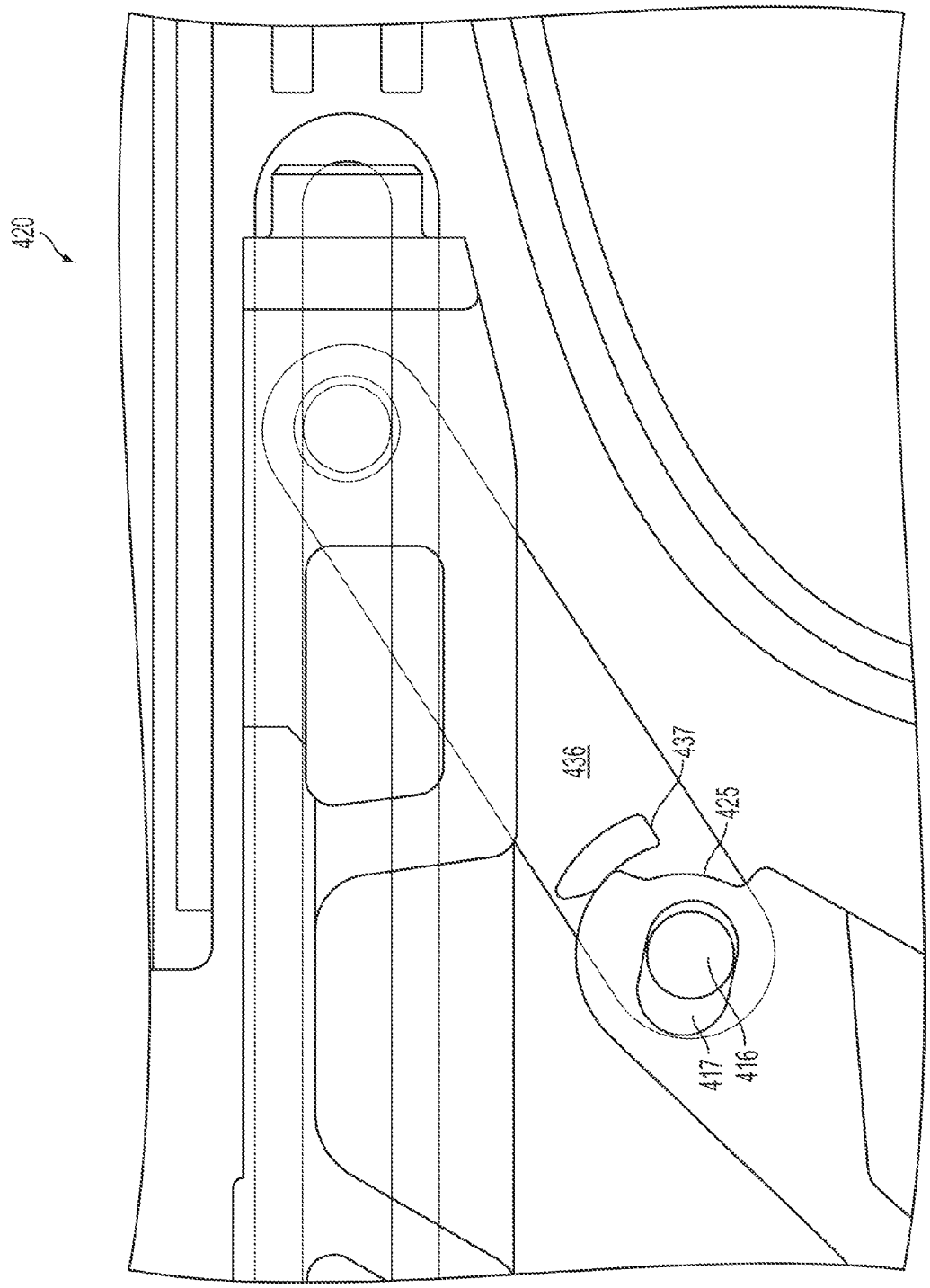
Figure 10D:
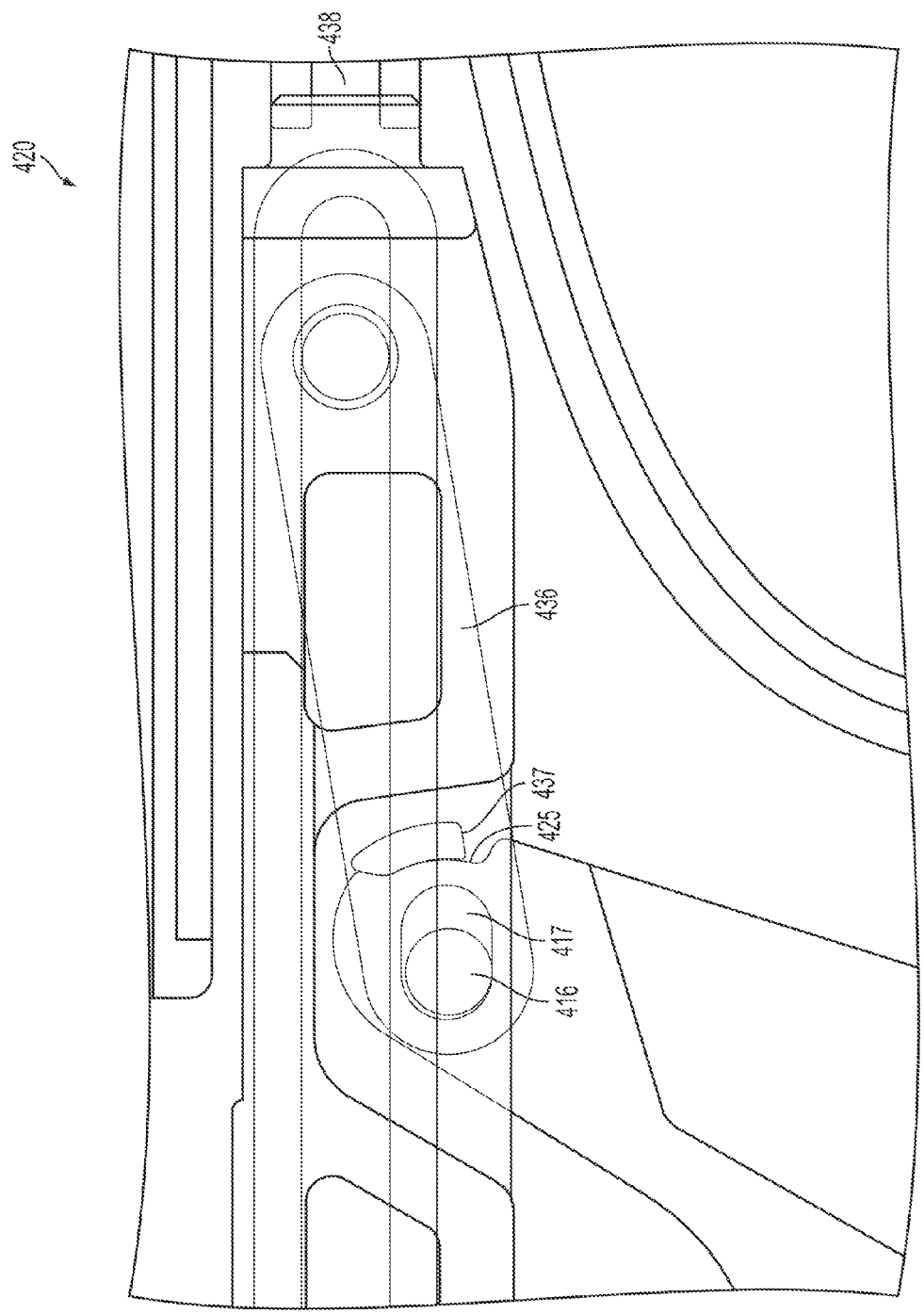

In various embodiments, referring to FIGS. 10A-D, hand piece 420 may generally comprise yoke 438 longitudinally slideable relative to hand piece 420, trigger 424 pivotally attached to yoke 338, and link arm 436 pivotally attached to yoke 438. Trigger 424 may be coupled to link arm 436 by trigger pin 416 disposed in trigger slot 417. Trigger 424 may comprise a surface comprising relief notch 425 configured to act as a cam and link arm 436 may comprise a projection 437 configured to act as a cam follower. A return spring (not shown) may be coupled to yoke 438 by pin (not shown) configured to resiliently bias yoke 438 distally and projection 437 of link arm 436 to contact the surface of trigger 424. In various embodiments, projection 437 of link arm 436 may engage the surface of trigger 424 lacking relief notch 425 when trigger 424 is in the first actuated position and engage relief notch 425 when trigger 424 is in the second actuated position. In various embodiments, projection 437 of link arm 438 may comprise a complementary shape to relief notch 425. For example, as shown in FIG. 10D, projection 437 of link arm 438 may comprise a complementary shape to relief notch 425.

In use, referring to FIGS. 10A-D, when trigger 424 moves from an unactuated position (FIG. 10A) through the first range of motion to the first actuated position (FIGS. 10B and 10C), projection 437 of link arm 438 engages a surface of trigger 424 lacking relief notch 425 to compress return spring (not shown) and convert the movement of trigger 424 into proximal linear movement of yoke 438. Trigger 424 may continue to move from the first actuated position through a second range of motion to the second actuated position (FIG. 10D) when projection 437 of link arm 438 engages relief notch 425 to decompress return spring (not shown), and to convert the movement of trigger 424 into distal linear movement of yoke 438. In various embodiments, trigger pin 417 may contact a first portion of trigger slot 417 when trigger 424 is in the first actuated position. Trigger pin 417 may slide along trigger slot 417 through the second range of motion to a second portion of trigger slot 417 when trigger 423 is in the second actuated position. As described above, in various embodiments, yoke 438 may travel a first distance through the first range of motion and a second distance through a second range of motion such that the difference between the first distance and second distance may decrease the compressive force applied to captured tissue from the first compressive force to the second compressive force. In various embodiments, as shown in FIG. 10D, the second distance may relate to the depth of relief notch 425 and/or length of trigger slot 417. As described above, the user may release trigger 424, and trigger pin 416 may slide along trigger slot 417 to the first portion of trigger slot 417, and projection 437 of link are 438 may rotate out of relief notch 425 to return trigger 324 to an unactuated position.

Figure 11A:
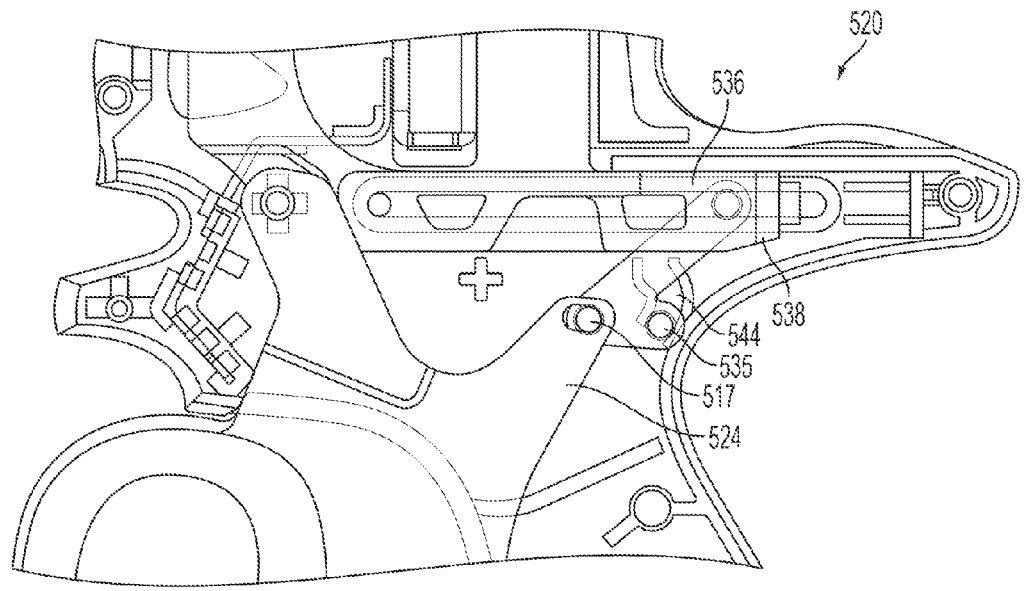
FIGS. 11A-C include a surgical instrument comprising a trigger assembly in various positions according to various embodiments.
Figure 11B:
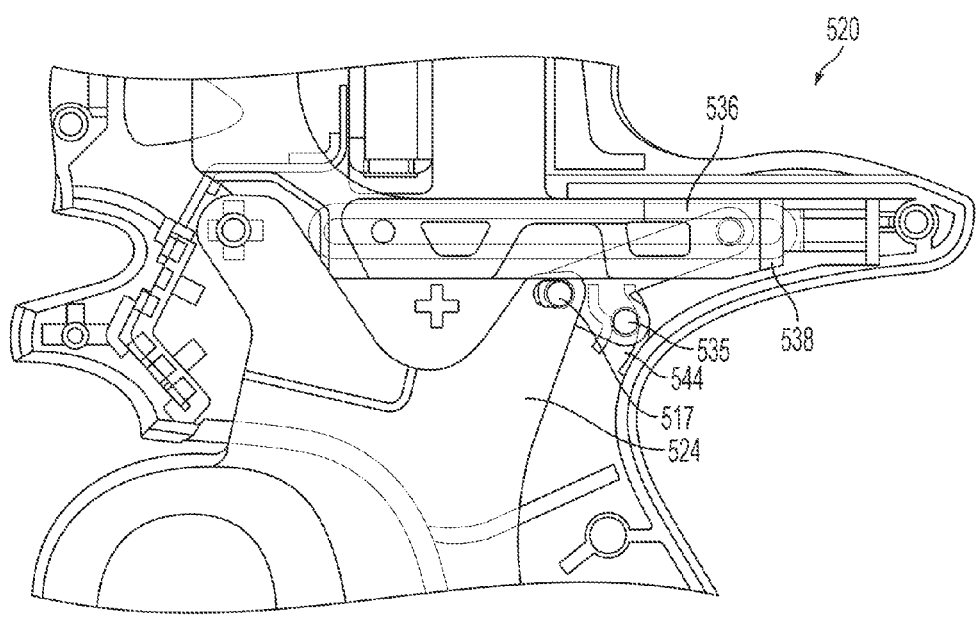
Figure 11C:
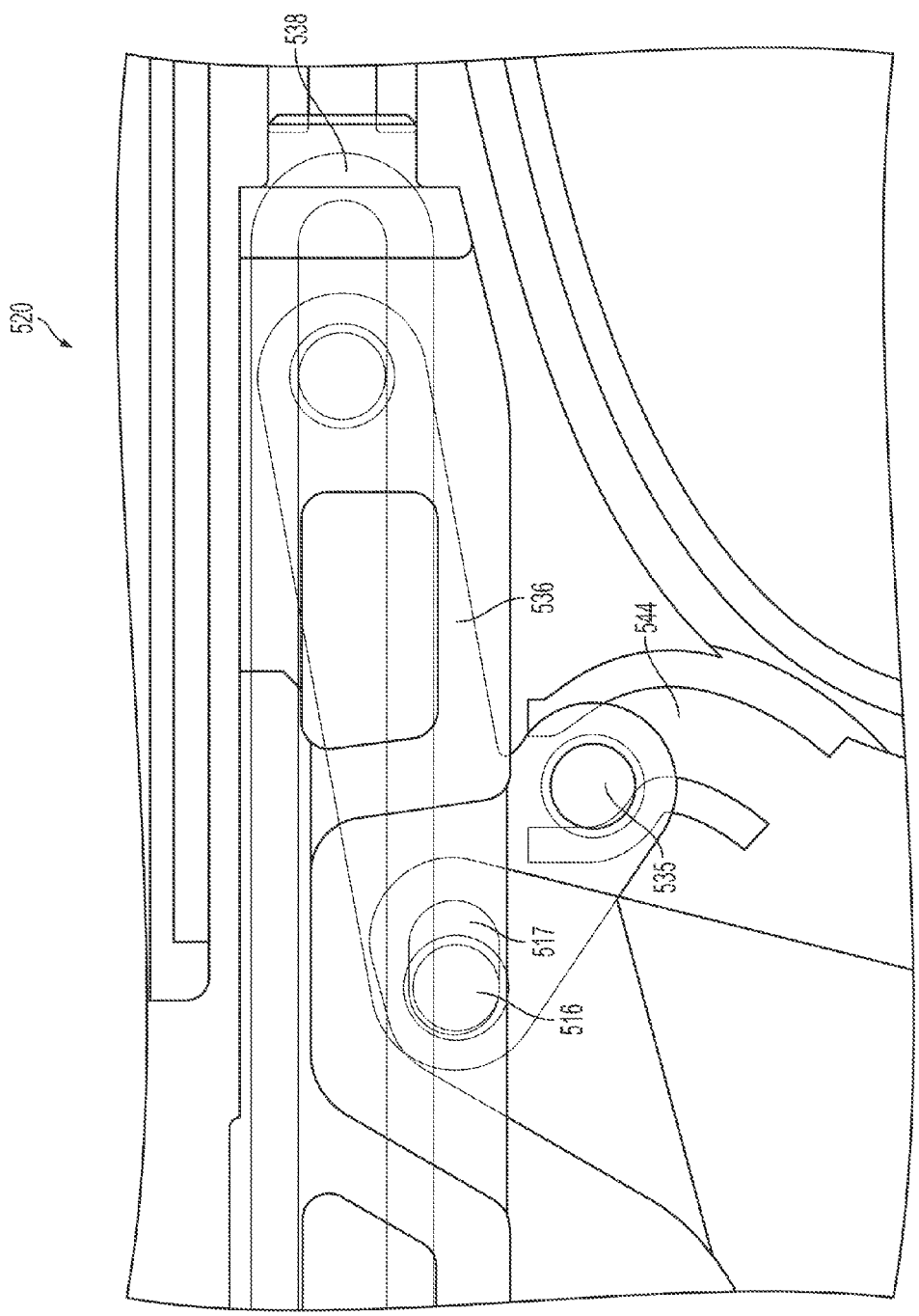

In various embodiments, referring to FIGS. 11A-C, hand piece 520 may generally comprise yoke 538 longitudinally slideable relative to hand piece 520, trigger 524 pivotally attached to yoke 538, and link arm 536 pivotally attached to yoke 538. In various embodiments, hand piece 520 may comprise a handle shroud slot 544. Trigger 524 may be coupled to link arm 536 by trigger pin 516 disposed in trigger slot 517. Link arm 537 may comprise a projection comprising a link pin 537. Link pin 537 may be disposed in handle shroud slot 544. In various embodiments, link pin 537 may slide along handle shroud slot 544. As discussed above, a return spring (not shown) may be coupled to yoke 538 by pin (not shown) configured to resiliently bias yoke 538 distally. In various embodiments, link pin 537 may contact a first portion of handle shroud slot 544 when trigger 524 is in the first actuated position and a second portion of handle shroud slot 544 when trigger 524 is in the second actuated position.

In use, referring to FIGS. 11A-C, when trigger 524 moves from an unactuated position (FIG. 11A) through the first range of motion to the first actuated position (FIG. 11B), link pin 537 slides along slot 544 to compress return spring (not shown) and convert the movement of trigger 524 into proximal linear movement of yoke 538. As shown in FIG. 11B, link pin 537 may engage a first portion of slot 544 when trigger 524 is in the first actuated position. Trigger 524 may continue to move from the first actuated position through a second range of motion to the second actuated position (FIG. 11C) when link pin 537 continues to travel along slot 544 to decompress return spring (not shown), and to convert the movement of trigger 524 into distal linear movement of yoke 538. As shown in FIG. 11B, link pin 537 may engage a second portion of slot 544 when trigger 524 is in the second actuated position. As described above, in various embodiments, yoke 538 may travel a first distance through the first range of motion and a second distance through a second range of motion such that the difference between the first distance and second distance may decrease the compressive force applied to captured tissue from the first compressive force to the second compressive force. In various embodiments, as shown in FIG. 11C, the second distance may relate to the configuration of slot 544 and/or length of trigger slot 517. As described above, the user may release trigger 524, and trigger pin 516 may slide along trigger slot 517, link pin 537 may slide along slot 544 to the first portion of slot 544 to return trigger 524 to an unactuated position. In various embodiments, slot 544 may prevent trigger 524 from over travel and locking.

Figure 12:
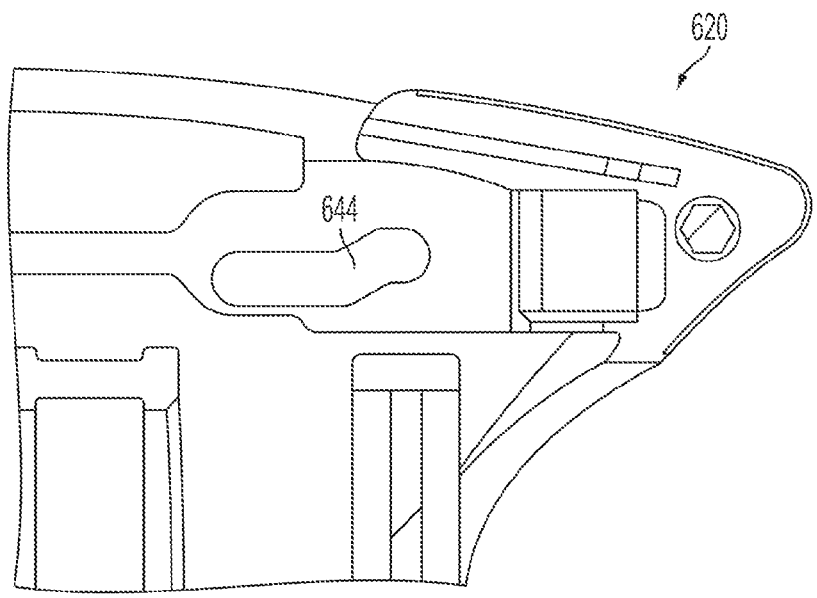
FIG. 12 includes a cross sectional view of a rear yoke pin path in a surgical instrument according to various embodiments FIG. 13 includes a cross sectional view of a rear yoke pin path in a surgical instrument according to various embodiments FIGS. 14A-C include a surgical instrument comprising a trigger assembly in various positions according to various embodiments.
Figure 13:
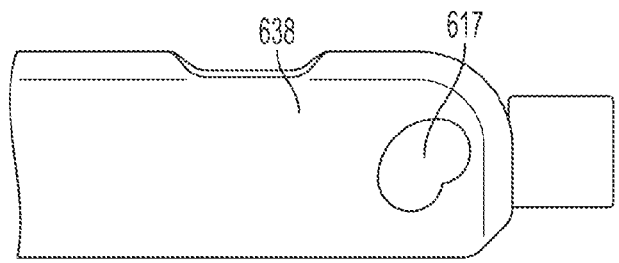
Figure 14A:
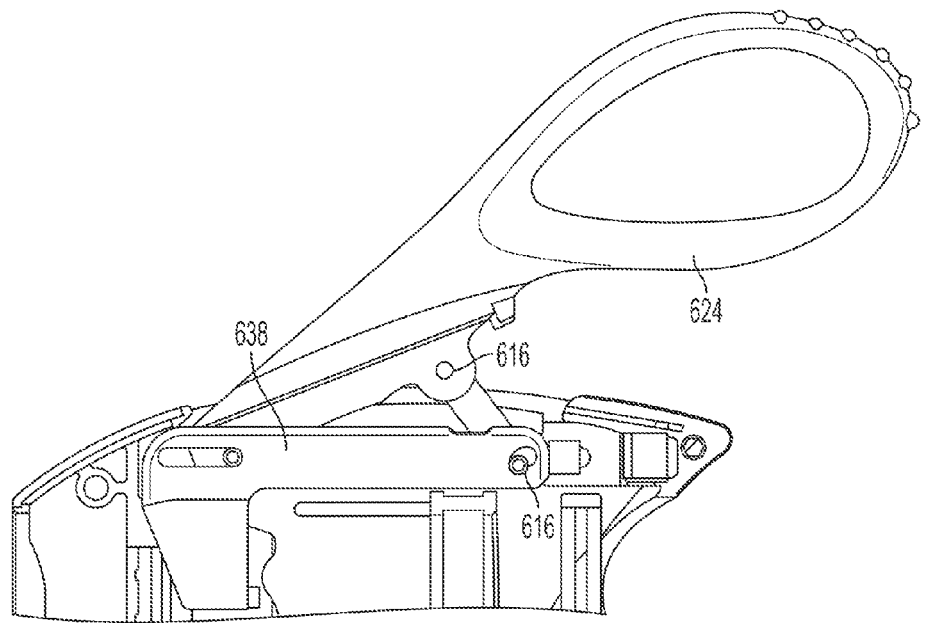
Figure 14B:
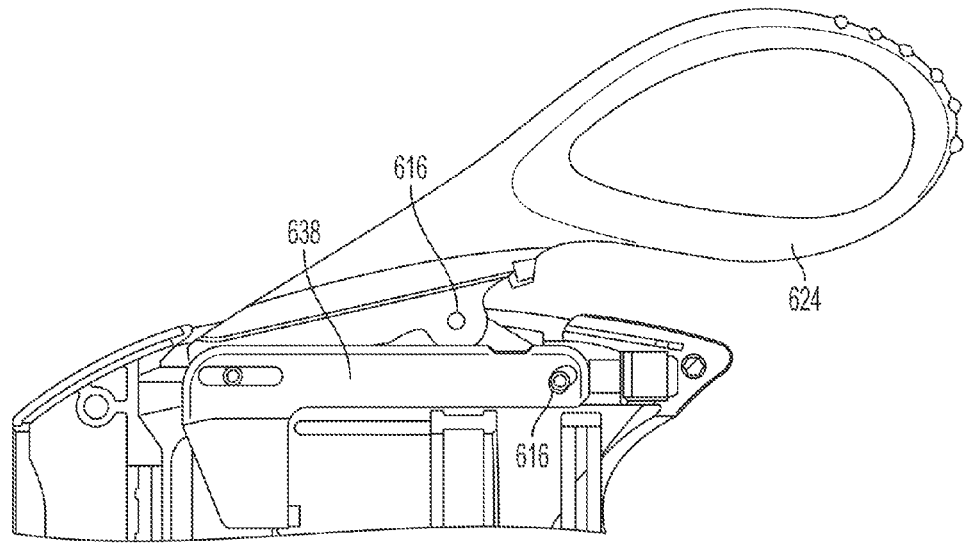
Figure 14C:
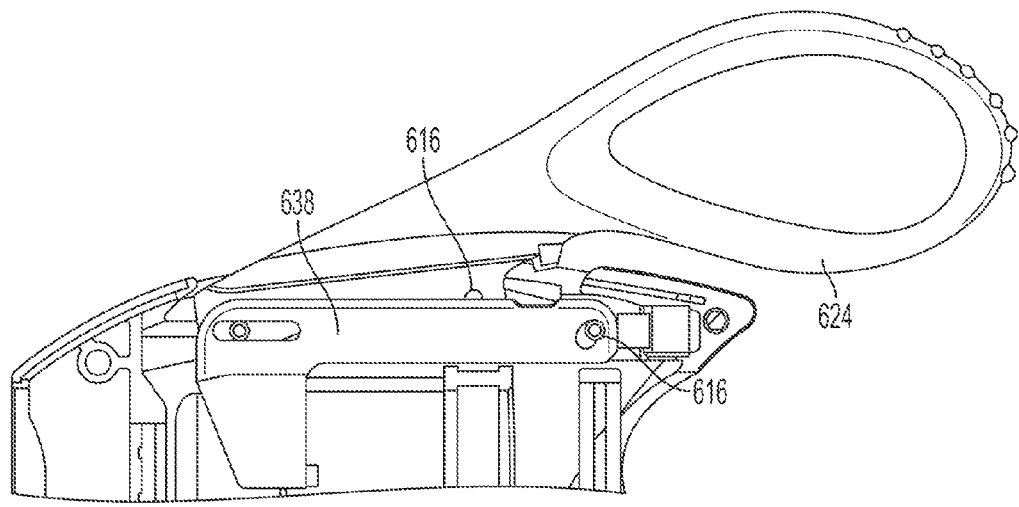

In various embodiments, referring to FIGS. 14A-C, hand piece 620 may generally comprise yoke 638 longitudinally slideable relative to hand piece 620, trigger 624 slideably attached to yoke 638 and pivotally attached to hand piece 620, and link arm 636 pivotally attached to yoke 638 and trigger 624. In various embodiments, referring to FIGS. 12 and 13, hand piece 620 may comprise slot 644 comprising first portion 644*a* and second portion 644*b*, and yoke 638 may comprise notch 617 comprising first portion 617*a* and second portion 617*b*. Rear yoke pin 618 may link hand piece 620, link arm 636, and yoke 638. A first end of rear yoke pin 618 may be disposed in slot 644 and a second end of rear yoke pin may be disposed in notch 617. In various embodiments, a first end of the rear yoke pin may engage a first portion 644*a* of slot 644 when the trigger is in the first actuated position, an upward step of slot 644 between first portion 644a and second portion 644b when the trigger is moved through a second range of motion, and a second portion 644b of slot 644 when the trigger is in the second actuated position. In various embodiments, the upward step may comprise an angled portion of the first portion 644a of slot 644. In various embodiments, a second end of the rear yoke pin may engage a first portion 617a of notch 617 when the trigger is in the first actuated position and second portion 617b when the trigger is in the second actuated position.

In use, referring to FIGS. 14A-C, when trigger 624 moves from an unactuated position (FIG. 14A) through the first range of motion to the first actuated position (FIG. 14B), the first end of the rear yoke pin may slide along the first portion 644a of slot 644 to convert the movement of trigger 624 into proximal linear movement of yoke 638. The second end of the rear yoke pin may rest in the first portion 617a of notch 617 when the trigger moves from an unactuated position through the first range of motion to the first actuated position. The first actuated position is illustrated in FIG. 14B. Trigger 624 may continue to move from the first actuated position through a second range of motion to the second actuated position (FIG. 14C) when the first end of the rear yoke pin slides along the upward step of slot 644 to the second portion 644b of slot 644 and the second end of the rear yoke pin may move from the first portion 617a to the second portion 617b of notch 617 to convert the movement of trigger 624 into distal movement of yoke 638. In various embodiments, yoke 638 may travel in an upward, distal direction when the first end of the rear yoke pin slides along the upward step of slot 644 and a linear distal direction when the first end of the rear yoke pin slides along the second portion 644b of slot 644. In various embodiments, the angular movement yoke 638 along slot 644 relative to the longitudinal axis and/or the movement of the rear yoke pin in notch 617 during the second range of motion may provide an audible and/or tactile indication to the user that trigger (not shown) is in the second actuated position. As discussed above, a return spring (not shown) may be coupled to yoke 638 by pin (not shown) configured to resiliently bias yoke 638 distally. As described above, the user may release the trigger, and the first end of the rear yoke pin may slide along slot 644 from the second portion 644b to the first portion 644a of slot 644 and the second end of the rear yoke pin may move from the second portion 617b to the first portion 617a of notch 617 to return the trigger to an unactuated position. In various embodiments, slot 644 may prevent the trigger from over travel and locking.

Figure 15A:
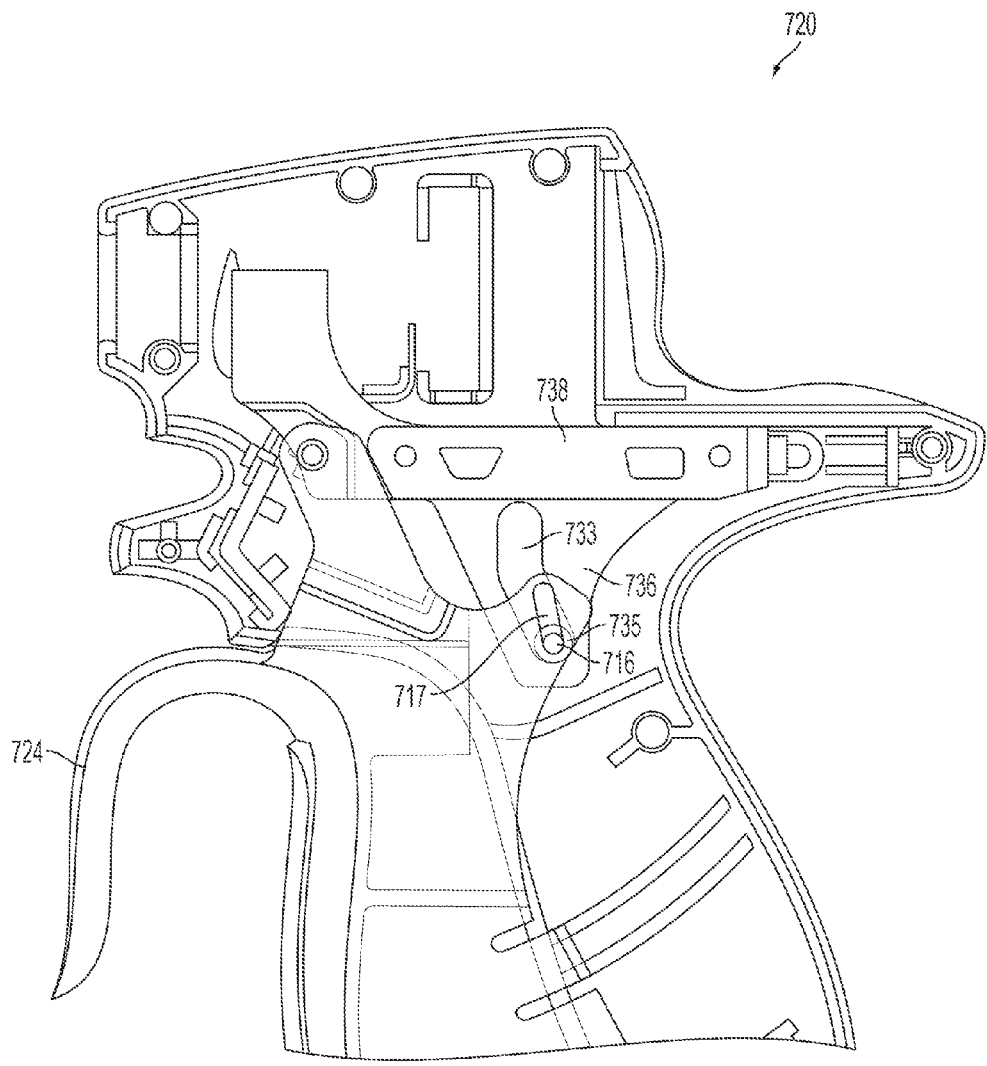
FIGS. 15A-K include a surgical instrument comprising a trigger assembly in various positions according to various embodiments.
Figure 15B:
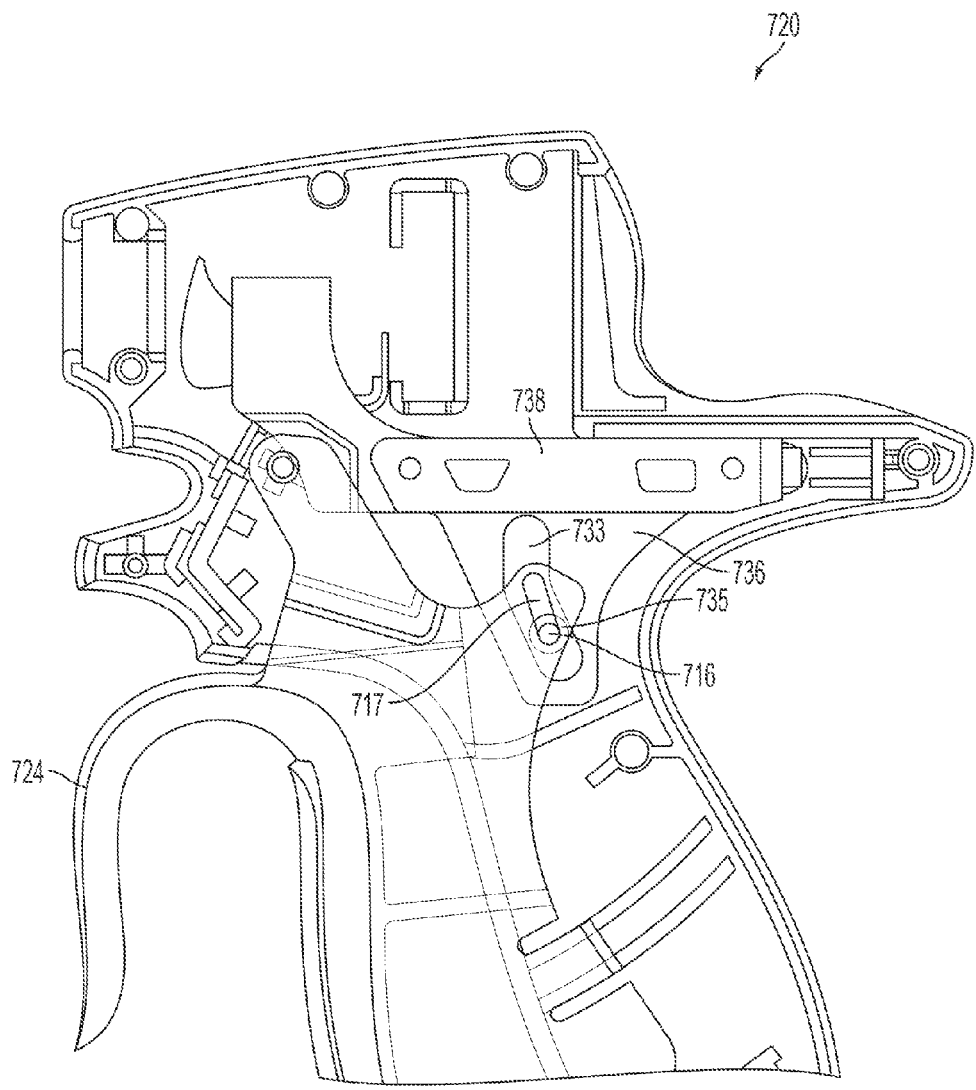
Figure 15C:
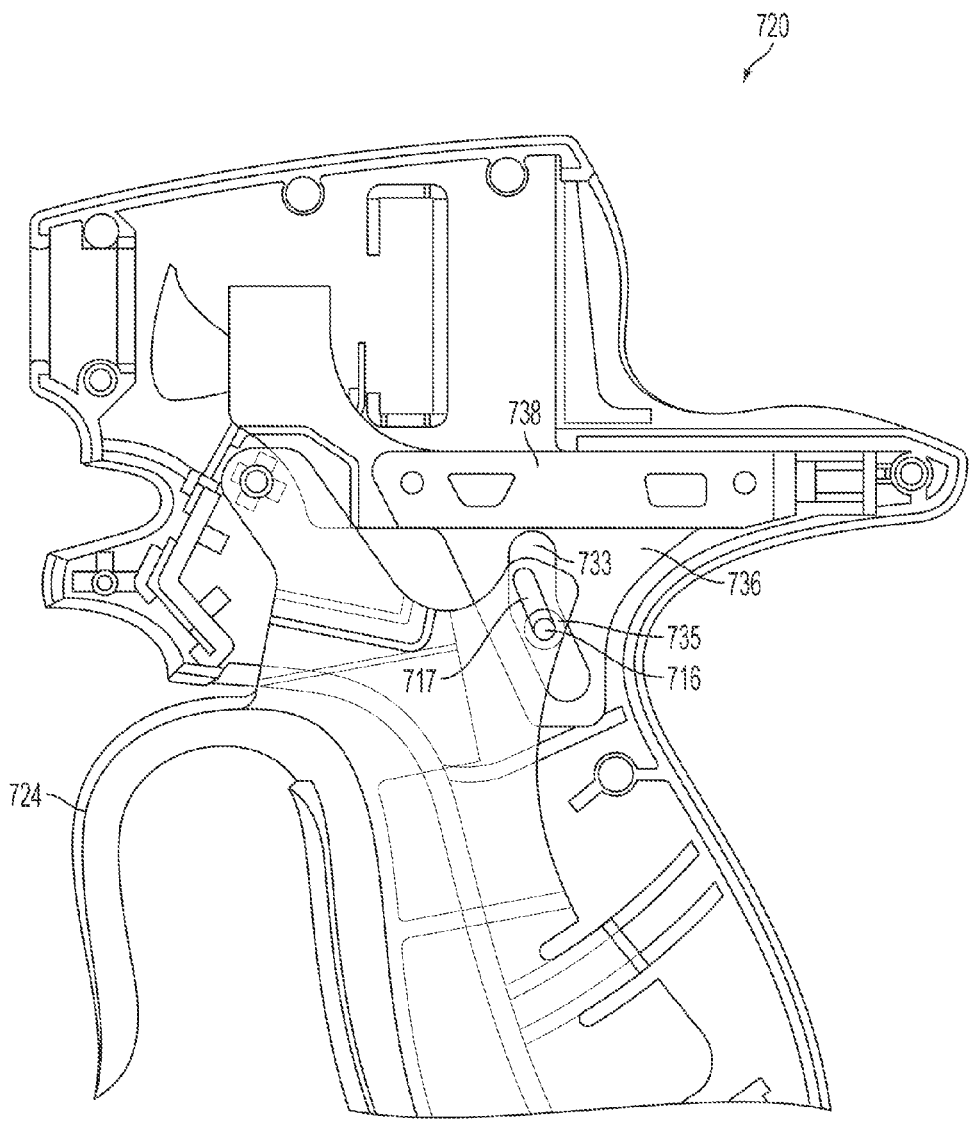

In various embodiments, referring to FIGS. 15A-4, hand piece 720 may generally comprise yoke 738 longitudinally slideable relative to hand piece 720, trigger 724 pivotally attached to yoke 738, and link arm 736 fixedly attached to yoke 738. Link arm 736 may comprise slot 733. Trigger 724 may comprise trigger slot 717. Trigger 724 may be coupled to link arm 736 by trigger pin 716. Trigger pin 716 may be disposed in link pin 732. One end of trigger pin 716 may be disposed in trigger slot 717. One end of link pin 732 may be disposed in trigger slot 717 and the other end of link pin 732 may be disposed in slot 733. In various embodiments, slots 717, 733 may be configured to act as a cam and trigger pin 716 and link pin 732 may be configured to act as a cam follower. In various embodiments, slots 716, 733 may individually comprise a first portion and a second portion. In various embodiments, the first portion of slot 733 may comprise an angled feature and the second portion of slot 733 may comprise a vertical feature relative to the longitudinal axis. For example, as shown in FIG. 15A, the first portion of slot 733 may extend distally and vertically from a plane including the longitudinal axis of hand piece 220, and the second portion of slot 733 may extend perpendicular parallel to the plane including the longitudinal axis of hand piece 220.

Figure 15D:
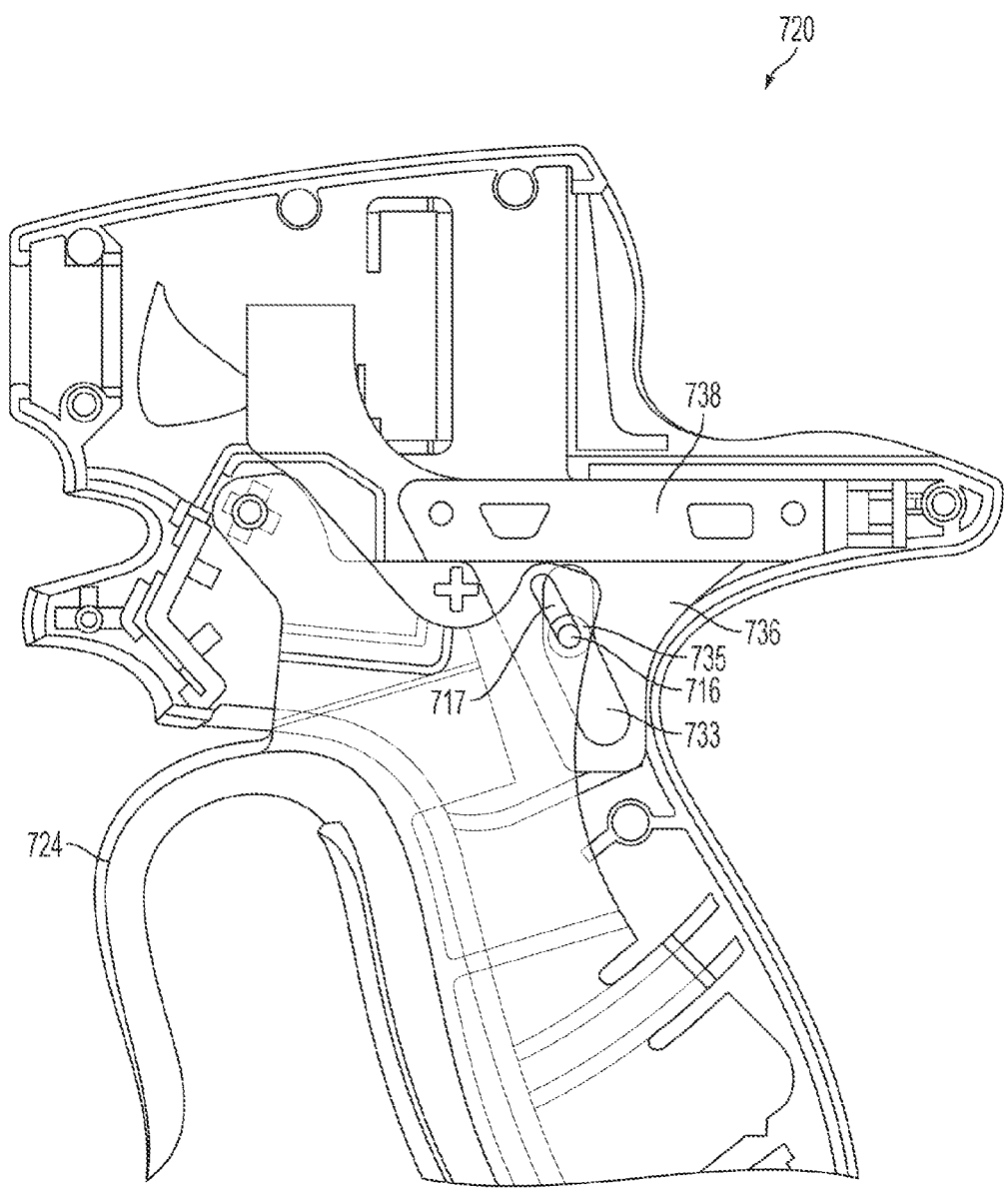
Figure 15E:
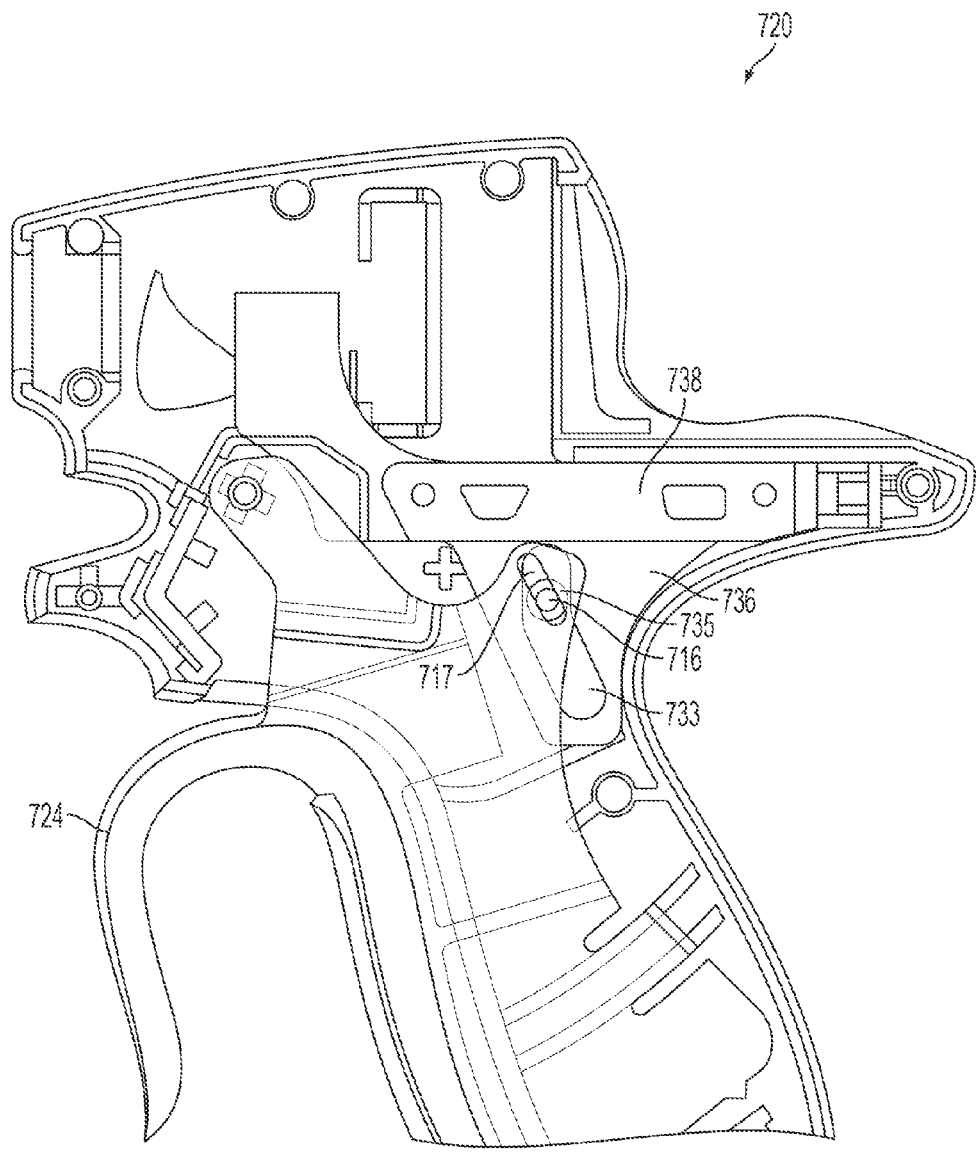
Figure 15F:
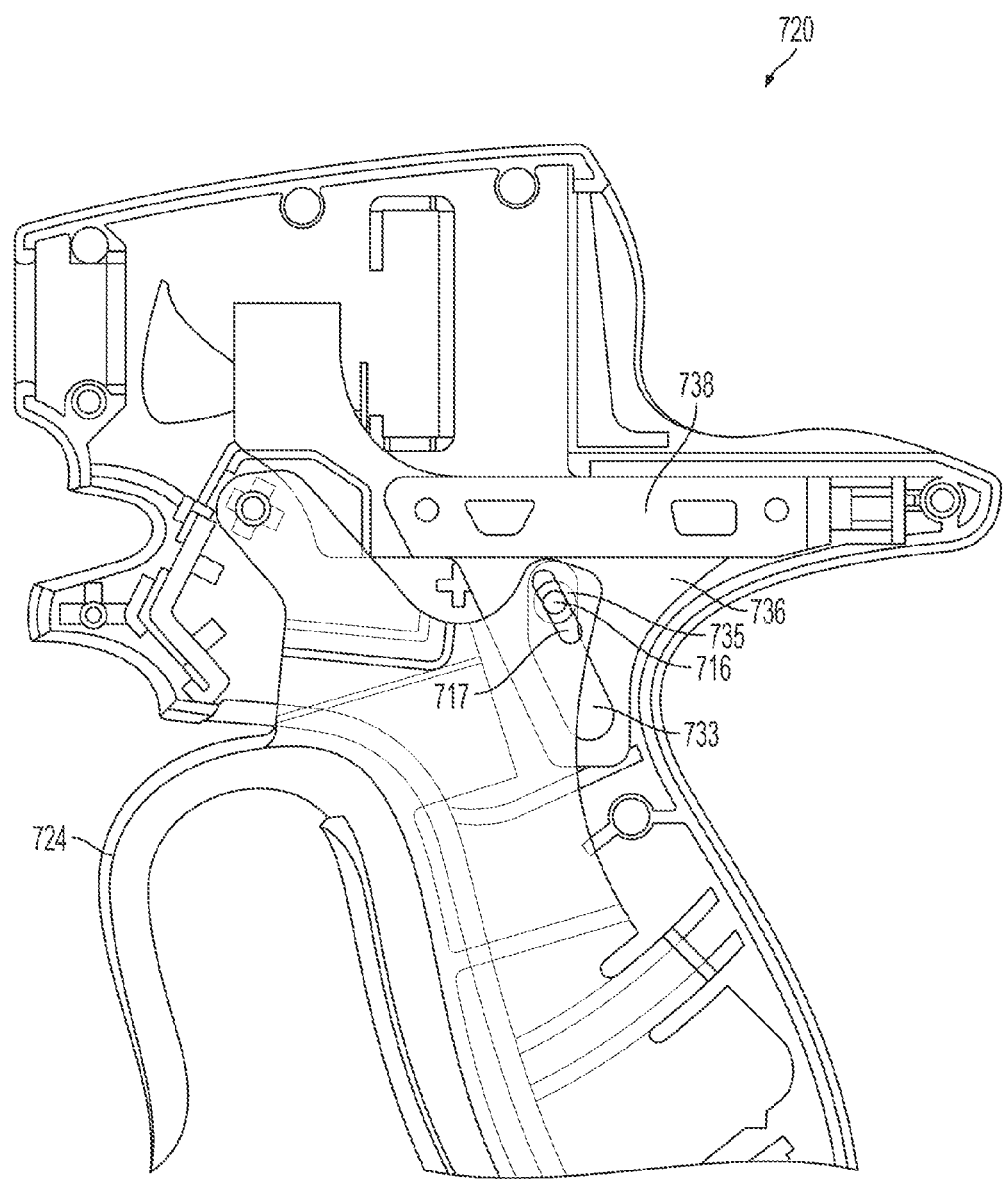
Figure 15G:
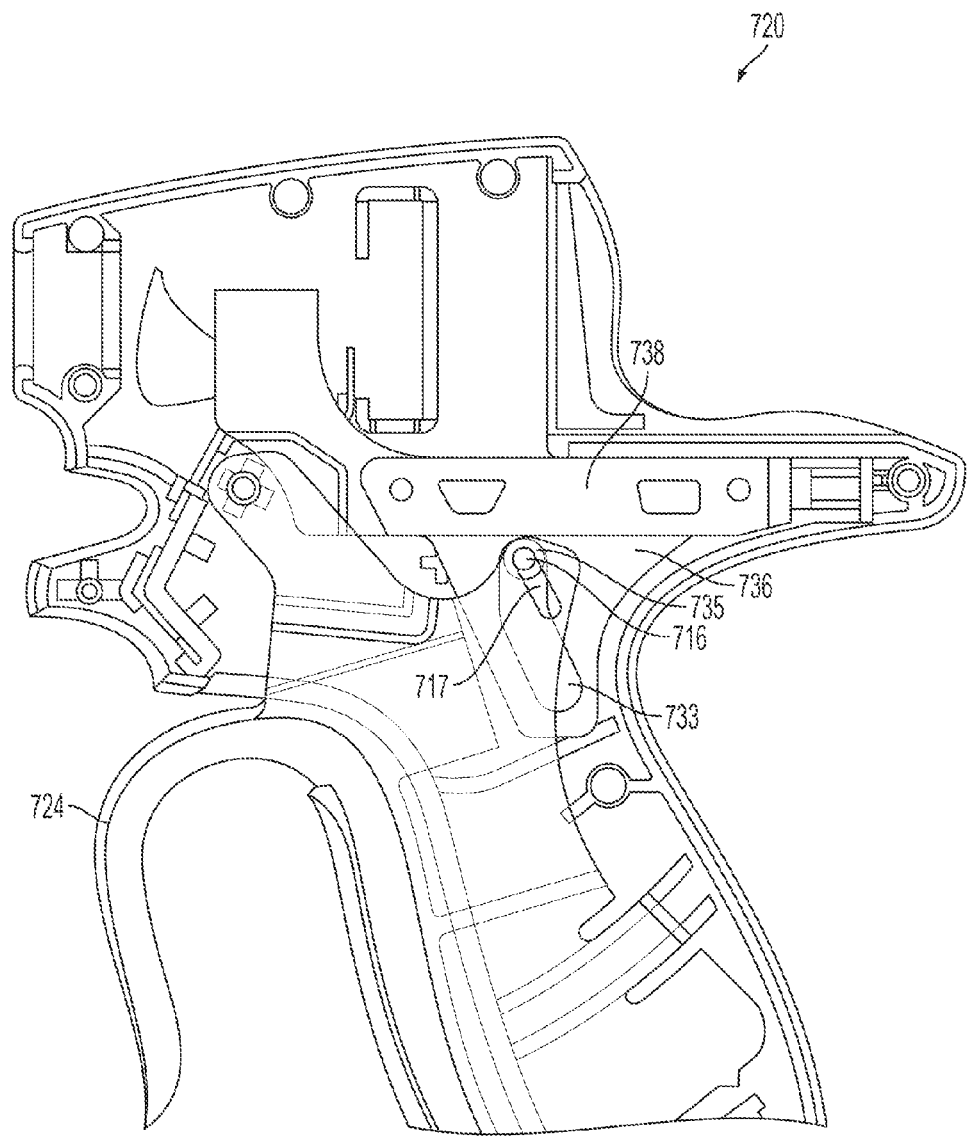
Figure 15H:
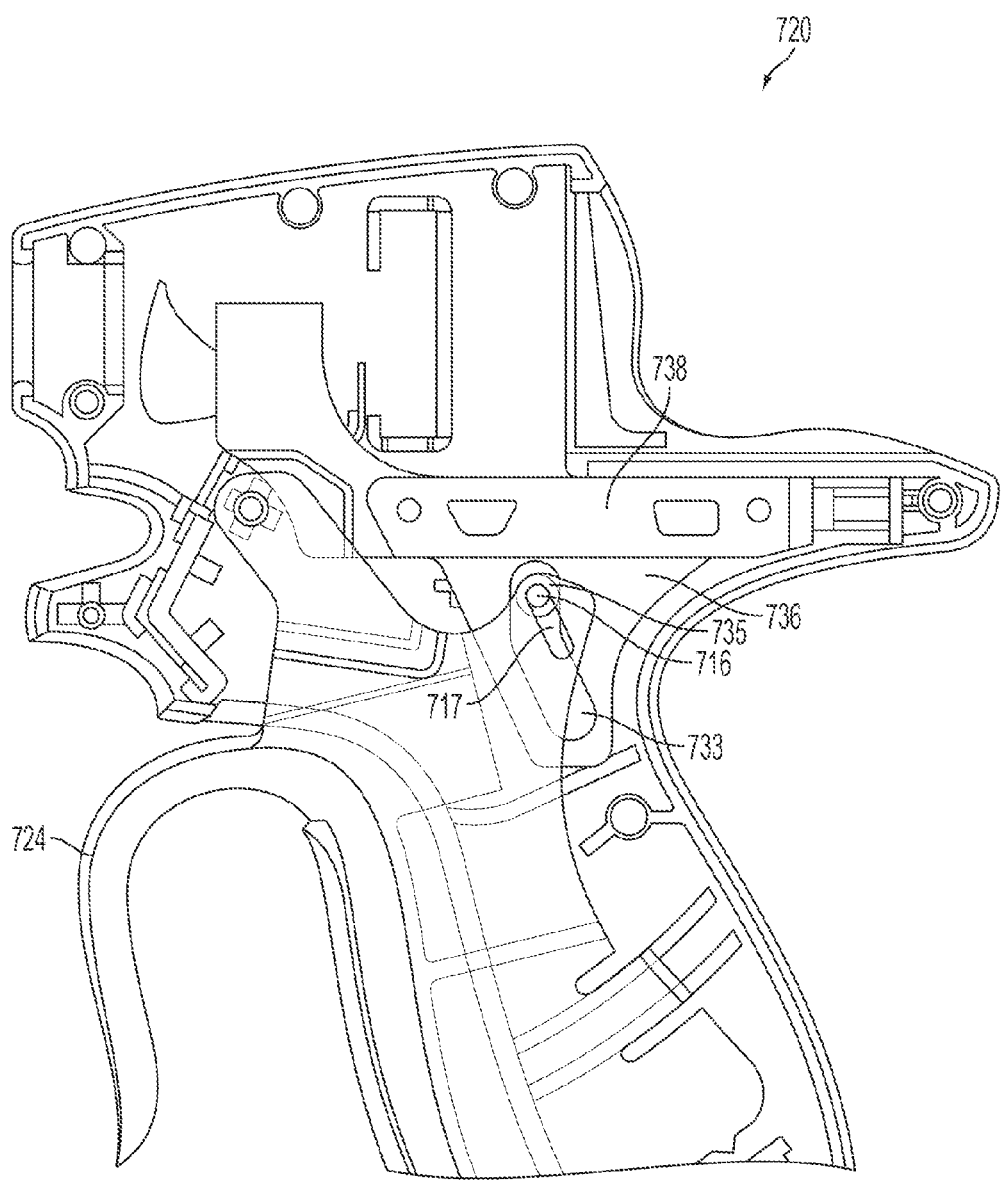
Figure 15I:
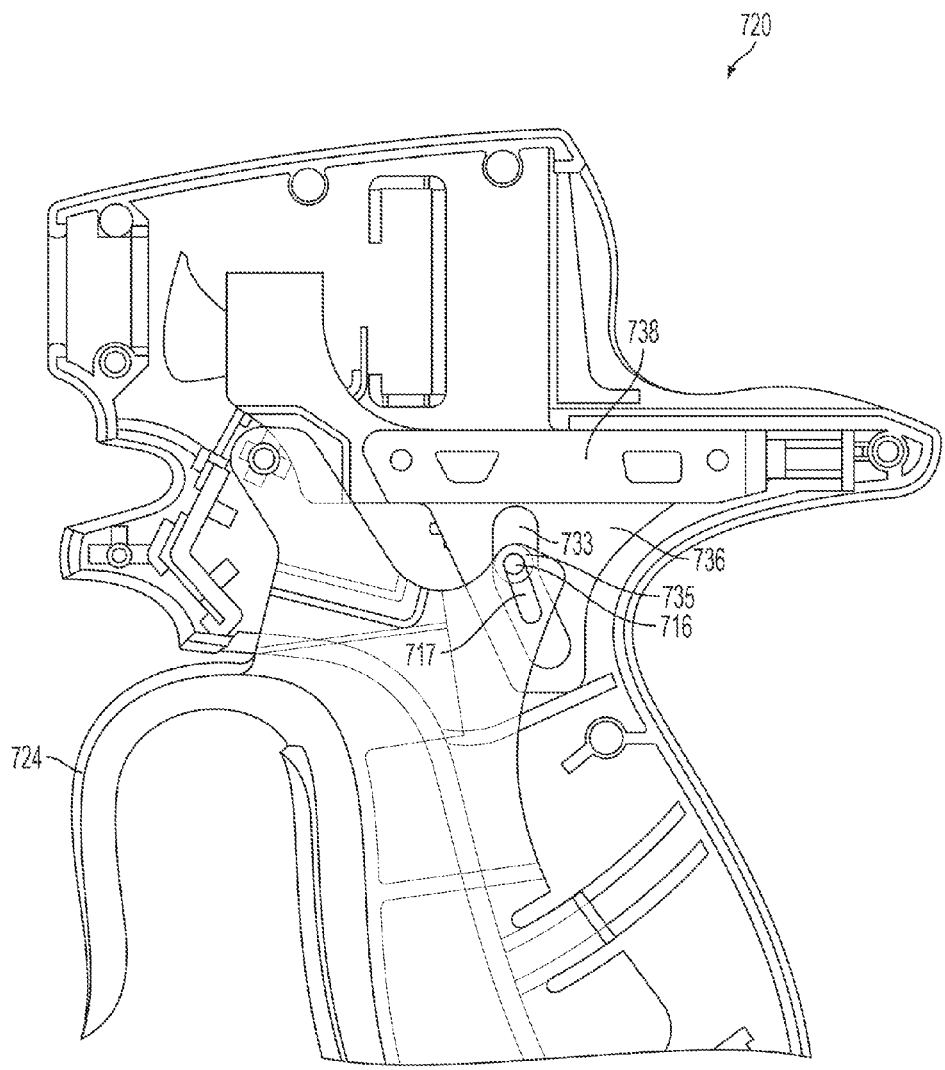

In use, referring to FIGS. 15A-K, when trigger 724 moves from an unactuated position (FIG. 15A) through the first range of motion (FIGS. 15B, 15C) to the first actuated position, link pin 732 slides along the first portion of slot 733 to convert the movement of trigger 724 into proximal linear movement of yoke 738. In various embodiments, link pin 732 may contact a first portion of trigger slot 717 when trigger 724 is in the unactuated position and first actuated position. In various embodiments, trigger pin 717 may not move in trigger slot 716 when trigger 724 moves through the first range of motion. The first actuated position is illustrated in FIG. 15D. Trigger 724 may continue to move from the first actuated position through a second range of motion (FIG. 15E, 15F) to the second actuated position when trigger pin 716 slides along a second portion of slots 717, 733 to convert the movement of trigger 724 into distal linear movement of yoke 738. The second actuated position is illustrated in FIG. 15G. As described above, in various embodiments, yoke 738 may travel a first distance through the first range of motion and a second distance through a second range of motion such that the difference between the first distance and second distance may decrease the compressive force applied to captured tissue from the first compressive force to the second compressive force. In various embodiments, as shown in FIGS. 15D, 15G, the second distance may relate to the length of trigger slot 717.

Figure 15J:
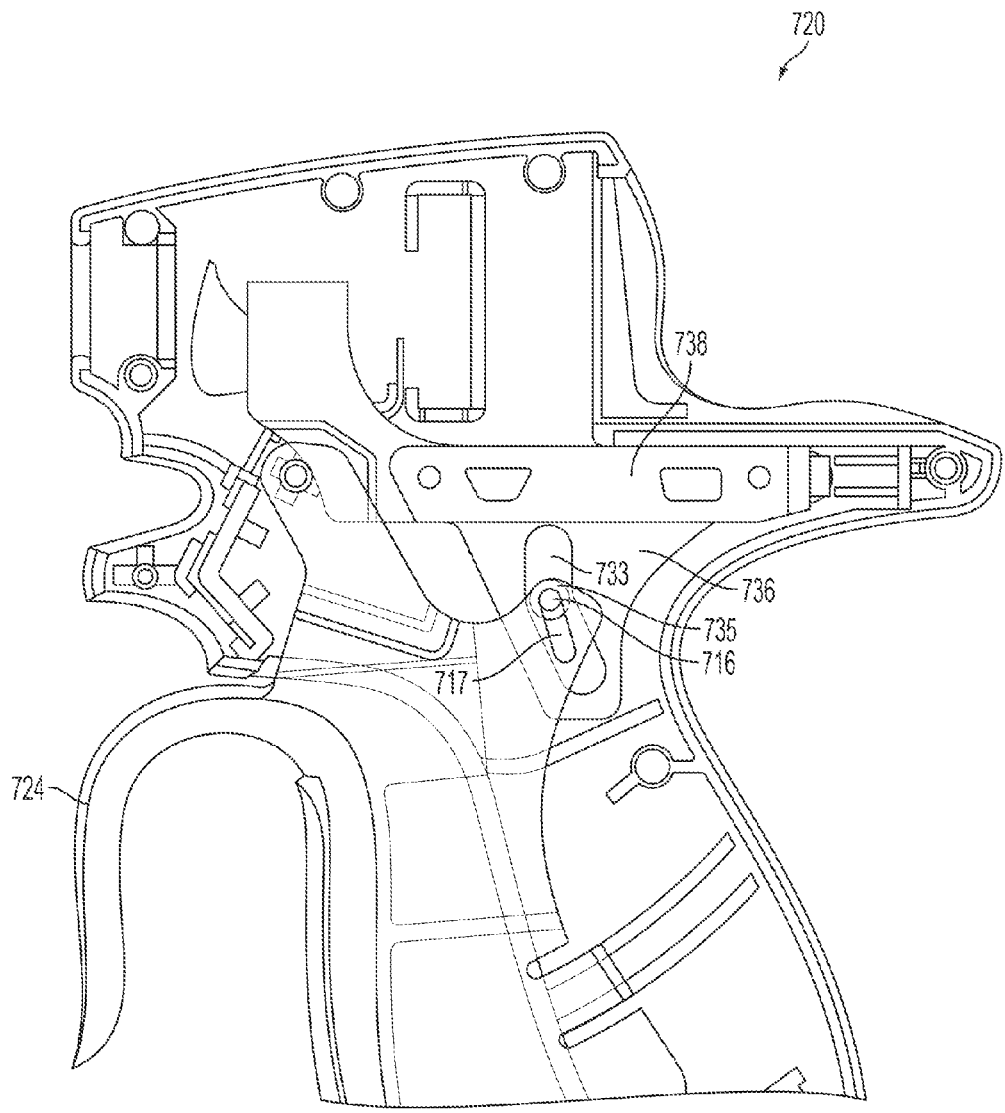
Figure 15K:
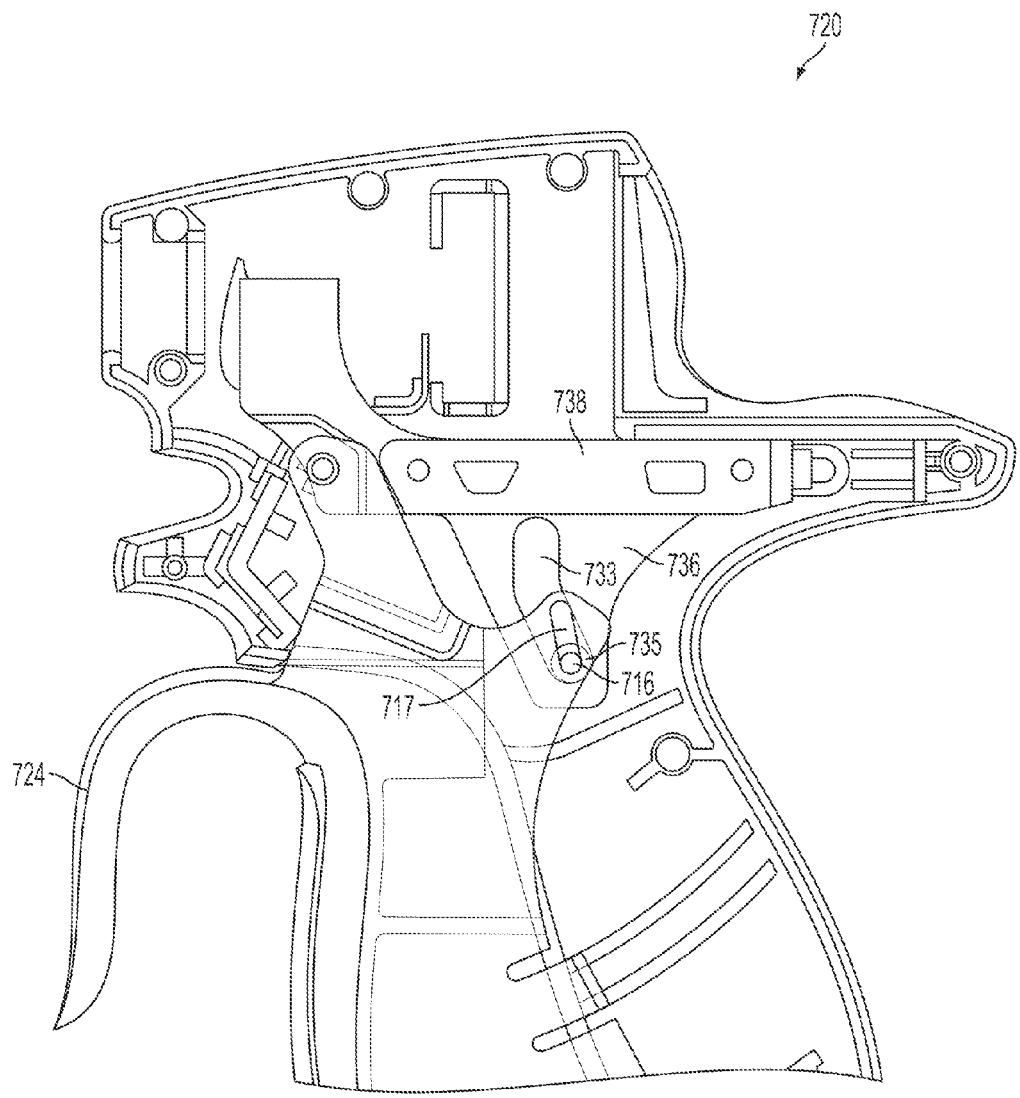

Referring to FIGS. 15G-K, when trigger 724 moves from the second actuated position (FIG. 15G) through the third range of motion (FIGS. 15H-J) to the unactuated position (FIG. 15K), a spring (not shown) may return trigger 724 to an unactuated position where it is pivoted away from the longitudinal axis. In various embodiments, referring to FIGS. 15H and 15I, the user may release trigger 724, and trigger pin 716 may slide along the second portion of slot 733 to the first portion of slot 733 while remaining stationary in the second portion of trigger slot 717. Referring to FIG. 15J, when trigger pin 716 contacts the first portion of slot 733, trigger pin 716 may slide along the second portion of trigger slot 717 to the first portion of slot 717. As trigger 724 continues to rotate away from the longitudinal axis, link pin 732 slides along the first portion of slots 733 to convert the movement of trigger 724 into distal linear movement of yoke 738. The unactuated position is illustrated in FIG. 15K. In various embodiments, at least one of slots 717, 733 may prevent trigger 724 from over travel and locking.

In various embodiments, a surgical instrument may be configured to apply a compressive force to captured tissue. As described above, for example, jaws may be apply a compressive force to tissue captured therebetween. In various embodiments, referring to FIGS. 17A-H, the compressive force may comprise an opposing compressive force and/or a rolling compressive force. As shown in FIGS. 17A-D, the inner and outer layers of a vessel may remain adhered when subjected to opposing compressive force and energy is applied to the tissue. The adventitia layer may retract under heat resulting in an inner muscle layer bond. The inner muscle layer bond may be weaker than an adventitia-adventitia bond. In various embodiments, jaws may apply opposing compressive force and rolling compressive force to mechanically separate the inner and outer vessel layers when jaws close. As shown in FIGS. 17E-H, the inner and outer layers of the vessel may separate when subject to opposing compressive force and rolling compressive force. The separated inner muscle layer may retract before the adventitia layer, and thereby, an adventitia-adventitia bond may be formed when energy is applied to the tissue. The separation of the inner muscle layer may reduce the occurrence of the adventitia layer retracting during sealing by allowing the inner muscle layer to retract inside the vessel as heat begins to build. In various embodiments, sealing and/or welding compressed and rolled tissue layers may form a stronger adventitia-adventitia bond relative to sealing and/or welding compressed tissue layers.

Figure 18A:
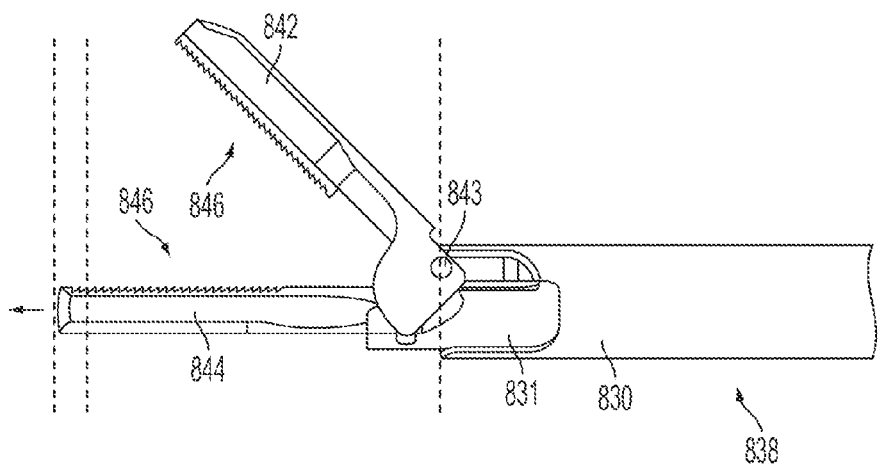
FIGS. 18A and 18B include a surgical instrument comprising an end effector in various positions according to various embodiments.
Figure 18B:
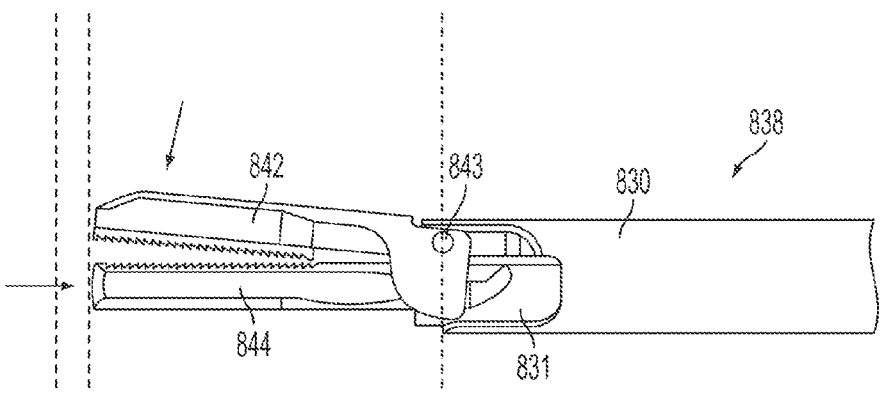
Figure 19A:
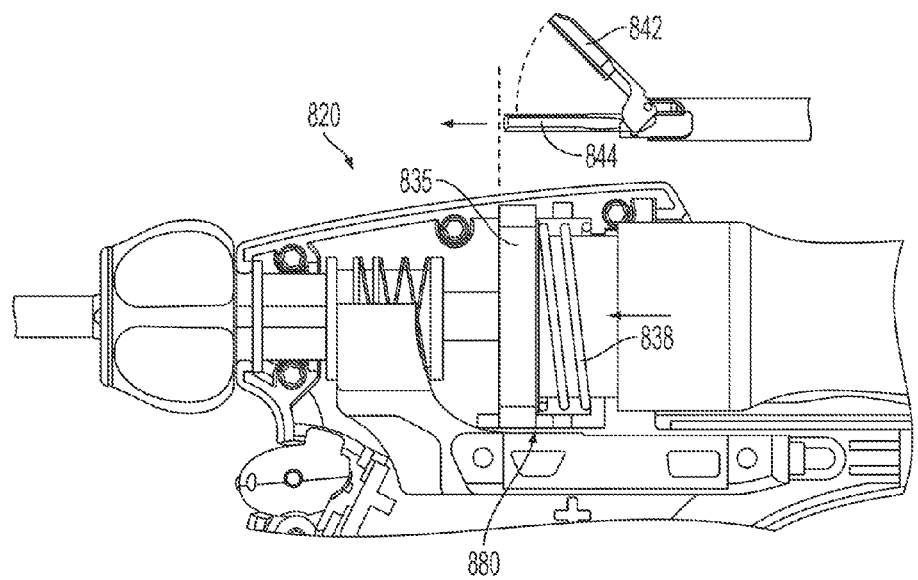
FIGS. 19A and 19B include a side elevational view of the handle assembly of a surgical instrument with a housing half removed according to various embodiments.
Figure 19B:
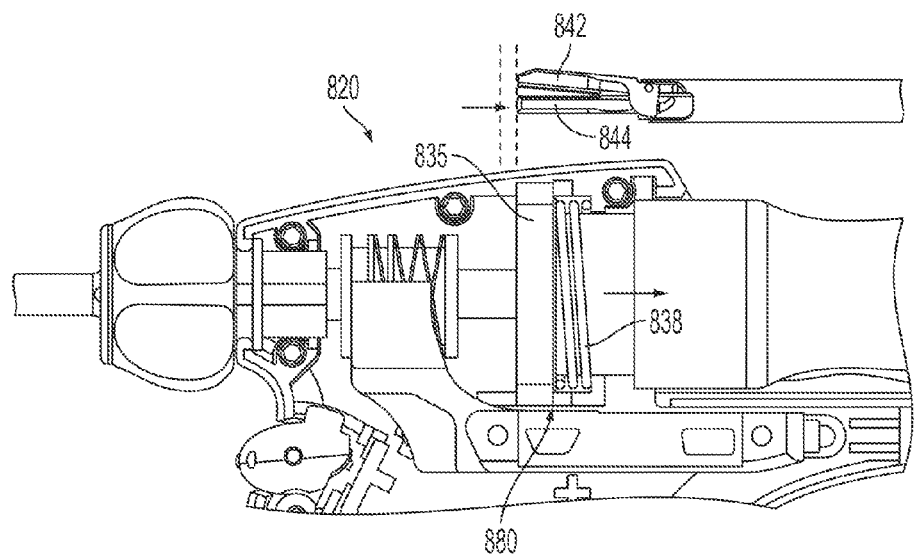

Referring to FIGS. 18A and 18B, in various embodiments, end effector 840 may comprise first jaw 842 and second jaw 844. Second jaw 844 is longitudinally slideable relative to shaft 830; while first jaw 842 pivots relative to shaft 830, toward and away from second jaw 844. First jaw 842 and second jaw 844 may comprise a plurality of teeth serrations 846. The teeth serrations 846 may allow tissue to be grasped, manipulated, coagulated, and/or cut without slipping between jaws 842, 844. In various embodiments, hand piece 820 may comprise connector base 835 configured to retract second jaw 844 relative to shaft 830. Referring to FIGS. 19A and 19B, connector base 835 and second jaw 844 may be resiliently biased to a distal position by spring 838. As shown in the insert in FIG. 19A, jaw 842 may not extend to the tip of jaw 844. Connector base is configured to cam against a ramp features in hand piece 820 to retract second jaw 844 relative to shaft 830 when firing beam is retracted to a proximal position. Hand piece 820 may include stop members 880 located proximal to connector base 835 and spring 838. As shown in FIG. 19B, stop member 880 is configured to engage a proximal face of connector base 835 when firing beam advances distally to close jaws 842, 844. This camming capability may facilitate use of end effector 840 to separate layers of tissue, such as, for example, the adventitia layer and inner muscle layers of a vessel. As shown in the insert in FIG. 19B, jaw 844 may move proximally to contact the tip of jaw 842 in the closed position. In various embodiments, longitudinal movement of the actuator may provide pivoting of first jaw 842 relative to shaft 830 and relative to second jaw 844 and retraction of second jaw 844 relative to shaft 830.

In various embodiments, a surgical instrument may generally comprise a shaft comprising a proximal end and a distal end; an ultrasonic waveguide at least partially positioned within the shaft, the waveguide having a proximal end and a distal end; an ultrasonically actuated blade positioned at the distal end of the waveguide; a clamp arm assembly pivotally connected to the distal end of the shaft, wherein the clamp arm assembly comprises at least two camming members rotationally attached to a clamp arm, wherein the clamp arm is movable between an open position and a closed position relative to the blade to compress tissue intermediate the clamp arm and blade when in the closed position, and wherein the at least two camming members rotate in opposite directions when the clamp arm moves from the open position and a closed position. In various embodiments, the at least two camming members may selectively compress tissue at a first compressive force when a first portion of the camming member contacts tissue and a second compressive force when a second portion of the camming member contacts tissue. In various embodiments, the first compressive force may be different from the second compressive force. In various embodiments, the first compressive force may be greater than or equal to the second compressive force. It may be contemplated to combine the aforementioned configuration with alternative energy modalities or combinations thereof as mentioned earlier in this specification.

Figure 20:
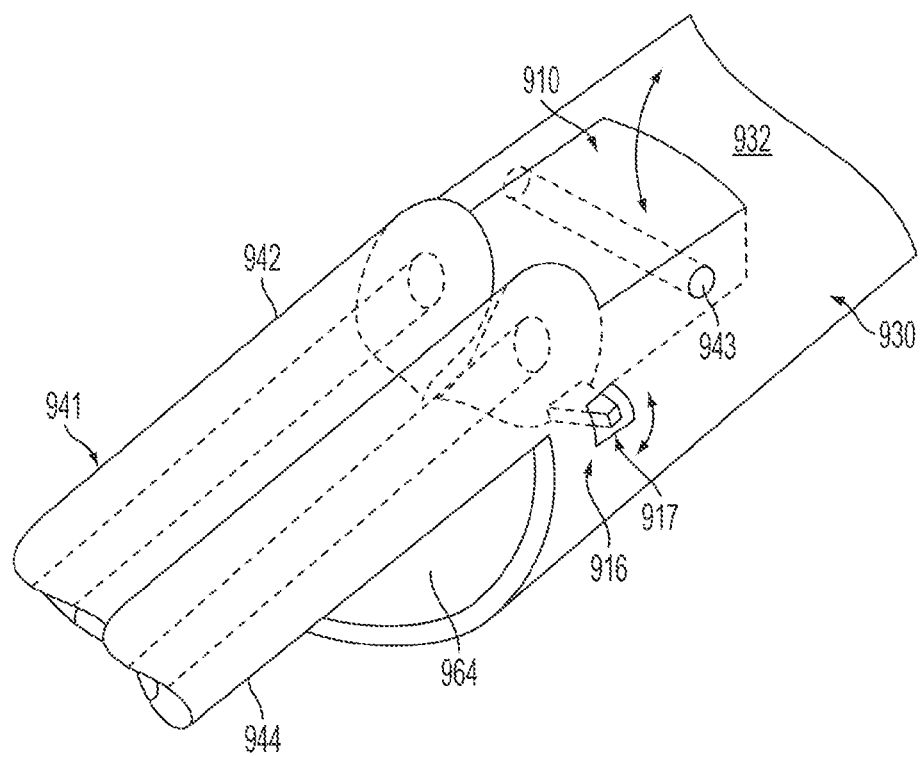
FIG. 20 includes an end effector comprising rotational features according to various embodiments.

In various embodiments, referring to FIG. 20, an end effector 910 may comprise clamp arm assembly 941 to grip tissue and/or compress tissue against ultrasonic blade 964. Clamp arm assembly 941 may be pivotally attached to the distal end of shaft 930 by pivot pin 943. In various embodiments, clamp arm assembly 941 pivots relative to blade 964, toward and away from blade 964. As described above, actuators (not shown) may extend through sheath 932 and be joined with clamp arm 941 and at pivotal coupling 943 such that longitudinal movement of the actuator through shaft 930 provides pivoting of clamp arm 941 relative to shaft 930 and relative to blade 964. Of course, clamp arm 941 may instead have any other suitable kind of movement and may be actuated in any other suitable fashion. In various embodiments, clamp arm assembly may comprise at least one camming member 942, 944 rotationally attached to clamp arm 941. Each the camming member 942, 944 may independently rotate in one of a clockwise direction and a counter clockwise direction relative to shaft 930 and blade 964 when clamp arm 941 is moved from the open position to the closed position. In various embodiments, camming members 942, 944 may rotate in opposite directions. In various embodiments, the camming members 942, 944 may rotate in the same direction. In various embodiments, camming members 942, 944 may rotate simultaneously. In various embodiments, camming members 942, 944 may rotate separately.

In various embodiments, clamp arm 941 may comprise actuating pin 917 for rotating camming member 944 relative to waveguide 964. Actuating pin 917 may be located at a proximal end of camming member 944. Actuating pin 917 may operatively engage with notch 916 of shaft 930 when clamp arm 941 pivots to rotate camming member 944. For example, actuating pin 917 may engage notch 916 when clamp arm 941 pivots toward blade 964 to rotate camming member 944 counterclockwise. Actuating pin 917 may engage notch 916 when clamp arm 941 pivots away from blade 964 to rotate camming member 944 clockwise. In various embodiments, each camming member 942, 944 may comprise actuating pin to individually engage with a corresponding notch in shaft 930. In various embodiments, camming member 944 may comprise actuating pin 917 to engage with notch 916 of shaft 930 and gears (not shown) to operatively engage with gears (not shown) of at least one other camming member 942, 944 such that rotational movement of camming member 944 rotates camming member 942. Of course, camming members 942, 944 may instead have any other suitable kind of movement and may be actuated in any other suitable fashion.

Figure 21A:
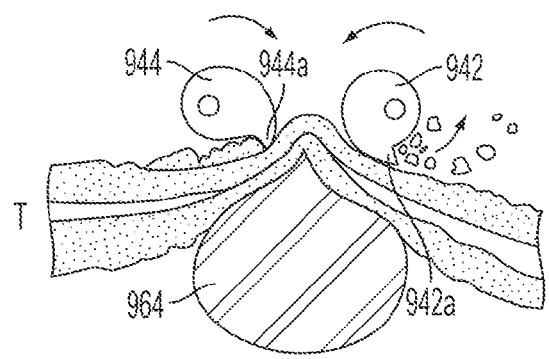
FIGS. 21A and 21B includes a camming member comprising a protrusion according to various embodiments Corresponding reference characters indicate corresponding parts throughout the several views. The exemplifications set out herein illustrate various embodiments of the invention, in one form, and such exemplifications are not to be construed as limiting the scope of the invention in any manner.
Figure 21B:
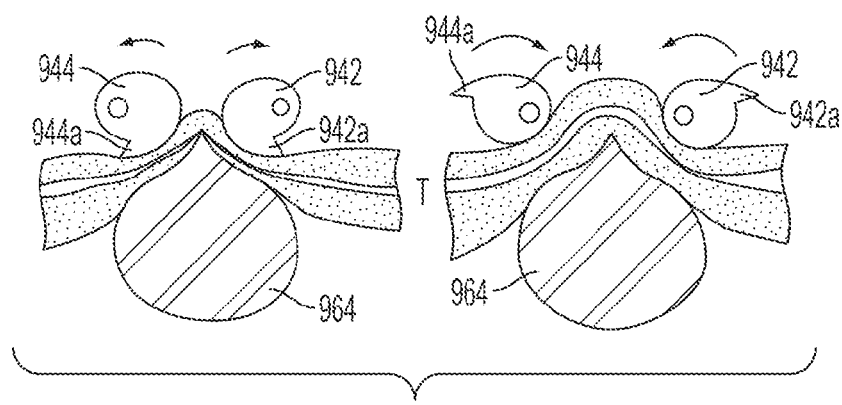

In various embodiments, the camming member may selectively compress tissue at a first compressive force when a first portion of the camming member contacts tissue and a second compressive force when a second portion of the camming member contacts tissue, wherein the first compressive force is different from the second compressive force. In various embodiments, the first compressive force is greater than the second compressive force. In various embodiments, referring to FIGS. 21A and 21B, camming members 942, 944 may comprise a generally circumferential tissue T contacting surface comprising at least one protrusion 942a, 944a. The protrusions 942a, 944a may extend above the surface of the camming members 942, 944, respectively. In various embodiments, protrusion 942a, 944a may comprise a curved portion of a generally comma-shape. In various embodiments, camming members 942, 944 may selectively compress tissue T at a first compressive force when a first portion of camming member 942, 944 comprising protrusion 942a, 944a contacts tissue T and a second compressive force when a second portion of the camming member 942, 944 lacking the protrusion contacts tissue T. In various embodiments, the camming members 942, 944 may contact the tissue T and rotationally engage the tissue T to shear and/or scrape any calcification on the external and/or internal surfaces of the tissue T.

While various embodiments described above include a pistol grip, it should be understood that the foregoing teachings may be readily applied to devices having various other kinds of grips. By way of example only, a variation of trigger and cam lever may be provided in accordance with the above teachings in a device having a scissor grip. Various examples of devices comprising a scissor grip is described in U.S. patent application Ser. No. 13/426,084, filed Mar. 21, 2012, entitled "ENERGY-BASED SCISSORS DEVICE", the disclosure of which is incorporated by reference herein. Other kinds of grips that may be combined with the above teachings will be apparent to those of ordinary skill in the art. Furthermore, a variation of trigger and cam lever may be readily incorporated into devices having various other kinds of end effectors, including but not limited to tissue graspers, tissue retrieval pouch deploying instruments, surgical staplers, ultrasonic surgical instruments, etc.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of this application.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
   a shaft comprising a proximal end and a distal end;
   an end effector extending from the distal end of the shaft, wherein the end effector is operable to grasp tissue;
   a handle extending from the proximal end, wherein the handle comprises a gripping portion; and
   a trigger assembly extending from the handle, wherein the trigger assembly comprises a trigger movable relative to the gripping portion between an unactuated position and a first actuated position and a second actuated position, wherein the trigger is operable to control the end effector to selectively grasp tissue at a first compressive force when the trigger is in the first actuated position and a second compressive force when the trigger is in the second actuated position;
   wherein the trigger assembly comprises:
      a yoke longitudinally slideable relative to the handle and longitudinally engaging the trigger;
      a link arm comprising a slot; and
      a trigger pin disposed in the slot, wherein the trigger pin links the trigger and link arm;
      wherein the trigger pin engages a first portion of the slot when the trigger is in the first actuated position and a second portion of the slot when the trigger is in the second actuated position.

2. The surgical instrument of claim 1, wherein the first compressive force is greater than the second compressive force.

3. The surgical instrument of claim 1, wherein the first compressive force and second compressive force are independently selected from 1 psi to 10 psi.

4. The surgical instrument of claim 1, wherein the trigger assembly comprises:
- a lever arm extending distally from the trigger, wherein the lever arm comprises a slot; and
- a leaf spring comprising a free end disposed in the slot of the lever arm;
- wherein the free end of the leaf spring engages a first portion of the slot of the lever arm when the trigger is in the first actuated position and a second portion of the slot of the lever arm when the trigger is in the second actuated position.

5. A surgical instrument, comprising:
- a shaft comprising a proximal end and a distal end;
- an end effector extending from the distal end of the shaft, wherein the end effector is operable to grasp tissue;
- a handle extending from the proximal end, wherein the handle comprises a gripping portion; and
- a trigger assembly extending from the handle, wherein the trigger assembly comprises a trigger movable relative to the gripping portion between an unactuated position and a first actuated position and a second actuated position, wherein the trigger is operable to control the end effector to selectively grasp tissue at a first compressive force when the trigger is in the first actuated position and a second compressive force when the trigger is in the second actuated position;
- wherein the trigger assembly comprises:
  - a yoke longitudinally slideable relative to the handle and longitudinally engaging the trigger, wherein the trigger comprises a cam feature; and
  - a link arm pivotally attached to a yoke, wherein the link arm comprises a cam follower to engage the cam feature;
- wherein the cam follower engages a first portion of the cam feature when the trigger is in the first actuated position and a second portion of the cam feature when the trigger is in the second actuated position.

6. A surgical instrument, comprising:
- a shaft comprising a proximal end and a distal end;
- an end effector extending from the distal end of the shaft, wherein the end effector is operable to grasp tissue;
- a handle extending from the proximal end, wherein the handle comprises a gripping portion; and
- a trigger assembly extending from the handle, wherein the trigger assembly comprises a trigger movable relative to the gripping portion between an unactuated position and a first actuated position and a second actuated position, wherein the trigger is operable to control the end effector to selectively grasp tissue at a first compressive force when the trigger is in the first actuated position and a second compressive force when the trigger is in the second actuated position;
- wherein the trigger assembly comprises:
  - the trigger comprising a trigger slot and a cam feature comprising a trigger notch;
  - a link arm pivotally attached to a yoke, wherein the link arm comprises a cam follower to engage the cam feature; and
  - a trigger pin disposed in the slot, wherein the trigger pin links the trigger and link arm;
  - wherein the cam follower engages a first portion of the notch when the trigger is in the first actuated position and a second portion of the notch when the trigger is in the second actuated position; and
  - wherein the trigger pin engages a first portion of the trigger slot when the trigger is in the first actuated position and a second portion of the trigger slot when the trigger is in the second actuated position.

7. A surgical instrument, comprising:
- a shaft comprising a proximal end and a distal end;
- an end effector extending from the distal end of the shaft, wherein the end effector is operable to grasp tissue;
- a handle extending from the proximal end, wherein the handle comprises a gripping portion; and
- a trigger assembly extending from the handle, wherein the trigger assembly comprises a trigger movable relative to the gripping portion between an unactuated position and a first actuated position and a second actuated position, wherein the trigger is operable to control the end effector to selectively grasp tissue at a first compressive force when the trigger is in the first actuated position and a second compressive force when the trigger is in the second actuated position;
- wherein the trigger assembly comprises:
  - a handle comprising a cam feature comprising a cam slot; and
  - a link arm pivotally attached to a yoke, wherein the link arm comprises a linkage pin disposed in the cam slot;
  - a trigger comprising a trigger slot;
  - a trigger pin disposed in the trigger slot, wherein the trigger pin links the trigger and link arm;
  - wherein the linkage pin engages a first portion of the cam slot when the trigger is in the first actuated position and a second portion of the cam slot when the trigger is in the second actuated position; and
  - wherein the trigger pin engages a first portion of the trigger slot when the trigger is in the first actuated position and a second portion of the trigger slot when the trigger is in the second actuated position.

8. A surgical instrument, comprising:
- a shaft comprising a proximal end and a distal end;
- an end effector extending from the distal end of the shaft, wherein the end effector is operable to grasp tissue;
- a handle extending from the proximal end, wherein the handle comprises a gripping portion; and
- a trigger assembly extending from the handle, wherein the trigger assembly comprises a trigger movable relative to the gripping portion between an unactuated position and a first actuated position and a second actuated position, wherein the trigger is operable to control the end effector to selectively grasp tissue at a first compressive force when the trigger is in the first actuated position and a second compressive force when the trigger is in the second actuated position;
- wherein the handle comprises a cam feature comprising a slot; and
- wherein the trigger assembly comprises:
  - a link arm pivotally attached to the trigger; and
  - a yoke longitudinally slideable relative to the handle and longitudinally engaging the trigger, wherein the yoke comprises a cam feature comprising a notch, and
  - a yoke pin comprising a first end disposed in the slot and a second end disposed in the notch;
- wherein the first end of the yoke pin engages a first portion of the slot and the second end of the yoke pin engages a first portion of the notch when the trigger is in the first actuated position and the first end of the yoke pin engages a second portion of the slot and the second end of the yoke pin engages a second portion of the notch when the trigger is in the second actuated position.

9. The surgical instrument of claim 8, wherein the trigger assembly provides an audible and/or tactile signal when the link pin engages at least one of the second portion of the slot and second portion of the notch.

10. A surgical instrument, comprising:
   a shaft comprising a proximal end and a distal end;
   an end effector extending from the distal end of the shaft, wherein the end effector is operable to grasp tissue;
   a handle extending from the proximal end, wherein the handle comprises a gripping portion; and
   a trigger assembly extending from the handle, wherein the trigger assembly comprises a trigger movable relative to the gripping portion between an unactuated position and a first actuated position and a second actuated position, wherein the trigger is operable to control the end effector to selectively grasp tissue at a first compressive force when the trigger is in the first actuated position and a second compressive force when the trigger is in the second actuated position;
   wherein the trigger assembly comprises:
      a yoke longitudinally slideable relative to the handle;
      a link arm pivotally attached to the yoke and slidingly attached to the trigger, wherein the link arm comprises a cam feature comprising a cam slot;
      a trigger pin linking the trigger and link arm, wherein the trigger pin is disposed in the cam slot;
      wherein the trigger pin engages a first portion of the cam slot when the trigger is in the first actuated position and a second portion of the cam slot when the trigger is in the second actuated position.

11. The surgical instrument of claim 1, wherein the end effector comprises:
   a first jaw;
   a second jaw, wherein at least one of the first jaw and second jaw is movable relative to the other of the first jaw and second jaw between an open position and a closed position; and
   at least one electrode to apply electrosurgical energy to weld tissue.

12. The surgical instrument of claim 11, wherein the at least one electrode is coupled to a radiofrequency (Rf) energy source.

13. The surgical instrument of claim 12 comprising a lockout mechanism to prevent current from flowing from the energy source to the at least one electrode unless the trigger is in the second actuated position.

14. The surgical instrument of claim 11, wherein one of the first jaw and second jaw is longitudinally movable between a first position and a second position relative to the other of the first jaw and second jaw, wherein the one of the first jaw and second jaw is in the first position when the trigger is in the unactuated position and the second position when the trigger is in the first actuated position.

15. The surgical instrument of claim 1, wherein the end effector comprises a firing beam longitudinally movable along at least a portion of the end effector, wherein the firing beam comprises:
   a distal blade to sever tissue, wherein the distal blade comprises opposing surfaces each comprising at least one roller bearing to compress tissue.

16. The surgical instrument of claim 5, wherein the first compressive force is greater than the second compressive force.

17. The surgical instrument of claim 5, wherein the first compressive force and second compressive force are independently selected from 1 psi to 10 psi.

18. The surgical instrument of claim 5, wherein the trigger assembly comprises:
   a lever arm extending distally from the trigger, wherein the lever arm comprises a slot; and
   a leaf spring comprising a free end disposed in the slot;
   wherein the free end of the leaf spring engages a first portion of the slot when the trigger is in the first actuated position and a second portion of the slot when the trigger is in the second actuated position.

19. The surgical instrument of claim 5, wherein the end effector comprises:
   a first jaw;
   a second jaw, wherein at least one of the first jaw and second jaw is movable relative to the other of the first jaw and second jaw between an open position and a closed position; and
   at least one electrode to apply electrosurgical energy to weld tissue.

20. The surgical instrument of claim 5, wherein the end effector comprises a firing beam longitudinally movable along at least a portion of the end effector, wherein the firing beam comprises:
   a distal blade to sever tissue, wherein the distal blade comprises opposing surfaces each comprising at least one roller bearing to compress tissue.

21. The surgical instrument of claim 6, wherein the first compressive force is greater than the second compressive force.

22. The surgical instrument of claim 6, wherein the first compressive force and second compressive force are independently selected from 1 psi to 10 psi.

23. The surgical instrument of claim 6, wherein the trigger assembly comprises:
   a lever arm extending distally from the trigger, wherein the lever arm comprises a slot; and
   a leaf spring comprising a free end disposed in the slot of the lever arm;
   wherein the free end of the leaf spring engages a first portion of the slot of the lever arm when the trigger is in the first actuated position and a second portion of the slot of the lever arm when the trigger is in the second actuated position.

24. The surgical instrument of claim 6, wherein the end effector comprises:
   a first jaw;
   a second jaw, wherein at least one of the first jaw and second jaw is movable relative to the other of the first jaw and second jaw between an open position and a closed position; and
   at least one electrode to apply electrosurgical energy to weld tissue.

25. The surgical instrument of claim 6, wherein the end effector comprises a firing beam longitudinally movable along at least a portion of the end effector, wherein the firing beam comprises:
   a distal blade to sever tissue, wherein the distal blade comprises opposing surfaces each comprising at least one roller bearing to compress tissue.

26. The surgical instrument of claim 7, wherein the first compressive force is greater than the second compressive force.

27. The surgical instrument of claim 7, wherein the first compressive force and second compressive force are independently selected from 1 psi to 10 psi.

28. The surgical instrument of claim 7, wherein the trigger assembly comprises:
  a lever arm extending distally from the trigger, wherein the lever arm comprises a slot; and
  a leaf spring comprising a free end disposed in the slot of the lever arm;
  wherein the free end of the leaf spring engages a first portion of the slot of the lever arm when the trigger is in the first actuated position and a second portion of the slot of the lever arm when the trigger is in the second actuated position.

29. The surgical instrument of claim 7, wherein the end effector comprises:
  a first jaw;
  a second jaw, wherein at least one of the first jaw and second jaw is movable relative to the other of the first jaw and second jaw between an open position and a closed position; and
  at least one electrode to apply electrosurgical energy to weld tissue.

30. The surgical instrument of claim 7, wherein the end effector comprises a firing beam longitudinally movable along at least a portion of the end effector, wherein the firing beam comprises:
  a distal blade to sever tissue, wherein the distal blade comprises opposing surfaces each comprising at least one roller bearing to compress tissue.

31. The surgical instrument of claim 8, wherein the first compressive force is greater than the second compressive force.

32. The surgical instrument of claim 8, wherein the first compressive force and second compressive force are independently selected from 1 psi to 10 psi.

33. The surgical instrument of claim 8, wherein the trigger assembly comprises:
  a lever arm extending distally from the trigger, wherein the lever arm comprises a slot; and
  a leaf spring comprising a free end disposed in the slot of the lever arm;
  wherein the free end of the leaf spring engages a first portion of the slot of the lever arm when the trigger is in the first actuated position and a second portion of the slot of the lever arm when the trigger is in the second actuated position.

34. The surgical instrument of claim 8, wherein the end effector comprises:
  a first jaw;
  a second jaw, wherein at least one of the first jaw and second jaw is movable relative to the other of the first jaw and second jaw between an open position and a closed position; and
  at least one electrode to apply electrosurgical energy to weld tissue.

35. The surgical instrument of claim 8, wherein the end effector comprises a firing beam longitudinally movable along at least a portion of the end effector, wherein the firing beam comprises:
  a distal blade to sever tissue, wherein the distal blade comprises opposing surfaces each comprising at least one roller bearing to compress tissue.

36. The surgical instrument of claim 10, wherein the first compressive force is greater than the second compressive force.

37. The surgical instrument of claim 10, wherein the first compressive force and second compressive force are independently selected from 1 psi to 10 psi.

38. The surgical instrument of claim 10, wherein the trigger assembly comprises:
  a lever arm extending distally from the trigger, wherein the lever arm comprises a slot; and
  a leaf spring comprising a free end disposed in the slot of the lever arm;
  wherein the free end of the leaf spring engages a first portion of the slot of the lever arm when the trigger is in the first actuated position and a second portion of the slot of the lever arm when the trigger is in the second actuated position.

39. The surgical instrument of claim 10, wherein the end effector comprises:
  a first jaw;
  a second jaw, wherein at least one of the first jaw and second jaw is movable relative to the other of the first jaw and second jaw between an open position and a closed position; and
  at least one electrode to apply electrosurgical energy to weld tissue.

40. The surgical instrument of claim 10, wherein the end effector comprises a firing beam longitudinally movable along at least a portion of the end effector, wherein the firing beam comprises:
  a distal blade to sever tissue, wherein the distal blade comprises opposing surfaces each comprising at least one roller bearing to compress tissue.

* * * * *